US010053474B2

(12) United States Patent
Chau et al.

(10) Patent No.: US 10,053,474 B2
(45) Date of Patent: *Aug. 21, 2018

(54) ANTI-VIRAL COMPOUNDS

(71) Applicant: AbbVie Inc., North Chicago, IL (US)

(72) Inventors: Jaclyn Chau, Vancouver (CA); Hui-Ju J. Chen, Grayslake, IL (US); David A. DeGoey, Salem, WI (US); John Hartung, Evanston, IL (US); Nathan Ide, Lindenhurst, IL (US); Vikram Kalthod, North Chicago, IL (US); Allan C. Krueger, Gurnee, IL (US); Yi-Yin Ku, Buffalo Grove, IL (US); Tongmei Li, Lake Bluff, IL (US); John T. Randolph, Libertyville, IL (US); Rolf Wagner, Antioch, IL (US); Geoff T. Halvorsen, Lake Bluff, IL (US); Christopher C. Marvin, Grayslake, IL (US); Eric Voight, Pleasant Prairie, WI (US); Brian S. Brown, Evanston, IL (US); Steven R. Martinez, Chicago, IL (US); Anurupa Shrestha, Gurnee, IL (US); Howard R. Heyman, Deerfield, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/588,037

(22) Filed: May 5, 2017

(65) Prior Publication Data
US 2018/0022763 A1 Jan. 25, 2018

Related U.S. Application Data

(63) Continuation of application No. 15/254,342, filed on Sep. 1, 2016, now Pat. No. 9,676,797.

(60) Provisional application No. 62/213,378, filed on Sep. 2, 2015, provisional application No. 62/242,136, filed on Oct. 15, 2015, provisional application No. 62/253,426, filed on Nov. 10, 2015, provisional application No. 62/294,449, filed on Feb. 12, 2016, provisional application No. 62/296,801, filed on Feb. 18, 2016, provisional application No. 62/321,538, filed on Apr. 12, 2016, provisional application No. 62/327,087, filed on Apr. 25, 2016, provisional application No. 62/351,038, filed on Jun. 16, 2016, provisional application No. 62/363,640, filed on Jul. 18, 2016, provisional application No. 62/375,029, filed on Aug. 15, 2016.

(51) Int. Cl.
*A61K 31/675* (2006.01)
*C07F 9/02* (2006.01)
*C07F 9/08* (2006.01)
*C07F 9/6512* (2006.01)
*C07H 19/10* (2006.01)

(52) U.S. Cl.
CPC ............ *C07F 9/08* (2013.01); *C07F 9/65123* (2013.01); *C07H 19/10* (2013.01)

(58) Field of Classification Search
CPC .......................... C07F 9/65125; C07F 9/5407
USPC ............................................... 514/86; 568/11
See application file for complete search history.

(56) References Cited

U.S. PATENT DOCUMENTS

| | | | | | |
|---|---|---|---|---|---|
| 4,526,988 | A | * | 7/1985 | Hertel | C07D 307/33 536/122 |
| 5,246,924 | A | * | 9/1993 | Fox | A61K 31/70 514/49 |
| 6,060,542 | A | * | 5/2000 | Gooswilligen | C08J 9/30 524/59 |
| 6,060,592 | A | * | 5/2000 | Acevedo | C07H 19/04 536/22.1 |
| 6,596,700 | B2 | * | 7/2003 | Sommadossi | A61K 31/7068 514/45 |
| 6,777,395 | B2 | * | 8/2004 | Bhat | A61K 31/7056 514/43 |
| 6,777,441 | B2 | * | 8/2004 | Wang | C07C 37/002 514/475 |
| 6,787,526 | B1 | * | 9/2004 | Bryant | A61K 31/7068 424/85.4 |
| 6,812,219 | B2 | * | 11/2004 | LaColla | A61K 31/7076 514/25 |
| 6,914,054 | B2 | * | 7/2005 | Sommadossi | A61K 31/708 514/49 |
| 7,101,861 | B2 | * | 9/2006 | Sommadossi | A61K 31/7076 514/25 |
| 7,105,493 | B2 | * | 9/2006 | Sommadossi | A61K 31/7076 514/42 |

(Continued)

FOREIGN PATENT DOCUMENTS

| | | |
|---|---|---|
| CN | 103980332 A | 8/2014 |
| WO | WO-9001036 A1 | 2/1990 |

(Continued)

OTHER PUBLICATIONS

Bamford M.J., et al., "Synthesis and Antiviral Activity of Some 3'-c-difluoromethyl and 3'-deoxy-3'-c-fluoromethyl Nucleosides," Journal of Medicinal Chemistry, 1990, vol. 33 (9), pp. 2488-2494.

(Continued)

*Primary Examiner* — Raymond J Henley, III

(57) ABSTRACT

The present invention features compounds effective in inhibiting active against Hepatitis C virus ("HCV") polymerase. The invention also features processes of making such compounds, compositions comprising such compounds, and methods of using such compounds to treat HCV infection.

17 Claims, No Drawings

(56) References Cited

U.S. PATENT DOCUMENTS

| | | | |
|---|---|---|---|
| 7,105,499 B2* | 9/2006 | Carroll | A61K 31/7076 514/42 |
| 7,125,855 B2* | 10/2006 | Bhat | A61K 31/7056 514/43 |
| 7,138,376 B2* | 11/2006 | Gosselin | C07H 19/056 424/228.1 |
| 7,148,206 B2* | 12/2006 | Sommadossi | A61K 31/7076 514/42 |
| 7,157,441 B2* | 1/2007 | Sommadossi | A61K 31/708 514/47 |
| 7,163,929 B2* | 1/2007 | Sommadossi | A61K 31/7076 514/25 |
| 7,169,766 B2* | 1/2007 | Sommadossi | A61K 31/708 514/49 |
| 7,192,936 B2* | 3/2007 | LaColla | A61K 31/675 514/25 |
| 7,202,224 B2* | 4/2007 | Eldrup | A61K 31/7056 514/43 |
| 7,250,416 B2* | 7/2007 | Phiasivongsa | C07D 251/16 514/241 |
| 7,307,065 B2* | 12/2007 | Schinazi | C07D 405/04 514/1 |
| 7,365,057 B2* | 4/2008 | LaColla | A61K 31/675 514/42 |
| 7,384,924 B2* | 6/2008 | LaColla | A61K 31/675 514/247 |
| 7,429,572 B2* | 9/2008 | Clark | C07H 19/00 514/49 |
| 7,547,704 B2* | 6/2009 | LaColla | A61K 31/675 514/256 |
| 7,582,748 B2* | 9/2009 | Rabi | C07H 13/08 536/1.11 |
| 7,598,373 B2* | 10/2009 | Storer | C07H 1/00 536/1.11 |
| 7,608,597 B2* | 10/2009 | Sommadossi | A61K 31/708 514/42 |
| 7,608,600 B2* | 10/2009 | Storer | A61K 31/675 514/45 |
| 7,625,875 B2* | 12/2009 | Gosselin | C07H 19/06 514/45 |
| 7,635,689 B2* | 12/2009 | LaColla | A61K 31/675 514/45 |
| 7,662,798 B2* | 2/2010 | LaColla | C07H 19/06 514/43 |
| 7,824,851 B2* | 11/2010 | Sommadossi | A61K 31/7052 435/5 |
| 7,951,787 B2* | 5/2011 | McGuigan | C07H 19/10 514/43 |
| 7,964,580 B2* | 6/2011 | Sofia | A61K 31/706 514/43 |
| 8,168,583 B2* | 5/2012 | Schinazi | C07D 405/04 514/1 |
| 8,299,038 B2* | 10/2012 | Sommadossi | A61K 31/708 514/42 |
| 8,334,270 B2* | 12/2012 | Sofia | A61K 31/706 514/43 |
| 8,343,937 B2* | 1/2013 | Sommadossi | A61K 31/7076 514/42 |
| 8,399,428 B2* | 3/2013 | Wagner | C07H 1/00 514/43 |
| 8,415,322 B2* | 4/2013 | Clark | C07H 19/00 514/49 |
| 8,481,712 B2* | 7/2013 | Bhat | C07H 19/06 536/26.2 |
| 8,580,765 B2* | 11/2013 | Sofia | A61K 31/706 514/42 |
| 8,618,076 B2* | 12/2013 | Ross | C07H 19/06 514/51 |
| 8,629,263 B2* | 1/2014 | Ross | C07H 19/10 536/25.3 |
| 8,633,309 B2* | 1/2014 | Ross | C07H 19/10 536/28.53 |
| 8,637,475 B1 | 1/2014 | Storer et al. | |
| 8,674,085 B2* | 3/2014 | Sommadossi | A61K 31/7052 435/5 |
| 8,735,372 B2 | 5/2014 | Du et al. | |
| 8,735,569 B2 | 5/2014 | Ross et al. | |
| 8,765,935 B2* | 7/2014 | Wagner | C07H 1/00 536/26.1 |
| 8,815,830 B2* | 8/2014 | Wagner | C07H 1/00 514/42 |
| 8,846,673 B2* | 9/2014 | Duan | C07D 471/04 514/234.2 |
| 8,889,159 B2* | 11/2014 | Cleary | A61K 9/2009 424/400 |
| 8,906,880 B2* | 12/2014 | Du | A61K 31/706 514/43 |
| 8,963,157 B2* | 2/2015 | Liang | H01L 21/02532 257/66 |
| 9,061,041 B2* | 6/2015 | Girijavallabhan | A61K 31/7042 |
| 9,085,573 B2* | 7/2015 | Du | A61K 31/706 |
| 9,180,138 B2* | 11/2015 | Schinazi | C07D 405/04 |
| 9,211,300 B2* | 12/2015 | Mayes | C07H 19/06 |
| 9,243,022 B2 | 1/2016 | Beigelman et al. | |
| 9,243,025 B2* | 1/2016 | Surleraux | C07H 19/167 |
| 9,284,342 B2* | 3/2016 | Ross | C07H 19/06 |
| 9,394,331 B2* | 7/2016 | Du | C07H 19/06 |
| 9,676,797 B2* | 6/2017 | Chen | C07F 9/08 |
| 2004/0110718 A1* | 6/2004 | Devos | C07H 19/06 514/45 |
| 2005/0009737 A1* | 1/2005 | Clark | C07H 19/00 514/49 |
| 2010/0316594 A1* | 12/2010 | Sommadossi | A61K 31/675 424/85.2 |
| 2012/0251487 A1* | 10/2012 | Surleraux | C07H 19/167 424/85.2 |
| 2013/0017171 A1* | 1/2013 | Sommadossi | A61K 31/708 424/85.4 |
| 2013/0149283 A1* | 6/2013 | Sommadossi | A61K 31/708 424/85.4 |
| 2013/0157971 A1* | 6/2013 | Schinazi | C07D 405/04 514/46 |
| 2013/0210757 A1 | 8/2013 | Huang et al. | |
| 2013/0310336 A1 | 11/2013 | Sommadossi et al. | |
| 2013/0315862 A1* | 11/2013 | Sommadossi | A61K 31/708 424/85.4 |
| 2013/0315863 A1* | 11/2013 | Sommadossi | A61K 31/7076 424/85.4 |
| 2014/0073606 A1* | 3/2014 | Chu | A61K 31/52 514/81 |
| 2014/0099283 A1* | 4/2014 | Gosselin | A61K 31/403 424/85.7 |
| 2014/0128339 A1* | 5/2014 | Girijavallabhan | C07H 19/06 514/51 |
| 2014/0179627 A1* | 6/2014 | Beigelman | C07H 19/16 514/47 |
| 2014/0213540 A1* | 7/2014 | Storer | A61K 31/675 514/45 |
| 2014/0219958 A1* | 8/2014 | Luly | C07H 19/10 424/85.6 |
| 2014/0286900 A1* | 9/2014 | Sommadossi | A61K 31/7052 424/85.7 |
| 2014/0309412 A1* | 10/2014 | Bhat | C07H 19/06 536/26.8 |
| 2015/0017124 A1* | 1/2015 | Storer | A61K 31/675 424/85.7 |
| 2015/0018300 A1* | 1/2015 | Du | C07H 19/06 514/47 |
| 2015/0025220 A1* | 1/2015 | Wagner | C07H 1/00 530/322 |

FOREIGN PATENT DOCUMENTS

| | | |
|---|---|---|
| WO | WO-0190121 A2 | 11/2001 |
| WO | WO-0192282 A2 | 12/2001 |
| WO | WO-0218404 A2 | 3/2002 |
| WO | WO-0232920 A2 | 4/2002 |
| WO | WO-02057425 A2 | 7/2002 |

(56) References Cited

FOREIGN PATENT DOCUMENTS

| WO | WO-03105770 A2 | 12/2003 |
|---|---|---|
| WO | WO-2004000858 A2 | 12/2003 |
| WO | WO-2005012327 A2 | 2/2005 |
| WO | WO-2006063149 A1 | 6/2006 |
| WO | WO-2006121820 A1 | 11/2006 |
| WO | WO-2008121634 A2 | 10/2008 |
| WO | WO-2010066699 A1 | 6/2010 |
| WO | WO-2011003018 A2 | 1/2011 |
| WO | WO-2012040126 A1 | 3/2012 |
| WO | WO-2012075140 A1 | 6/2012 |
| WO | WO-2012142085 A1 | 10/2012 |
| WO | WO-2014058801 A1 | 4/2014 |
| WO | WO-2014169278 A1 | 10/2014 |
| WO | WO-2014169280 A2 | 10/2014 |
| WO | WO-2014209979 A1 | 12/2014 |
| WO | WO-2015034420 A1 | 3/2015 |
| WO | WO-2015038596 A1 | 3/2015 |
| WO | WO-2015054465 A1 | 4/2015 |
| WO | WO-2015056213 A1 | 4/2015 |
| WO | WO-2015081297 A1 | 6/2015 |
| WO | WO-2015161137 A1 | 10/2015 |
| WO | WO-2015164812 A1 | 10/2015 |
| WO | WO-2016069975 A1 | 5/2016 |
| WO | WO-2016178876 A2 | 11/2016 |

OTHER PUBLICATIONS

Co-pending U.S. Appl. No. 62/155,939.
Co-pending U.S. Appl. No. 62/246,980.
Dai Q., et al., "Synthesis of 2'-c-beta-fluoromethyluridine," Organic Letters, 2003, vol. 5 (6), pp. 807-810.
Dang Q., et al., "Syntheses of Nucleosides with 2'-Spirolactam and 2'-Spiropyrrolidine Moieties as Potential Inhibitors of Hepatitis C Virus NS5B Polymerase," Tetrahedron Letters, 2014, vol. 55 (28), pp. 3813-3816.
Du J., et al., "Use of 2'-spirocyclic Ethers in HCV Nucleoside Design," Journal of Medicinal Chemistry, 2014, vol. 57 (5), pp. 1826-1835.
International Search Report and Written Opinion for Application No. mailed on PCT/US2016/049873, dated Oct. 26, 2016, 8 pages.
International Search Report and Written Opinion for Application No. PCT/US2016/018317, dated May 6, 2016, 11 pages.
International Search Report and Written Opinion for Application No. PCT/US2016/018318, dated Jul. 26, 2016, 16 pages.
International Search Report and Written Opinion for Application No. PCT/US2016/018321, dated Jul. 27, 2016, 14 pages.
International Search Report and Written Opinion for Application No. PCT/US2016/018322, dated Jul. 26, 2016, 15 pages.
International Search Report and Written Opinion for Application No. PCT/US2016/018325, dated Jul. 14, 2016, 16 pages.
International Search Report and Written Opinion for Application No. PCT/US2016/018326, dated Aug. 4, 2016, 16 pages.
International Search Report and Written Opinion for Application No. PCT/US2016/031281, dated Aug. 11, 2016, 6 pages.
International Search Report and Written Opinion for Application No. PCT/US2016/031283, dated Aug. 12, 2016, 13 pages.
International Search Report and Written Opinion for Application No. PCT/US2016/031284, dated Aug. 12, 2016, 13 pages.
International Search Report and Written Opinion for Application No. PCT/US2016/031285, dated Aug. 11, 2016, 13 pages.
International Search Report and Written Opinion for Application No. PCT/US2016/031287, dated Aug. 11, 2016, 13 pages.
International Search Report and Written Opinion for Application No. PCT/US2016/031288, dated Aug. 12, 2016, 13 pages.
Jonckers T.H., et al., "2'-deoxy-2'-spirocyclopropylcytidine Revisited: a New and Selective Inhibitor of the Hepatitis C Virus Ns5b Polymerase," Journal of Medicinal Chemistry, 2010, vol. 53 (22), pp. 8150-8160.
Kifli N., et al., "Novel Bicyclic Sugar Modified Nucleosides: Synthesis, Conformational Analysis and Antiviral Evaluation," Bioorganic & Medicinal Chemistry, 2004, vol. 12 (12), pp. 3247-3257.
Klumpp K., et al., "2'-deoxy-4'-azido Nucleoside Analogs are Highly Potent Inhibitors of Hepatitis C Virus Replication Despite the Lack of 2'-alpha-hydroxyl Groups," The Journal of Biological Chemistry, 2008, vol. 283 (4), pp. 2167-2175.
Li N.S., et al., "2'-c-branched Ribonucleosides. 2. Synthesis of 2'-c-beta-trifluoromethyl Pyrimidine Ribonucleosides," Organic Letters, 2001, vol. 3 (7), pp. 1025-1028.
Lindqvist A., et al., Preclinical Characterisation of MIV-802, a Novel Uridine Nucleotide HCV NS5B Polymerase Inhibitor, for Treatment of Hepatitis C Virus Infection, 2015, 50th International Liver Congress, Vienna, Austria.
Montgomery J.A., et al., "Nitrosoureidonucleosides," Journal of Medicinal Chemistry, 1979, vol. 22 (9), pp. 1109-1113.
Oh C.H., et al., "Design and Synthesis of Novel Carbocyclic Versions of 2'-spirocyclopropyl Ribonucleosides as Potent Anti-hcv Agents," Nucleosides, Nucleotides and Nucleic Acids, 2011, vol. 30 (6), pp. 423-439.
PCT/US2016/050048, filed on Sep. 2, 2016.
PCT/US2016/050051, filed Sep. 2, 2016.
PCT/US2016/050054, filed Sep. 2, 2016.
PCT/US2016/050055, filed Sep. 2, 2016.
PCT/US2016/050060, filed Sep. 2, 2016.
PCT/US2016/050062, filed Sep. 2, 2016.
Sasaki T., et al., "Introduction of an Azide Group Into Some Uridine Derivatives via 2',3'-benzoxonium and 2',3'-azidonium Intermediates," The Journal of Organic Chemistry, 1976, vol. 41 (19), pp. 3138-3143.
Serafinowski P.J., et al., "New Method for the Preparation of 3'- and 2'-o-phosphoramidites of 2'- and 3'-difluoromethyluridine Derivatives," Nucleosides, Nucleotides and Nucleic Acids, 2002, vol. 21 (1), pp. 1-13.
Sofia M.J., et al., "Nucleoside, Nucleotide, and Non-nucleoside Inhibitors of Hepatitis C Virus Ns5b Rna-dependent RNA-polymerase," Journal of Medicinal Chemistry, 2012, vol. 55 (6), pp. 2481-2531.
Tong W., et al., "Synthesis of New 2',3'-dideoxy-2',3'-α-fused-heterocyclic Uridines, & Some 2',3'-ene-2'-substituted Uridines From Easily Accessible 2',3'- Ene-3'phenylselenonyl Uridine," Tetrahedron, 1990, vol. 46 (8), pp. 3037-3060.
Ye J.D., et al., "Synthesis of 2'-c-difluoromethylribonucleosides and Their Enzymatic Incorporation Into Oligonucleotides," The Journal of Organic Chemistry, 2005, vol. 70 (20), pp. 7902-7910.
Yoshimura Y., et al., "Synthesis of 1-(2-deoxy-2-c-fluoromethyl-β-d-arabinofuranosyl)cytosine as a Potential Antineoplastic Agent," Bioorganic & Medicinal Chemistry Letters, 1994, vol. 4 (5), pp. 721-724.

* cited by examiner

ANTI-VIRAL COMPOUNDS

RELATED APPLICATIONS

This application is a continuation of U.S. patent application Ser. No. 15/254,342, filed Sep. 1, 2016, now U.S. Pat. No. 9,676,797, issued Jun. 13, 2017. The contents of which are incorporated herein by reference. This application also claims the benefit of priority to U.S. Provisional Application No. 62/213,378, filed Sep. 2, 2015, U.S. Provisional Application No. 62/242,136, filed Oct. 15, 2015, U.S. Provisional Application No. 62/253,426, filed Nov. 10, 2015, U.S. Provisional Application No. 62/294,449, filed Feb. 12, 2016, U.S. Provisional Application No. 62/296,801, filed Feb. 18, 2016, U.S. Provisional Application No. 62/321,538, filed Apr. 12, 2016, U.S. Provisional Application No. 62/327,087, filed Apr. 25, 2016, U.S. Provisional Application No. 62/351,038, filed Jun. 16, 2016, U.S. Provisional Application No. 62/363,640, filed Jul. 18, 2016 and U.S. Provisional Application No. 62/375,029, filed Aug. 15, 2016. The contents of each application are incorporated herein by reference.

FIELD OF THE INVENTION

The present invention relates to compounds effective in inhibiting replication of Hepatitis C virus ("HCV"). The present invention also relates to compositions comprising these compounds and methods of using these compounds to treat HCV infection.

BACKGROUND OF THE INVENTION

The HCV is an RNA virus belonging to the Hepacivirus genus in the Flaviviridae family. The enveloped HCV virion contains a positive stranded RNA genome encoding all known virus-specific proteins in a single, uninterrupted, open reading frame. The open reading frame comprises approximately 9500 nucleotides and encodes a single large polyprotein of about 3000 amino acids. The polyprotein comprises a core protein, envelope proteins E1 and E2, a membrane bound protein p7, and the non-structural proteins NS2, NS3, NS4A, NS4B, NS5A and NS5B.

Chronic HCV infection is associated with progressive liver pathology, including cirrhosis and hepatocellular carcinoma. Chronic hepatitis C may be treated with peginterferon-alpha in combination with ribavirin. Substantial limitations to efficacy and tolerability remain as many users suffer from side effects, and viral elimination from the body is often incomplete. Therefore, there is a need for new therapies to treat HCV infection.

DETAILED DESCRIPTION

In one aspect, the present invention features compounds having Formula I, and pharmaceutically acceptable salts thereof,

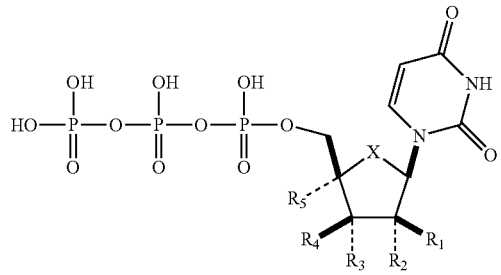

wherein for each compound of Formula I, X, $R_1$, $R_2$, $R_3$, $R_4$ and $R_5$ are as defined in Table 1:

TABLE 1

| Compound No. | X | $R_1$ | $R_2$ | $R_3$ | $R_4$ | $R_5$ |
|---|---|---|---|---|---|---|
| 1 | O | F | Cl | OH | H | $N_3$ |
| 2 | O | F | Cl | OH | H | $OCH_3$ |
| 3 | O | F | Cl | OH | H | CN |
| 4 | O | F | Cl | OH | H | 1H-imidazol-1-yl |
| 5 | O | F | Cl | OH | H | 1H-imidazol-2-yl |
| 6 | O | F | Cl | OH | H | 1H-imidazol-5-yl |
| 7 | O | F | Cl | OH | H | 1H-tetrazol-1-yl |
| 8 | O | F | Cl | OH | H | 2H-tetrazol-2-yl |
| 9 | O | F | Cl | OH | H | 1H-tetrazol-5-yl |
| 10 | O | F | Br | OH | H | H |
| 11 | O | F | Br | OH | H | D |
| 12 | O | F | Br | OH | H | F |
| 13 | O | F | Br | OH | H | $N_3$ |
| 14 | O | F | Br | OH | H | $OCH_3$ |
| 15 | O | F | Br | OH | H | CN |
| 16 | O | F | Br | OH | H | 1H-imidazol-1-yl |
| 17 | O | F | Br | OH | H | 1H-imidazol-2-yl |
| 18 | O | F | Br | OH | H | 1H-imidazol-5-yl |
| 19 | O | F | Br | OH | H | 1H-tetrazol-1-yl |
| 20 | O | F | Br | OH | H | 2H-tetrazol-2-yl |
| 21 | O | F | Br | OH | H | 1H-tetrazol-5-yl |
| 22 | O | Cl | F | OH | H | $N_3$ |
| 23 | O | Cl | F | OH | H | $OCH_3$ |
| 24 | O | Cl | F | OH | H | CN |
| 25 | O | Cl | F | OH | H | 1H-imidazol-1-yl |
| 26 | O | Cl | F | OH | H | 1H-imidazol-2-yl |
| 27 | O | Cl | F | OH | H | 1H-imidazol-5-yl |
| 28 | O | Cl | F | OH | H | 1H-tetrazol-1-yl |
| 29 | O | Cl | F | OH | H | 2H-tetrazol-2-yl |
| 30 | O | Cl | F | OH | H | 1H-tetrazol-5-yl |
| 31 | O | Cl | Cl | OH | H | $N_3$ |
| 32 | O | Cl | Cl | OH | H | $OCH_3$ |
| 33 | O | Cl | Cl | OH | H | CN |
| 34 | O | Cl | Cl | OH | H | 1H-imidazol-1-yl |
| 35 | O | Cl | Cl | OH | H | 1H-imidazol-2-yl |
| 36 | O | Cl | Cl | OH | H | 1H-imidazol-5-yl |
| 37 | O | Cl | Cl | OH | H | 1H-tetrazol-1-yl |
| 38 | O | Cl | Cl | OH | H | 2H-tetrazol-2-yl |
| 39 | O | Cl | Cl | OH | H | 1H-tetrazol-5-yl |
| 40 | O | Cl | Br | OH | H | H |
| 41 | O | Cl | Br | OH | H | D |
| 42 | O | Cl | Br | OH | H | F |
| 43 | O | Cl | Br | OH | H | $N_3$ |
| 44 | O | Cl | Br | OH | H | $OCH_3$ |
| 45 | O | Cl | Br | OH | H | CN |
| 46 | O | Cl | Br | OH | H | 1H-imidazol-1-yl |
| 47 | O | Cl | Br | OH | H | 1H-imidazol-2-yl |
| 48 | O | Cl | Br | OH | H | 1H-imidazol-5-yl |
| 49 | O | Cl | Br | OH | H | 1H-tetrazol-1-yl |
| 50 | O | Cl | Br | OH | H | 2H-tetrazol-2-yl |
| 51 | O | Cl | Br | OH | H | 1H-tetrazol-5-yl |
| 52 | O | Br | F | OH | H | H |
| 53 | O | Br | F | OH | H | D |
| 54 | O | Br | F | OH | H | F |
| 55 | O | Br | F | OH | H | $N_3$ |
| 56 | O | Br | F | OH | H | $OCH_3$ |
| 57 | O | Br | F | OH | H | CN |

TABLE 1-continued

| Compound No. | X | $R_1$ | $R_2$ | $R_3$ | $R_4$ | $R_5$ |
|---|---|---|---|---|---|---|
| 58 | O | Br | F | OH | H | 1H-imidazol-1-yl |
| 59 | O | Br | F | OH | H | 1H-imidazol-2-yl |
| 60 | O | Br | F | OH | H | 1H-imidazol-5-yl |
| 61 | O | Br | F | OH | H | 1H-tetrazol-1-yl |
| 62 | O | Br | F | OH | H | 2H-tetrazol-2-yl |
| 63 | O | Br | F | OH | H | 1H-tetrazol-5-yl |
| 64 | O | Br | Cl | OH | H | H |
| 65 | O | Br | Cl | OH | H | D |
| 66 | O | Br | Cl | OH | H | F |
| 67 | O | Br | Cl | OH | H | $N_3$ |
| 68 | O | Br | Cl | OH | H | $OCH_3$ |
| 69 | O | Br | Cl | OH | H | CN |
| 70 | O | Br | Cl | OH | H | 1H-imidazol-1-yl |
| 71 | O | Br | Cl | OH | H | 1H-imidazol-2-yl |
| 72 | O | Br | Cl | OH | H | 1H-imidazol-5-yl |
| 73 | O | Br | Cl | OH | H | 1H-tetrazol-1-yl |
| 74 | O | Br | Cl | OH | H | 2H-tetrazol-2-yl |
| 75 | O | Br | Cl | OH | H | 1H-tetrazol-5-yl |
| 76 | O | Br | Br | OH | H | H |
| 77 | O | Br | Br | OH | H | D |
| 78 | O | Br | Br | OH | H | F |
| 79 | O | Br | Br | OH | H | $N_3$ |
| 80 | O | Br | Br | OH | H | $OCH_3$ |
| 81 | O | Br | Br | OH | H | CN |
| 82 | O | Br | Br | OH | H | 1H-imidazol-1-yl |
| 83 | O | Br | Br | OH | H | 1H-imidazol-2-yl |
| 84 | O | Br | Br | OH | H | 1H-imidazol-5-yl |
| 85 | O | Br | Br | OH | H | 1H-tetrazol-1-yl |
| 86 | O | Br | Br | OH | H | 2H-tetrazol-2-yl |
| 87 | O | Br | Br | OH | H | 1H-tetrazol-5-yl |
| 88 | O | $CH_3$ | $CH_3$ | OH | H | H |
| 89 | O | $CH_3$ | $CH_3$ | OH | H | D |
| 90 | O | $CH_3$ | $CH_3$ | OH | H | F |
| 91 | O | $CH_3$ | $CH_3$ | OH | H | $N_3$ |
| 92 | O | $CH_3$ | $CH_3$ | OH | H | $OCH_3$ |
| 93 | O | $CH_3$ | $CH_3$ | OH | H | CN |
| 94 | O | $CH_3$ | $CH_3$ | OH | H | 1H-imidazol-1-yl |
| 95 | O | $CH_3$ | $CH_3$ | OH | H | 1H-imidazol-2-yl |
| 96 | O | $CH_3$ | $CH_3$ | OH | H | 1H-imidazol-5-yl |
| 97 | O | $CH_3$ | $CH_3$ | OH | H | 1H-tetrazol-1-yl |
| 98 | O | $CH_3$ | $CH_3$ | OH | H | 2H-tetrazol-2-yl |
| 99 | O | $CH_3$ | $CH_3$ | OH | H | 1H-tetrazol-5-yl |
| 100 | O | $CH_3$ | CCH | OH | H | $N_3$ |
| 101 | O | $CH_3$ | CCH | OH | H | $OCH_3$ |
| 102 | O | $CH_3$ | CCH | OH | H | CN |
| 103 | O | $CH_3$ | CCH | OH | H | 1H-imidazol-1-yl |
| 104 | O | $CH_3$ | CCH | OH | H | 1H-imidazol-2-yl |
| 105 | O | $CH_3$ | CCH | OH | H | 1H-imidazol-5-yl |
| 106 | O | $CH_3$ | CCH | OH | H | 1H-tetrazol-1-yl |
| 107 | O | $CH_3$ | CCH | OH | H | 2H-tetrazol-2-yl |
| 108 | O | $CH_3$ | CCH | OH | H | 1H-tetrazol-5-yl |
| 109 | O | F | CCH | OH | H | $N_3$ |
| 110 | O | F | CCH | OH | H | $OCH_3$ |
| 111 | O | F | CCH | OH | H | CN |
| 112 | O | F | CCH | OH | H | 1H-imidazol-1-yl |
| 113 | O | F | CCH | OH | H | 1H-imidazol-2-yl |
| 114 | O | F | CCH | OH | H | 1H-imidazol-5-yl |
| 115 | O | F | CCH | OH | H | 1H-tetrazol-1-yl |
| 116 | O | F | CCH | OH | H | 2H-tetrazol-2-yl |
| 117 | O | F | CCH | OH | H | 1H-tetrazol-5-yl |
| 118 | O | Cl | CCH | OH | H | H |
| 119 | O | Cl | CCH | OH | H | D |
| 120 | O | Cl | CCH | OH | H | F |
| 121 | O | Cl | CCH | OH | H | $N_3$ |
| 122 | O | Cl | CCH | OH | H | $OCH_3$ |
| 123 | O | Cl | CCH | OH | H | CN |
| 124 | O | Cl | CCH | OH | H | 1H-imidazol-1-yl |
| 125 | O | Cl | CCH | OH | H | 1H-imidazol-2-yl |
| 126 | O | Cl | CCH | OH | H | 1H-imidazol-5-yl |
| 127 | O | Cl | CCH | OH | H | 1H-tetrazol-1-yl |
| 128 | O | Cl | CCH | OH | H | 2H-tetrazol-2-yl |
| 129 | O | Cl | CCH | OH | H | 1H-tetrazol-5-yl |
| 130 | O | Br | CCH | OH | H | H |
| 131 | O | Br | CCH | OH | H | D |
| 132 | O | Br | CCH | OH | H | F |
| 133 | O | Br | CCH | OH | H | $N_3$ |
| 134 | O | Br | CCH | OH | H | $OCH_3$ |
| 135 | O | Br | CCH | OH | H | CN |
| 136 | O | Br | CCH | OH | H | 1H-imidazol-1-yl |
| 137 | O | Br | CCH | OH | H | 1H-imidazol-2-yl |
| 138 | O | Br | CCH | OH | H | 1H-imidazol-5-yl |
| 139 | O | Br | CCH | OH | H | 1H-tetrazol-1-yl |
| 140 | O | Br | CCH | OH | H | 2H-tetrazol-2-yl |
| 141 | O | Br | CCH | OH | H | 1H-tetrazol-5-yl |
| 142 | O | $CHF_2$ | CCH | OH | H | H |
| 143 | O | $CHF_2$ | CCH | OH | H | D |
| 144 | O | $CHF_2$ | CCH | OH | H | F |
| 145 | O | $CHF_2$ | CCH | OH | H | $N_3$ |
| 146 | O | $CHF_2$ | CCH | OH | H | $OCH_3$ |
| 147 | O | $CHF_2$ | CCH | OH | H | CN |
| 148 | O | $CHF_2$ | CCH | OH | H | 1H-imidazol-1-yl |
| 149 | O | $CHF_2$ | CCH | OH | H | 1H-imidazol-2-yl |
| 150 | O | $CHF_2$ | CCH | OH | H | 1H-imidazol-5-yl |
| 151 | O | $CHF_2$ | CCH | OH | H | 1H-tetrazol-1-yl |
| 152 | O | $CHF_2$ | CCH | OH | H | 2H-tetrazol-2-yl |
| 153 | O | $CHF_2$ | CCH | OH | H | 1H-tetrazol-5-yl |
| 154 | O | $CH_2F$ | CCH | OH | H | H |
| 155 | O | $CH_2F$ | CCH | OH | H | D |
| 156 | O | $CH_2F$ | CCH | OH | H | F |
| 157 | O | $CH_2F$ | CCH | OH | H | $N_3$ |
| 158 | O | $CH_2F$ | CCH | OH | H | $OCH_3$ |
| 159 | O | $CH_2F$ | CCH | OH | H | CN |
| 160 | O | $CH_2F$ | CCH | OH | H | 1H-imidazol-1-yl |
| 161 | O | $CH_2F$ | CCH | OH | H | 1H-imidazol-2-yl |
| 162 | O | $CH_2F$ | CCH | OH | H | 1H-imidazol-5-yl |
| 163 | O | $CH_2F$ | CCH | OH | H | 1H-tetrazol-1-yl |
| 164 | O | $CH_2F$ | CCH | OH | H | 2H-tetrazol-2-yl |
| 165 | O | $CH_2F$ | CCH | OH | H | 1H-tetrazol-5-yl |
| 166 | $C=CH_2$ | F | Cl | OH | H | $N_3$ |
| 167 | $C=CH_2$ | F | Cl | OH | H | $OCH_3$ |
| 168 | $C=CH_2$ | F | Cl | OH | H | CN |
| 169 | $C=CH_2$ | F | Cl | OH | H | 1H-imidazol-1-yl |
| 170 | $C=CH_2$ | F | Cl | OH | H | 1H-imidazol-2-yl |
| 171 | $C=CH_2$ | F | Cl | OH | H | 1H-imidazol-5-yl |
| 172 | $C=CH_2$ | F | Cl | OH | H | 1H-tetrazol-1-yl |
| 173 | $C=CH_2$ | F | Cl | OH | H | 2H-tetrazol-2-yl |
| 174 | $C=CH_2$ | F | Cl | OH | H | 1H-tetrazol-5-yl |
| 175 | $C=CH_2$ | F | Br | OH | H | H |
| 176 | $C=CH_2$ | F | Br | OH | H | D |
| 177 | $C=CH_2$ | F | Br | OH | H | F |
| 178 | $C=CH_2$ | F | Br | OH | H | $N_3$ |
| 179 | $C=CH_2$ | F | Br | OH | H | $OCH_3$ |
| 180 | $C=CH_2$ | F | Br | OH | H | CN |
| 181 | $C=CH_2$ | F | Br | OH | H | 1H-imidazol-1-yl |
| 182 | $C=CH_2$ | F | Br | OH | H | 1H-imidazol-2-yl |
| 183 | $C=CH_2$ | F | Br | OH | H | 1H-imidazol-5-yl |
| 184 | $C=CH_2$ | F | Br | OH | H | 1H-tetrazol-1-yl |
| 185 | $C=CH_2$ | F | Br | OH | H | 2H-tetrazol-2-yl |
| 186 | $C=CH_2$ | F | Br | OH | H | 1H-tetrazol-5-yl |
| 187 | $C=CH_2$ | Cl | F | OH | H | $N_3$ |
| 188 | $C=CH_2$ | Cl | F | OH | H | $OCH_3$ |
| 189 | $C=CH_2$ | Cl | F | OH | H | CN |
| 190 | $C=CH_2$ | Cl | F | OH | H | 1H-imidazol-1-yl |
| 191 | $C=CH_2$ | Cl | F | OH | H | 1H-imidazol-2-yl |
| 192 | $C=CH_2$ | Cl | F | OH | H | 1H-imidazol-5-yl |
| 193 | $C=CH_2$ | Cl | F | OH | H | 1H-tetrazol-1-yl |
| 194 | $C=CH_2$ | Cl | F | OH | H | 2H-tetrazol-2-yl |
| 195 | $C=CH_2$ | Cl | F | OH | H | 1H-tetrazol-5-yl |
| 196 | $C=CH_2$ | Cl | Cl | OH | H | $N_3$ |
| 197 | $C=CH_2$ | Cl | Cl | OH | H | $OCH_3$ |
| 198 | $C=CH_2$ | Cl | Cl | OH | H | CN |
| 199 | $C=CH_2$ | Cl | Cl | OH | H | 1H-imidazol-1-yl |
| 200 | $C=CH_2$ | Cl | Cl | OH | H | 1H-imidazol-2-yl |
| 201 | $C=CH_2$ | Cl | Cl | OH | H | 1H-imidazol-5-yl |
| 202 | $C=CH_2$ | Cl | Cl | OH | H | 1H-tetrazol-1-yl |
| 203 | $C=CH_2$ | Cl | Cl | OH | H | 2H-tetrazol-2-yl |
| 204 | $C=CH_2$ | Cl | Cl | OH | H | 1H-tetrazol-5-yl |
| 205 | $C=CH_2$ | Cl | Br | OH | H | H |
| 206 | $C=CH_2$ | Cl | Br | OH | H | D |
| 207 | $C=CH_2$ | Cl | Br | OH | H | F |
| 208 | $C=CH_2$ | Cl | Br | OH | H | $N_3$ |
| 209 | $C=CH_2$ | Cl | Br | OH | H | $OCH_3$ |
| 210 | $C=CH_2$ | Cl | Br | OH | H | CN |
| 211 | $C=CH_2$ | Cl | Br | OH | H | 1H-imidazol-1-yl |
| 212 | $C=CH_2$ | Cl | Br | OH | H | 1H-imidazol-2-yl |
| 213 | $C=CH_2$ | Cl | Br | OH | H | 1H-imidazol-5-yl |

TABLE 1-continued

| Compound No. | X | $R_1$ | $R_2$ | $R_3$ | $R_4$ | $R_5$ |
|---|---|---|---|---|---|---|
| 214 | $C=CH_2$ | Cl | Br | OH | H | 1H-tetrazol-1-yl |
| 215 | $C=CH_2$ | Cl | Br | OH | H | 2H-tetrazol-2-yl |
| 216 | $C=CH_2$ | Cl | Br | OH | H | 1H-tetrazol-5-yl |
| 217 | $C=CH_2$ | Br | F | OH | H | H |
| 218 | $C=CH_2$ | Br | F | OH | H | D |
| 219 | $C=CH_2$ | Br | F | OH | H | F |
| 220 | $C=CH_2$ | Br | F | OH | H | $N_3$ |
| 221 | $C=CH_2$ | Br | F | OH | H | $OCH_3$ |
| 222 | $C=CH_2$ | Br | F | OH | H | CN |
| 223 | $C=CH_2$ | Br | F | OH | H | 1H-imidazol-1-yl |
| 224 | $C=CH_2$ | Br | F | OH | H | 1H-imidazol-2-yl |
| 225 | $C=CH_2$ | Br | F | OH | H | 1H-imidazol-5-yl |
| 226 | $C=CH_2$ | Br | F | OH | H | 1H-tetrazol-1-yl |
| 227 | $C=CH_2$ | Br | F | OH | H | 2H-tetrazol-2-yl |
| 228 | $C=CH_2$ | Br | F | OH | H | 1H-tetrazol-5-yl |
| 229 | $C=CH_2$ | Br | Cl | OH | H | H |
| 230 | $C=CH_2$ | Br | Cl | OH | H | D |
| 231 | $C=CH_2$ | Br | Cl | OH | H | F |
| 232 | $C=CH_2$ | Br | Cl | OH | H | $N_3$ |
| 233 | $C=CH_2$ | Br | Cl | OH | H | $OCH_3$ |
| 234 | $C=CH_2$ | Br | Cl | OH | H | CN |
| 235 | $C=CH_2$ | Br | Cl | OH | H | 1H-imidazol-1-yl |
| 236 | $C=CH_2$ | Br | Cl | OH | H | 1H-imidazol-2-yl |
| 237 | $C=CH_2$ | Br | Cl | OH | H | 1H-imidazol-5-yl |
| 238 | $C=CH_2$ | Br | Cl | OH | H | 1H-tetrazol-1-yl |
| 239 | $C=CH_2$ | Br | Cl | OH | H | 2H-tetrazol-2-yl |
| 240 | $C=CH_2$ | Br | Cl | OH | H | 1H-tetrazol-5-yl |
| 241 | $C=CH_2$ | Br | Br | OH | H | H |
| 242 | $C=CH_2$ | Br | Br | OH | H | D |
| 243 | $C=CH_2$ | Br | Br | OH | H | F |
| 244 | $C=CH_2$ | Br | Br | OH | H | $N_3$ |
| 245 | $C=CH_2$ | Br | Br | OH | H | $OCH_3$ |
| 246 | $C=CH_2$ | Br | Br | OH | H | CN |
| 247 | $C=CH_2$ | Br | Br | OH | H | 1H-imidazol-1-yl |
| 248 | $C=CH_2$ | Br | Br | OH | H | 1H-imidazol-2-yl |
| 249 | $C=CH_2$ | Br | Br | OH | H | 1H-imidazol-5-yl |
| 250 | $C=CH_2$ | Br | Br | OH | H | 1H-tetrazol-1-yl |
| 251 | $C=CH_2$ | Br | Br | OH | H | 2H-tetrazol-2-yl |
| 252 | $C=CH_2$ | Br | Br | OH | H | 1H-tetrazol-5-yl |
| 253 | $C=CH_2$ | $CH_3$ | $CH_3$ | OH | H | H |
| 254 | $C=CH_2$ | $CH_3$ | $CH_3$ | OH | H | D |
| 255 | $C=CH_2$ | $CH_3$ | $CH_3$ | OH | H | F |
| 256 | $C=CH_2$ | $CH_3$ | $CH_3$ | OH | H | $N_3$ |
| 257 | $C=CH_2$ | $CH_3$ | $CH_3$ | OH | H | $OCH_3$ |
| 258 | $C=CH_2$ | $CH_3$ | $CH_3$ | OH | H | CN |
| 259 | $C=CH_2$ | $CH_3$ | $CH_3$ | OH | H | 1H-imidazol-1-yl |
| 260 | $C=CH_2$ | $CH_3$ | $CH_3$ | OH | H | 1H-imidazol-2-yl |
| 261 | $C=CH_2$ | $CH_3$ | $CH_3$ | OH | H | 1H-imidazol-5-yl |
| 262 | $C=CH_2$ | $CH_3$ | $CH_3$ | OH | H | 1H-tetrazol-1-yl |
| 263 | $C=CH_2$ | $CH_3$ | $CH_3$ | OH | H | 2H-tetrazol-2-yl |
| 264 | $C=CH_2$ | $CH_3$ | $CH_3$ | OH | H | 1H-tetrazol-5-yl |
| 265 | $C=CH_2$ | $CH_3$ | CCH | OH | H | $N_3$ |
| 266 | $C=CH_2$ | $CH_3$ | CCH | OH | H | $OCH_3$ |
| 267 | $C=CH_2$ | $CH_3$ | CCH | OH | H | CN |
| 268 | $C=CH_2$ | $CH_3$ | CCH | OH | H | 1H-imidazol-1-yl |
| 269 | $C=CH_2$ | $CH_3$ | CCH | OH | H | 1H-imidazol-2-yl |
| 270 | $C=CH_2$ | $CH_3$ | CCH | OH | H | 1H-imidazol-5-yl |
| 271 | $C=CH_2$ | $CH_3$ | CCH | OH | H | 1H-tetrazol-1-yl |
| 272 | $C=CH_2$ | $CH_3$ | CCH | OH | H | 2H-tetrazol-2-yl |
| 273 | $C=CH_2$ | $CH_3$ | CCH | OH | H | 1H-tetrazol-5-yl |
| 274 | $C=CH_2$ | F | CCH | OH | H | $N_3$ |
| 275 | $C=CH_2$ | F | CCH | OH | H | $OCH_3$ |
| 276 | $C=CH_2$ | F | CCH | OH | H | CN |
| 277 | $C=CH_2$ | F | CCH | OH | H | 1H-imidazol-1-yl |
| 278 | $C=CH_2$ | F | CCH | OH | H | 1H-imidazol-2-yl |
| 279 | $C=CH_2$ | F | CCH | OH | H | 1H-imidazol-5-yl |
| 280 | $C=CH_2$ | F | CCH | OH | H | 1H-tetrazol-1-yl |
| 281 | $C=CH_2$ | F | CCH | OH | H | 2H-tetrazol-2-yl |
| 282 | $C=CH_2$ | F | CCH | OH | H | 1H-tetrazol-5-yl |
| 283 | $C=CH_2$ | Cl | CCH | OH | H | H |
| 284 | $C=CH_2$ | Cl | CCH | OH | H | D |
| 285 | $C=CH_2$ | Cl | CCH | OH | H | F |
| 286 | $C=CH_2$ | Cl | CCH | OH | H | $N_3$ |
| 287 | $C=CH_2$ | Cl | CCH | OH | H | $OCH_3$ |
| 288 | $C=CH_2$ | Cl | CCH | OH | H | CN |
| 289 | $C=CH_2$ | Cl | CCH | OH | H | 1H-imidazol-1-yl |
| 290 | $C=CH_2$ | Cl | CCH | OH | H | 1H-imidazol-2-yl |
| 291 | $C=CH_2$ | Cl | CCH | OH | H | 1H-imidazol-5-yl |
| 292 | $C=CH_2$ | Cl | CCH | OH | H | 1H-tetrazol-1-yl |
| 293 | $C=CH_2$ | Cl | CCH | OH | H | 2H-tetrazol-2-yl |
| 294 | $C=CH_2$ | Cl | CCH | OH | H | 1H-tetrazol-5-yl |
| 295 | $C=CH_2$ | Br | CCH | OH | H | H |
| 296 | $C=CH_2$ | Br | CCH | OH | H | D |
| 297 | $C=CH_2$ | Br | CCH | OH | H | F |
| 298 | $C=CH_2$ | Br | CCH | OH | H | $N_3$ |
| 299 | $C=CH_2$ | Br | CCH | OH | H | $OCH_3$ |
| 300 | $C=CH_2$ | Br | CCH | OH | H | CN |
| 301 | $C=CH_2$ | Br | CCH | OH | H | 1H-imidazol-1-yl |
| 302 | $C=CH_2$ | Br | CCH | OH | H | 1H-imidazol-2-yl |
| 303 | $C=CH_2$ | Br | CCH | OH | H | 1H-imidazol-5-yl |
| 304 | $C=CH_2$ | Br | CCH | OH | H | 1H-tetrazol-1-yl |
| 305 | $C=CH_2$ | Br | CCH | OH | H | 2H-tetrazol-2-yl |
| 306 | $C=CH_2$ | Br | CCH | OH | H | 1H-tetrazol-5-yl |
| 307 | $C=CH_2$ | $CHF_2$ | CCH | OH | H | H |
| 308 | $C=CH_2$ | $CHF_2$ | CCH | OH | H | D |
| 309 | $C=CH_2$ | $CHF_2$ | CCH | OH | H | F |
| 310 | $C=CH_2$ | $CHF_2$ | CCH | OH | H | $N_3$ |
| 311 | $C=CH_2$ | $CHF_2$ | CCH | OH | H | $OCH_3$ |
| 312 | $C=CH_2$ | $CHF_2$ | CCH | OH | H | CN |
| 313 | $C=CH_2$ | $CHF_2$ | CCH | OH | H | 1H-imidazol-1-yl |
| 314 | $C=CH_2$ | $CHF_2$ | CCH | OH | H | 1H-imidazol-2-yl |
| 315 | $C=CH_2$ | $CHF_2$ | CCH | OH | H | 1H-imidazol-5-yl |
| 316 | $C=CH_2$ | $CHF_2$ | CCH | OH | H | 1H-tetrazol-1-yl |
| 317 | $C=CH_2$ | $CHF_2$ | CCH | OH | H | 2H-tetrazol-2-yl |
| 318 | $C=CH_2$ | $CHF_2$ | CCH | OH | H | 1H-tetrazol-5-yl |
| 319 | $C=CH_2$ | $CH_2F$ | CCH | OH | H | H |
| 320 | $C=CH_2$ | $CH_2F$ | CCH | OH | H | D |
| 321 | $C=CH_2$ | $CH_2F$ | CCH | OH | H | F |
| 322 | $C=CH_2$ | $CH_2F$ | CCH | OH | H | $N_3$ |
| 323 | $C=CH_2$ | $CH_2F$ | CCH | OH | H | $OCH_3$ |
| 324 | $C=CH_2$ | $CH_2F$ | CCH | OH | H | CN |
| 325 | $C=CH_2$ | $CH_2F$ | CCH | OH | H | 1H-imidazol-1-yl |
| 326 | $C=CH_2$ | $CH_2F$ | CCH | OH | H | 1H-imidazol-2-yl |
| 327 | $C=CH_2$ | $CH_2F$ | CCH | OH | H | 1H-imidazol-5-yl |
| 328 | $C=CH_2$ | $CH_2F$ | CCH | OH | H | 1H-tetrazol-1-yl |
| 329 | $C=CH_2$ | $CH_2F$ | CCH | OH | H | 2H-tetrazol-2-yl |
| 330 | $C=CH_2$ | $CH_2F$ | CCH | OH | H | 1H-tetrazol-5-yl |

As shown below, each compound number in Table 1 can represent compounds of different formulas but with the same X, $R_1$, $R_2$, $R_3$, $R_4$ and $R_5$ moieties.

In another aspect, the present invention features compounds having Formula II, and pharmaceutically acceptable salts thereof, as well as prodrugs thereof,

II wherein for each compound of Formula II, X, $R_1$, $R_2$, $R_3$, $R_4$ and $R_5$ are as defined in Table 1.

In still another aspect, the present invention features compounds having Formula III, and pharmaceutically acceptable salts thereof, as well as prodrugs thereof,

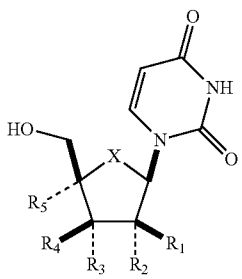

wherein for each compound of Formula III, X, $R_1$, $R_2$, $R_3$, $R_4$ and $R_5$ are as defined in Table 1.

In still another aspect, the present invention features phosphoramidate prodrugs of compounds having Formula III',

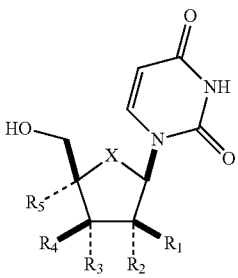

wherein for each compound of Formula III', X, $R_1$, $R_2$, $R_3$, $R_4$ and $R_5$ are as defined in Table 1.

In yet another aspect, the present invention features compounds having Formula IV,

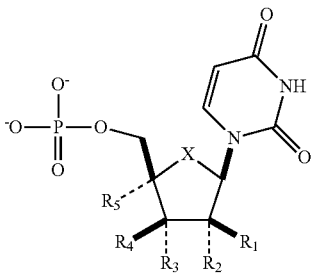

wherein for each compound of Formula IV, X, $R_1$, $R_2$, $R_3$, $R_4$ and $R_5$ are as defined in Table 1.

In yet another aspect, the present invention features compounds having Formula V,

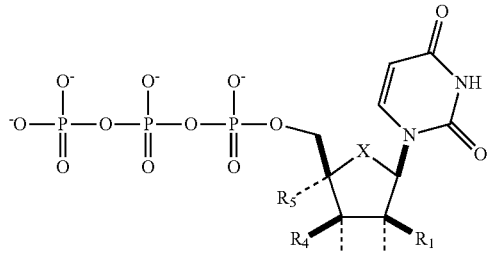

wherein for each compound of Formula V, X, $R_1$, $R_2$, $R_3$, $R_4$ and $R_5$ are as defined in Table 1.

In yet another aspect, the present invention features compounds having Formula VI, and pharmaceutically acceptable salts thereof,

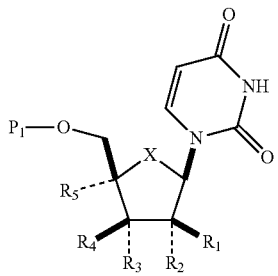

wherein for each compound of Formula VI, X, $R_1$, $R_2$, $R_3$, $R_4$ and $R_5$ are as defined in Table 1, and wherein $P_1$ is $(HO)_2P(O)$—O—$P(O)(OH)$—.

In yet another aspect, the present invention features compounds having Formula VI', and pharmaceutically acceptable salts thereof,

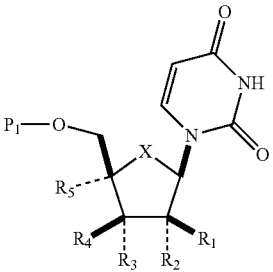

wherein for each compound of Formula VI', X, $R_1$, $R_2$, $R_3$, $R_4$ and $R_5$ are as defined in Table 1, and wherein $P_1$ is $(O^-)_2P(O)$—O—$P(O)(O^-)$—.

In yet another aspect, the present invention features compounds having Formula VI'', and pharmaceutically acceptable salts thereof,

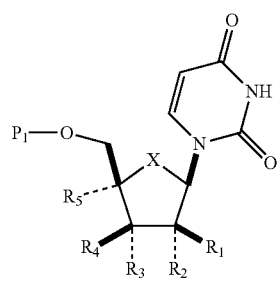

wherein for each compound of Formula VI'', X, $R_1$, $R_2$, $R_3$, $R_4$ and $R_5$ are as defined in Table 1, and wherein $P_1$ is a protected monophosphate prodrug substitution. Non-limiting examples of suitable $P_1$ for Formula VI'' can be selected from Table 2:

TABLE 2

Suitable P₁ for Formula VI″

TABLE 2-continued
Suitable P₁ for Formula VI''
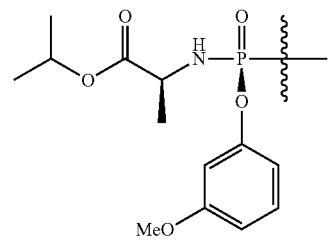 [SMILES: *[P@@](=O)(N[C@@H](C)C(=O)OC(C)C)Oc1cccc(OC)c1]
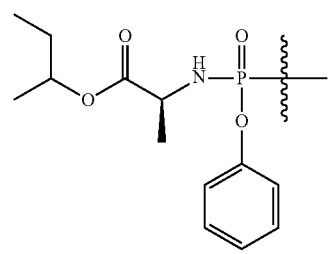 [SMILES: *P(=O)(N[C@@H](C)C(=O)OC(C)CC)Oc1ccccc1]
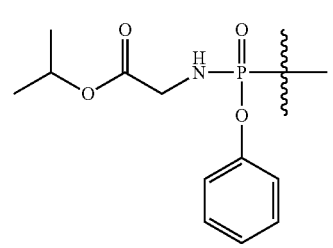 [SMILES: *P(=O)(NCC(=O)OC(C)C)Oc1ccccc1]
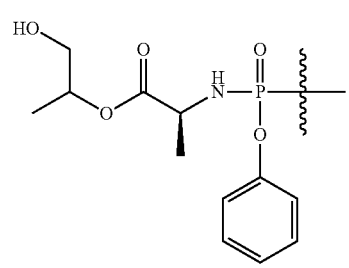 [SMILES: *P(=O)(N[C@@H](C)C(=O)OC(C)CO)Oc1ccccc1]
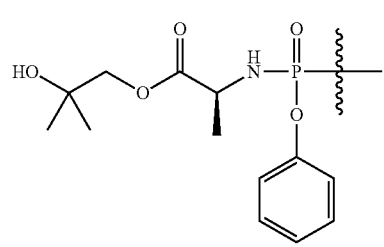 [SMILES: *P(=O)(N[C@@H](C)C(=O)OCC(C)(C)O)Oc1ccccc1]
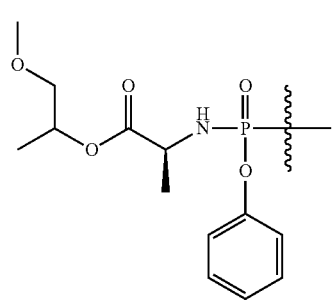 [SMILES: *P(=O)(N[C@@H](C)C(=O)OC(C)COC)Oc1ccccc1]
TABLE 2-continued
Suitable P₁ for Formula VI''
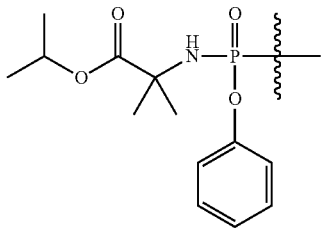 [SMILES: *P(=O)(NC(C)(C)C(=O)OC(C)C)Oc1ccccc1]
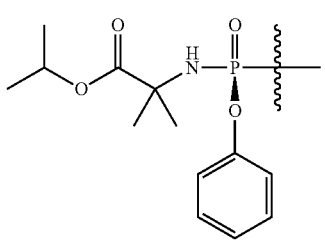 [SMILES: *[P@@](=O)(NC(C)(C)C(=O)OC(C)C)Oc1ccccc1]
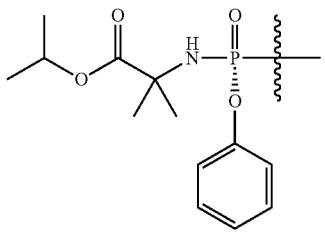 [SMILES: *[P@](=O)(NC(C)(C)C(=O)OC(C)C)Oc1ccccc1]
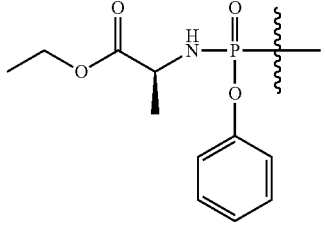 [SMILES: *P(=O)(N[C@@H](C)C(=O)OCC)Oc1ccccc1]
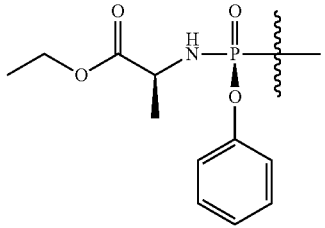 [SMILES: *[P@@](=O)(N[C@@H](C)C(=O)OCC)Oc1ccccc1]
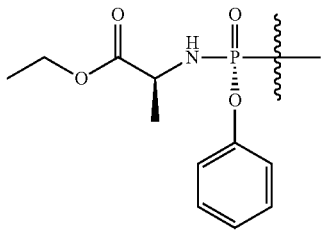 [SMILES: *[P@](=O)(N[C@@H](C)C(=O)OCC)Oc1ccccc1]

TABLE 2-continued
Suitable P₁ for Formula VI″
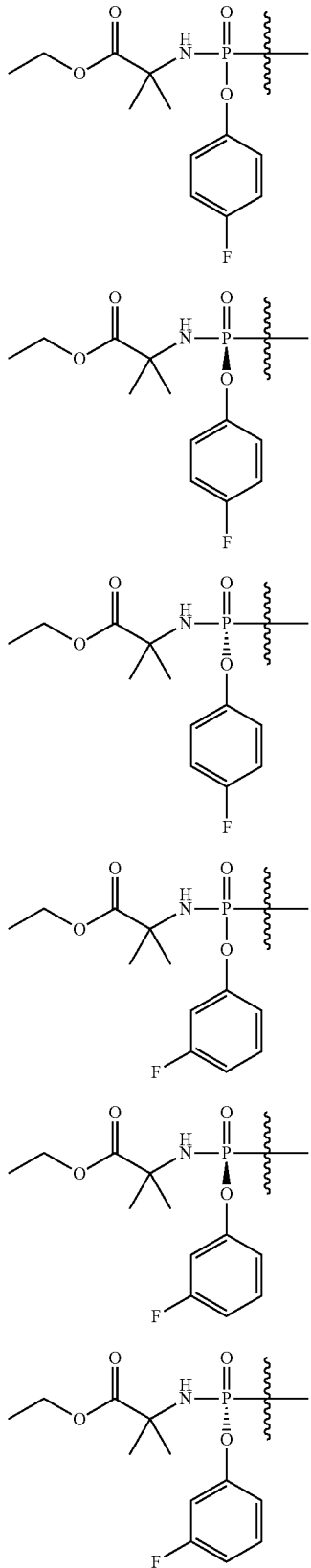
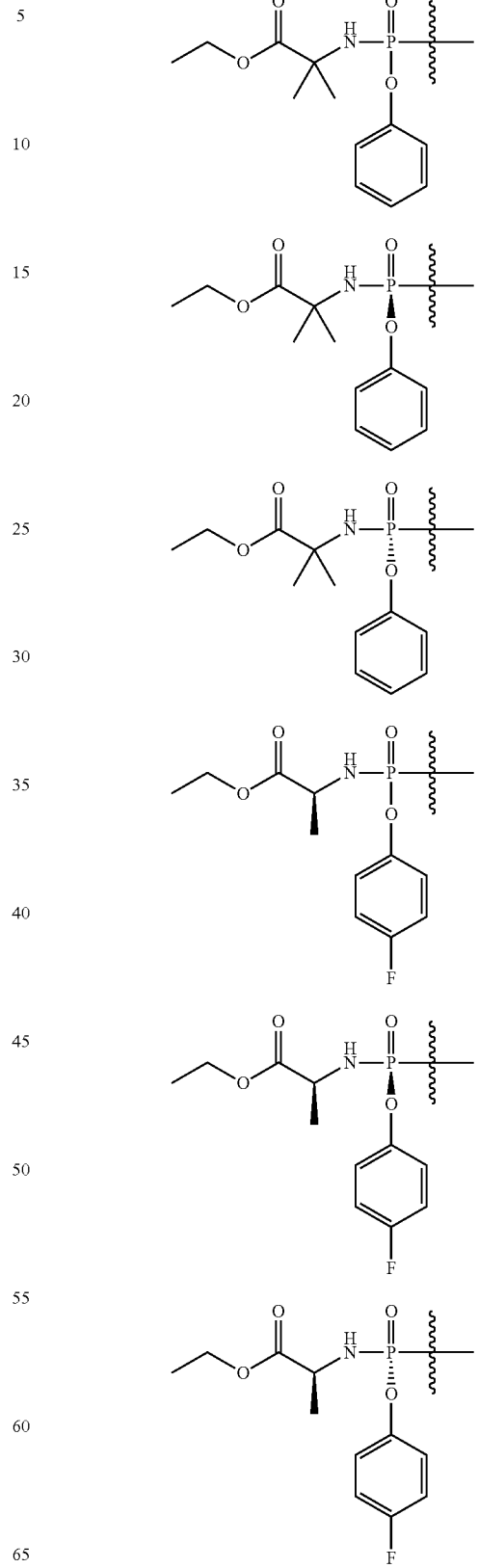

TABLE 2-continued

Suitable P₁ for Formula VI"

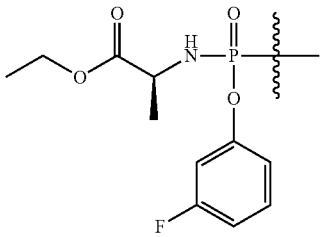 [SMILES: *P(=O)(N[C@@H](C)C(=O)OCC)Oc1cccc(F)c1]

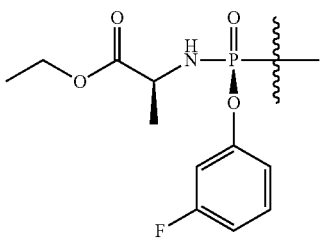 [SMILES: *[P@@](=O)(N[C@@H](C)C(=O)OCC)Oc1cccc(F)c1]

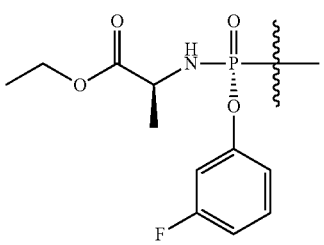

As used herein, when a moiety is selected from a list or a table, that moiety can be any one of the moieties in the list or table. For instance, if a moiety in a formula is selected from A, B or C, then the moiety in the formula can be A. For another instance, if a moiety in a formula is selected from A, B or C, then the moiety in the formula can be B. For yet another instance, if a moiety in a formula is selected from A, B or C, then the moiety in the formula can be C.

In a further aspect, the present invention features compounds having Formula VII, and pharmaceutically acceptable salts thereof,

VII

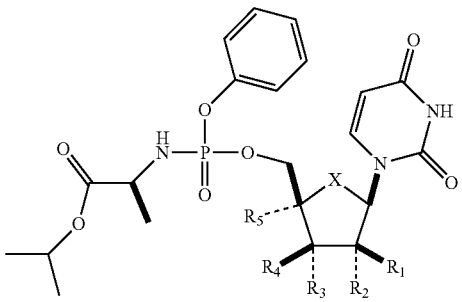

wherein for each compound of Formula VII, X, $R_1$, $R_2$, $R_3$, $R_4$ and $R_5$ are as defined in Table 1.

In a further aspect, the present invention features compounds having Formula VIII, and pharmaceutically acceptable salts thereof,

VIII

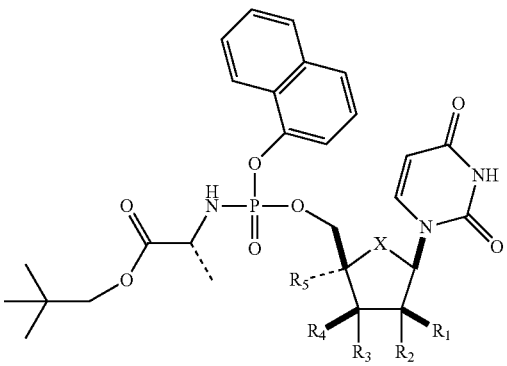

wherein for each compound of Formula VIII, X, $R_1$, $R_2$, $R_3$, $R_4$ and $R_5$ are as defined in Table 1.

In a further aspect, the present invention features compounds having Formula IX, and pharmaceutically acceptable salts thereof,

IX wherein for each compound of Formula IX, X, $R_1$, $R_2$, $R_3$, $R_4$ and $R_5$ are as defined in Table 1.

In a further aspect, the present invention features compounds having Formula A, and pharmaceutically acceptable salts thereof,

A

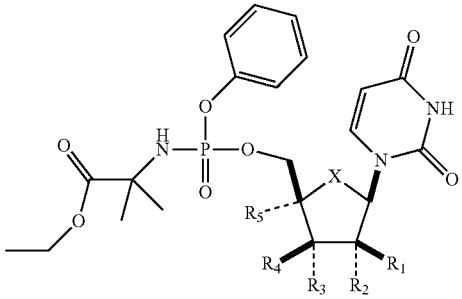

wherein for each compound of Formula A, X, $R_1$, $R_2$, $R_3$, $R_4$ and $R_5$ are as defined in Table 1. As compared to many other prodrug moieties, the prodrug moiety in Formula A can provide unexpectedly high triphosphate active levels in both human hepatocytes and dog liver.

In a further aspect, the present invention features compounds having Formula A', and pharmaceutically acceptable salts thereof,

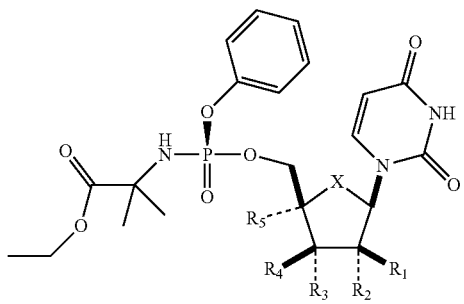

A' wherein for each compound of Formula A', X, $R_1$, $R_2$, $R_3$, $R_4$ and $R_5$ are as defined in Table 1. As compared to many other prodrug moieties, the prodrug moiety in Formula A can provide unexpectedly high triphosphate active levels in both human hepatocytes and dog liver.

In a further aspect, the present invention features compounds having Formula A", and pharmaceutically acceptable salts thereof,

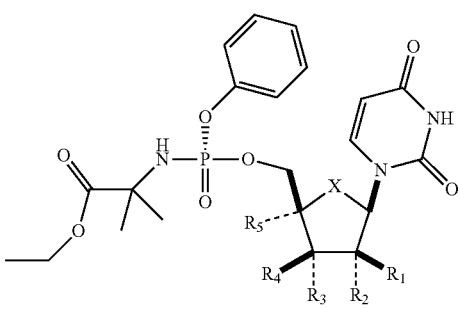

A"

wherein for each compound of Formula A", X, $R_1$, $R_2$, $R_3$, $R_4$ and $R_5$ are as defined in Table 1. As compared to many other prodrug moieties, the prodrug moiety in Formula A can provide unexpectedly high triphosphate active levels in both human hepatocytes and dog liver.

In a further aspect, the present invention features compounds having Formula B, and pharmaceutically acceptable salts thereof,

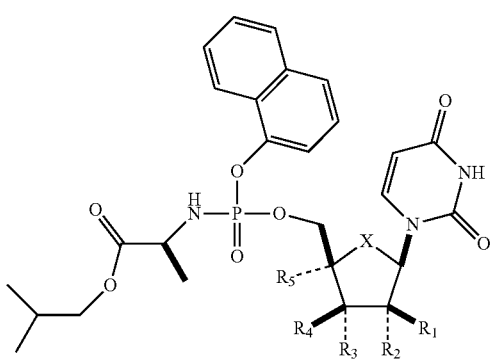

B wherein for each compound of Formula A, X, $R_1$, $R_2$, $R_3$, $R_4$ and $R_5$ are as defined in Table 1.

The present invention also features compounds with any formula described herein, wherein X, $R_1$, $R_2$, $R_3$, $R_4$ and $R_5$ moieties are as defined in Table 1, except that one Cl at $R_1$, $R_2$, $R_3$, $R_4$ or $R_5$ is replaced with Br, or preferably one Cl at $R_1$ or $R_2$ is replaced with Br.

The present invention also features compounds with any formula described herein, wherein X, $R_1$, $R_2$, $R_3$, $R_4$ and $R_5$ moieties are as defined in Table 1, except that two Cl at $R_1$, $R_2$, $R_3$, $R_4$ or $R_5$ are replaced with Br, or preferably two Cl at $R_1$ or $R_2$ are replaced with Br.

The present invention also features compounds with any formula described herein, wherein X, $R_1$, $R_2$, $R_3$, $R_4$ and $R_5$ moieties are as defined in Table 1, except that one F at $R_1$, $R_2$, $R_3$, $R_4$ or $R_5$ is replaced with Br, or preferably one F at $R_1$ or $R_2$ is replaced with Br.

The present invention also features compounds with any formula described herein, wherein X, $R_1$, $R_2$, $R_3$, $R_4$ and $R_5$ moieties are as defined in Table 1, except that two F at $R_1$, $R_2$, $R_3$, $R_4$ or $R_5$ are replaced with Br, or preferably two F at $R_1$ or $R_2$ are replaced with Br.

The present invention also features compounds with any formula described herein, wherein X, $R_1$, $R_2$, $R_3$, $R_4$ and $R_5$ moieties are as defined in Table 1, except that $R_3$ is

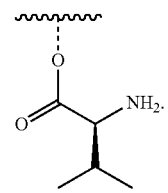

The present invention also features compounds with any formula described herein, wherein X, $R_1$, $R_2$, $R_3$, $R_4$ and $R_5$ moieties are as defined in Table 1, except that $R_3$ is

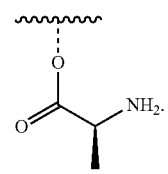

In another aspect, the present invention features Compound No. 52 according to Table 1, wherein the compound has Formula I. The compound according to this aspect of the invention is expected to have significantly improved permeability as compared to compounds in which Br is replaced with Cl.

In another aspect, the present invention features Compound No. 52 according to Table 1, wherein the compound has Formula II. The compound according to this aspect of the invention is expected to have significantly improved permeability as compared to compounds in which Br is replaced with Cl.

In another aspect, the present invention features Compound No. 52 according to Table 1, wherein the compound has Formula III. The compound according to this aspect of the invention is expected to have significantly improved permeability as compared to compounds in which Br is replaced with Cl.

In another aspect, the present invention features Compound No. 52 according to Table 1, wherein the compound has Formula III'. The compound according to this aspect of the invention is expected to have significantly improved permeability as compared to compounds in which Br is replaced with Cl.

In another aspect, the present invention features Compound No. 52 according to Table 1, wherein the compound has Formula IV. The compound according to this aspect of the invention is expected to have significantly improved permeability as compared to compounds in which Br is replaced with Cl.

In another aspect, the present invention features Compound No. 52 according to Table 1, wherein the compound has Formula V. The compound according to this aspect of the invention is expected to have significantly improved permeability as compared to compounds in which Br is replaced with Cl.

In another aspect, the present invention features Compound No. 52 according to Table 1, wherein the compound has Formula VI. The compound according to this aspect of the invention is expected to have significantly improved permeability as compared to compounds in which Br is replaced with Cl.

In another aspect, the present invention features Compound No. 52 according to Table 1, wherein the compound has Formula VI'. The compound according to this aspect of the invention is expected to have significantly improved permeability as compared to compounds in which Br is replaced with Cl.

In another aspect, the present invention features Compound No. 52 according to Table 1, wherein the compound has Formula VI". The compound according to this aspect of the invention is expected to have significantly improved permeability as compared to compounds in which Br is replaced with Cl.

In another aspect, the present invention features Compound No. 52 according to Table 1, wherein the compound has Formula VII. The compound according to this aspect of the invention is expected to have significantly improved permeability as compared to compounds in which Br is replaced with Cl.

In another aspect, the present invention features Compound No. 52 according to Table 1, wherein the compound has Formula VIII. The compound according to this aspect of the invention is expected to have significantly improved permeability as compared to compounds in which Br is replaced with Cl.

In another aspect, the present invention features Compound No. 52 according to Table 1, wherein the compound has Formula IX. The compound according to this aspect of the invention is expected to have significantly improved permeability as compared to compounds in which Br is replaced with Cl.

In another aspect, the present invention features Compound No. 52 according to Table 1, wherein the compound has Formula A. The compound according to this aspect of the invention is expected to have significantly improved permeability as compared to compounds in which Br is replaced with Cl.

In another aspect, the present invention features Compound No. 52 according to Table 1, wherein the compound has Formula A'. The compound according to this aspect of the invention is expected to have significantly improved permeability as compared to compounds in which Br is replaced with Cl.

In another aspect, the present invention features Compound No. 52 according to Table 1, wherein the compound has Formula A". The compound according to this aspect of the invention is expected to have significantly improved permeability as compared to compounds in which Br is replaced with Cl.

In another aspect, the present invention features Compound No. 52 according to Table 1, wherein the compound has Formula B. The compound according to this aspect of the invention is expected to have significantly improved permeability as compared to compounds in which Br is replaced with Cl.

In another aspect, the present invention features Compound No. 64 according to Table 1, wherein the compound has Formula I. The compound according to this aspect of the invention is expected to have significantly improved permeability as compared to compounds in which Br is replaced with Cl.

In another aspect, the present invention features Compound No. 64 according to Table 1, wherein the compound has Formula II. The compound according to this aspect of the invention is expected to have significantly improved permeability as compared to compounds in which Br is replaced with Cl.

In another aspect, the present invention features Compound No. 64 according to Table 1, wherein the compound has Formula III. The compound according to this aspect of the invention is expected to have significantly improved permeability as compared to compounds in which Br is replaced with Cl.

In another aspect, the present invention features Compound No. 64 according to Table 1, wherein the compound has Formula III'. The compound according to this aspect of the invention is expected to have significantly improved permeability as compared to compounds in which Br is replaced with Cl.

In another aspect, the present invention features Compound No. 64 according to Table 1, wherein the compound has Formula IV. The compound according to this aspect of the invention is expected to have significantly improved permeability as compared to compounds in which Br is replaced with Cl.

In another aspect, the present invention features Compound No. 64 according to Table 1, wherein the compound has Formula V. The compound according to this aspect of the invention is expected to have significantly improved permeability as compared to compounds in which Br is replaced with Cl.

In another aspect, the present invention features Compound No. 64 according to Table 1, wherein the compound has Formula VI. The compound according to this aspect of the invention is expected to have significantly improved permeability as compared to compounds in which Br is replaced with Cl.

In another aspect, the present invention features Compound No. 64 according to Table 1, wherein the compound has Formula VI'. The compound according to this aspect of the invention is expected to have significantly improved permeability as compared to compounds in which Br is replaced with Cl.

In another aspect, the present invention features Compound No. 64 according to Table 1, wherein the compound has Formula VI". The compound according to this aspect of the invention is expected to have significantly improved permeability as compared to compounds in which Br is replaced with Cl.

In another aspect, the present invention features Compound No. 64 according to Table 1, wherein the compound has Formula VII. The compound according to this aspect of the invention is expected to have significantly improved permeability as compared to compounds in which Br is replaced with Cl.

In another aspect, the present invention features Compound No. 64 according to Table 1, wherein the compound has Formula VIII. The compound according to this aspect of the invention is expected to have significantly improved permeability as compared to compounds in which Br is replaced with Cl.

In another aspect, the present invention features Compound No. 64 according to Table 1, wherein the compound has Formula IX. The compound according to this aspect of the invention is expected to have significantly improved permeability as compared to compounds in which Br is replaced with Cl.

In another aspect, the present invention features Compound No. 64 according to Table 1, wherein the compound has Formula A. The compound according to this aspect of the invention is expected to have significantly improved permeability as compared to compounds in which Br is replaced with Cl.

In another aspect, the present invention features Compound No. 64 according to Table 1, wherein the compound has Formula A'. The compound according to this aspect of the invention is expected to have significantly improved permeability as compared to compounds in which Br is replaced with Cl.

In another aspect, the present invention features Compound No. 64 according to Table 1, wherein the compound has Formula A". The compound according to this aspect of the invention is expected to have significantly improved permeability as compared to compounds in which Br is replaced with Cl.

In another aspect, the present invention features Compound No. 64 according to Table 1, wherein the compound has Formula B. The compound according to this aspect of the invention is expected to have significantly improved permeability as compared to compounds in which Br is replaced with Cl.

In another aspect, the present invention features Compound No. 40 according to Table 1, wherein the compound has Formula I. The compound according to this aspect of the invention is expected to have significantly improved permeability as compared to compounds in which Br is replaced with Cl.

In another aspect, the present invention features Compound No. 40 according to Table 1, wherein the compound has Formula II. The compound according to this aspect of the invention is expected to have significantly improved permeability as compared to compounds in which Br is replaced with Cl.

In another aspect, the present invention features Compound No. 40 according to Table 1, wherein the compound has Formula III. The compound according to this aspect of the invention is expected to have significantly improved permeability as compared to compounds in which Br is replaced with Cl.

In another aspect, the present invention features Compound No. 40 according to Table 1, wherein the compound has Formula III'. The compound according to this aspect of the invention is expected to have significantly improved permeability as compared to compounds in which Br is replaced with Cl.

In another aspect, the present invention features Compound No. 40 according to Table 1, wherein the compound has Formula IV. The compound according to this aspect of the invention is expected to have significantly improved permeability as compared to compounds in which Br is replaced with Cl.

In another aspect, the present invention features Compound No. 40 according to Table 1, wherein the compound has Formula V. The compound according to this aspect of the invention is expected to have significantly improved permeability as compared to compounds in which Br is replaced with Cl.

In another aspect, the present invention features Compound No. 40 according to Table 1, wherein the compound has Formula VI. The compound according to this aspect of the invention is expected to have significantly improved permeability as compared to compounds in which Br is replaced with Cl.

In another aspect, the present invention features Compound No. 40 according to Table 1, wherein the compound has Formula VI'. The compound according to this aspect of the invention is expected to have significantly improved permeability as compared to compounds in which Br is replaced with Cl.

In another aspect, the present invention features Compound No. 40 according to Table 1, wherein the compound has Formula VI". The compound according to this aspect of the invention is expected to have significantly improved permeability as compared to compounds in which Br is replaced with Cl.

In another aspect, the present invention features Compound No. 40 according to Table 1, wherein the compound has Formula VII. The compound according to this aspect of the invention is expected to have significantly improved permeability as compared to compounds in which Br is replaced with Cl.

In another aspect, the present invention features Compound No. 40 according to Table 1, wherein the compound has Formula VIII. The compound according to this aspect of the invention is expected to have significantly improved permeability as compared to compounds in which Br is replaced with Cl.

In another aspect, the present invention features Compound No. 40 according to Table 1, wherein the compound has Formula IX. The compound according to this aspect of the invention is expected to have significantly improved permeability as compared to compounds in which Br is replaced with Cl.

In another aspect, the present invention features Compound No. 40 according to Table 1, wherein the compound has Formula A. The compound according to this aspect of the invention is expected to have significantly improved permeability as compared to compounds in which Br is replaced with Cl.

In another aspect, the present invention features Compound No. 40 according to Table 1, wherein the compound has Formula A'. The compound according to this aspect of the invention is expected to have significantly improved permeability as compared to compounds in which Br is replaced with Cl.

In another aspect, the present invention features Compound No. 40 according to Table 1, wherein the compound has Formula A". The compound according to this aspect of the invention is expected to have significantly improved permeability as compared to compounds in which Br is replaced with Cl.

In another aspect, the present invention features Compound No. 40 according to Table 1, wherein the compound has Formula B. The compound according to this aspect of the invention is expected to have significantly improved permeability as compared to compounds in which Br is replaced with Cl.

In another aspect, the present invention features Compound No. 35 according to Table 1, wherein the compound has Formula I.

In another aspect, the present invention features Compound No. 35 according to Table 1, wherein the compound has Formula II.

In another aspect, the present invention features Compound No. 35 according to Table 1, wherein the compound has Formula III.

In another aspect, the present invention features Compound No. 35 according to Table 1, wherein the compound has Formula III'.

In another aspect, the present invention features Compound No. 35 according to Table 1, wherein the compound has Formula IV.

In another aspect, the present invention features Compound No. 35 according to Table 1, wherein the compound has Formula V.

In another aspect, the present invention features Compound No. 35 according to Table 1, wherein the compound has Formula VI.

In another aspect, the present invention features Compound No. 35 according to Table 1, wherein the compound has Formula VI'.

In another aspect, the present invention features Compound No. 35 according to Table 1, wherein the compound has Formula VI".

In another aspect, the present invention features Compound No. 35 according to Table 1, wherein the compound has Formula VII.

In another aspect, the present invention features Compound No. 35 according to Table 1, wherein the compound has Formula VIII.

In another aspect, the present invention features Compound No. 35 according to Table 1, wherein the compound has Formula IX.

In another aspect, the present invention features Compound No. 35 according to Table 1, wherein the compound has Formula A.

In another aspect, the present invention features Compound No. 35 according to Table 1, wherein the compound has Formula A'.

In another aspect, the present invention features Compound No. 35 according to Table 1, wherein the compound has Formula A".

In another aspect, the present invention features Compound No. 35 according to Table 1, wherein the compound has Formula B.

In another aspect, the present invention features Compound No. 43 according to Table 1, wherein the compound has Formula I.

In another aspect, the present invention features Compound No. 43 according to Table 1, wherein the compound has Formula II.

In another aspect, the present invention features Compound No. 43 according to Table 1, wherein the compound has Formula III.

In another aspect, the present invention features Compound No. 43 according to Table 1, wherein the compound has Formula III'.

In another aspect, the present invention features Compound No. 43 according to Table 1, wherein the compound has Formula IV.

In another aspect, the present invention features Compound No. 43 according to Table 1, wherein the compound has Formula V.

In another aspect, the present invention features Compound No. 43 according to Table 1, wherein the compound has Formula VI.

In another aspect, the present invention features Compound No. 43 according to Table 1, wherein the compound has Formula VI'.

In another aspect, the present invention features Compound No. 43 according to Table 1, wherein the compound has Formula VI".

In another aspect, the present invention features Compound No. 43 according to Table 1, wherein the compound has Formula VII.

In another aspect, the present invention features Compound No. 43 according to Table 1, wherein the compound has Formula VIII.

In another aspect, the present invention features Compound No. 43 according to Table 1, wherein the compound has Formula IX.

In another aspect, the present invention features Compound No. 43 according to Table 1, wherein the compound has Formula A.

In another aspect, the present invention features Compound No. 43 according to Table 1, wherein the compound has Formula A'.

In another aspect, the present invention features Compound No. 43 according to Table 1, wherein the compound has Formula A".

In another aspect, the present invention features Compound No. 43 according to Table 1, wherein the compound has Formula B.

In another aspect, the present invention features Compound No. 47 according to Table 1, wherein the compound has Formula I.

In another aspect, the present invention features Compound No. 47 according to Table 1, wherein the compound has Formula II.

In another aspect, the present invention features Compound No. 47 according to Table 1, wherein the compound has Formula III.

In another aspect, the present invention features Compound No. 47 according to Table 1, wherein the compound has Formula III'.

In another aspect, the present invention features Compound No. 47 according to Table 1, wherein the compound has Formula IV.

In another aspect, the present invention features Compound No. 47 according to Table 1, wherein the compound has Formula V.

In another aspect, the present invention features Compound No. 47 according to Table 1, wherein the compound has Formula VI.

In another aspect, the present invention features Compound No. 47 according to Table 1, wherein the compound has Formula VI'.

In another aspect, the present invention features Compound No. 47 according to Table 1, wherein the compound has Formula VI".

In another aspect, the present invention features Compound No. 47 according to Table 1, wherein the compound has Formula VII.

In another aspect, the present invention features Compound No. 47 according to Table 1, wherein the compound has Formula VIII.

In another aspect, the present invention features Compound No. 47 according to Table 1, wherein the compound has Formula IX.

In another aspect, the present invention features Compound No. 47 according to Table 1, wherein the compound has Formula A.

In another aspect, the present invention features Compound No. 47 according to Table 1, wherein the compound has Formula A'.

In another aspect, the present invention features Compound No. 47 according to Table 1, wherein the compound has Formula A".

In another aspect, the present invention features Compound No. 47 according to Table 1, wherein the compound has Formula B.

In another aspect, the present invention features Compound No. 59 according to Table 1, wherein the compound has Formula I.

In another aspect, the present invention features Compound No. 59 according to Table 1, wherein the compound has Formula II.

In another aspect, the present invention features Compound No. 59 according to Table 1, wherein the compound has Formula III.

In another aspect, the present invention features Compound No. 59 according to Table 1, wherein the compound has Formula III'.

In another aspect, the present invention features Compound No. 59 according to Table 1, wherein the compound has Formula IV.

In another aspect, the present invention features Compound No. 59 according to Table 1, wherein the compound has Formula V.

In another aspect, the present invention features Compound No. 59 according to Table 1, wherein the compound has Formula VI.

In another aspect, the present invention features Compound No. 59 according to Table 1, wherein the compound has Formula VI'.

In another aspect, the present invention features Compound No. 59 according to Table 1, wherein the compound has Formula VI".

In another aspect, the present invention features Compound No. 59 according to Table 1, wherein the compound has Formula VII.

In another aspect, the present invention features Compound No. 59 according to Table 1, wherein the compound has Formula VIII.

In another aspect, the present invention features Compound No. 59 according to Table 1, wherein the compound has Formula IX.

In another aspect, the present invention features Compound No. 59 according to Table 1, wherein the compound has Formula A.

In another aspect, the present invention features Compound No. 59 according to Table 1, wherein the compound has Formula A'.

In another aspect, the present invention features Compound No. 59 according to Table 1, wherein the compound has Formula A".

In another aspect, the present invention features Compound No. 59 according to Table 1, wherein the compound has Formula B.

In another aspect, the present invention features Compound No. 215 according to Table 1, wherein the compound has Formula I. The compound according to this aspect of the invention is expected to have significantly improved permeability as compared to compounds in which Br is replaced with Cl.

In another aspect, the present invention features Compound No. 215 according to Table 1, wherein the compound has Formula II. The compound according to this aspect of the invention is expected to have significantly improved permeability as compared to compounds in which Br is replaced with Cl.

In another aspect, the present invention features Compound No. 215 according to Table 1, wherein the compound has Formula III. The compound according to this aspect of the invention is expected to have significantly improved permeability as compared to compounds in which Br is replaced with Cl.

In another aspect, the present invention features Compound No. 215 according to Table 1, wherein the compound has Formula III'. The compound according to this aspect of the invention is expected to have significantly improved permeability as compared to compounds in which Br is replaced with Cl.

In another aspect, the present invention features Compound No. 215 according to Table 1, wherein the compound has Formula IV. The compound according to this aspect of the invention is expected to have significantly improved permeability as compared to compounds in which Br is replaced with Cl.

In another aspect, the present invention features Compound No. 215 according to Table 1, wherein the compound has Formula V. The compound according to this aspect of the invention is expected to have significantly improved permeability as compared to compounds in which Br is replaced with Cl.

In another aspect, the present invention features Compound No. 215 according to Table 1, wherein the compound has Formula VI. The compound according to this aspect of the invention is expected to have significantly improved permeability as compared to compounds in which Br is replaced with Cl.

In another aspect, the present invention features Compound No. 215 according to Table 1, wherein the compound has Formula VI'. The compound according to this aspect of the invention is expected to have significantly improved permeability as compared to compounds in which Br is replaced with Cl.

In another aspect, the present invention features Compound No. 215 according to Table 1, wherein the compound has Formula VI". The compound according to this aspect of the invention is expected to have significantly improved permeability as compared to compounds in which Br is replaced with Cl.

In another aspect, the present invention features Compound No. 215 according to Table 1, wherein the compound has Formula VII. The compound according to this aspect of the invention is expected to have significantly improved permeability as compared to compounds in which Br is replaced with Cl.

In another aspect, the present invention features Compound No. 215 according to Table 1, wherein the compound has Formula VIII. The compound according to this aspect of the invention is expected to have significantly improved permeability as compared to compounds in which Br is replaced with Cl.

In another aspect, the present invention features Compound No. 215 according to Table 1, wherein the compound has Formula IX. The compound according to this aspect of the invention is expected to have significantly improved permeability as compared to compounds in which Br is replaced with Cl.

In another aspect, the present invention features Compound No. 215 according to Table 1, wherein the compound has Formula A. The compound according to this aspect of the invention is expected to have significantly improved permeability as compared to compounds in which Br is replaced with Cl.

In another aspect, the present invention features Compound No. 215 according to Table 1, wherein the compound has Formula A'. The compound according to this aspect of the invention is expected to have significantly improved permeability as compared to compounds in which Br is replaced with Cl.

In another aspect, the present invention features Compound No. 215 according to Table 1, wherein the compound has Formula A". The compound according to this aspect of the invention is expected to have significantly improved permeability as compared to compounds in which Br is replaced with Cl.

In another aspect, the present invention features Compound No. 215 according to Table 1, wherein the compound has Formula B. The compound according to this aspect of the invention is expected to have significantly improved permeability as compared to compounds in which Br is replaced with Cl.

In another aspect, the present invention features Compound No. 216 according to Table 1, wherein the compound has Formula I. The compound according to this aspect of the invention is expected to have significantly improved permeability as compared to compounds in which Br is replaced with Cl.

In another aspect, the present invention features Compound No. 216 according to Table 1, wherein the compound has Formula II. The compound according to this aspect of the invention is expected to have significantly improved permeability as compared to compounds in which Br is replaced with Cl.

In another aspect, the present invention features Compound No. 216 according to Table 1, wherein the compound has Formula III. The compound according to this aspect of the invention is expected to have significantly improved permeability as compared to compounds in which Br is replaced with Cl.

In another aspect, the present invention features Compound No. 216 according to Table 1, wherein the compound has Formula III'. The compound according to this aspect of the invention is expected to have significantly improved permeability as compared to compounds in which Br is replaced with Cl.

In another aspect, the present invention features Compound No. 216 according to Table 1, wherein the compound has Formula IV. The compound according to this aspect of the invention is expected to have significantly improved permeability as compared to compounds in which Br is replaced with Cl.

In another aspect, the present invention features Compound No. 216 according to Table 1, wherein the compound has Formula V. The compound according to this aspect of the invention is expected to have significantly improved permeability as compared to compounds in which Br is replaced with Cl.

In another aspect, the present invention features Compound No. 216 according to Table 1, wherein the compound has Formula VI. The compound according to this aspect of the invention is expected to have significantly improved permeability as compared to compounds in which Br is replaced with Cl.

In another aspect, the present invention features Compound No. 216 according to Table 1, wherein the compound has Formula VI'. The compound according to this aspect of the invention is expected to have significantly improved permeability as compared to compounds in which Br is replaced with Cl.

In another aspect, the present invention features Compound No. 216 according to Table 1, wherein the compound has Formula VI". The compound according to this aspect of the invention is expected to have significantly improved permeability as compared to compounds in which Br is replaced with Cl.

In another aspect, the present invention features Compound No. 216 according to Table 1, wherein the compound has Formula VII. The compound according to this aspect of the invention is expected to have significantly improved permeability as compared to compounds in which Br is replaced with Cl.

In another aspect, the present invention features Compound No. 216 according to Table 1, wherein the compound has Formula VIII. The compound according to this aspect of the invention is expected to have significantly improved permeability as compared to compounds in which Br is replaced with Cl.

In another aspect, the present invention features Compound No. 216 according to Table 1, wherein the compound has Formula IX. The compound according to this aspect of the invention is expected to have significantly improved permeability as compared to compounds in which Br is replaced with Cl.

In another aspect, the present invention features Compound No. 216 according to Table 1, wherein the compound has Formula A. The compound according to this aspect of the invention is expected to have significantly improved permeability as compared to compounds in which Br is replaced with Cl.

In another aspect, the present invention features Compound No. 216 according to Table 1, wherein the compound has Formula A'. The compound according to this aspect of the invention is expected to have significantly improved permeability as compared to compounds in which Br is replaced with Cl.

In another aspect, the present invention features Compound No. 216 according to Table 1, wherein the compound has Formula A". The compound according to this aspect of the invention is expected to have significantly improved permeability as compared to compounds in which Br is replaced with Cl.

In another aspect, the present invention features Compound No. 216 according to Table 1, wherein the compound has Formula B. The compound according to this aspect of the invention is expected to have significantly improved permeability as compared to compounds in which Br is replaced with Cl.

Likewise, in another aspect, the present invention features Compound No. 1 according to Table 1, wherein the compound has Formula I, II, III, III', IV, V, VI, VI', VI", VII, VIII, IX, A, A', A" or B.

Likewise, in another aspect, the present invention features Compound No. 2 according to Table 1, wherein the compound has Formula I, II, III, III', IV, V, VI, VI', VI", VII, VIII, IX, A, A', A" or B.

Likewise, in another aspect, the present invention features Compound No. 9 according to Table 1, wherein the compound has Formula I, II, III, III', IV, V, VI, VI', VI", VII, VIII, IX, A, A', A" or B.

Likewise, in another aspect, the present invention features Compound No. 10 according to Table 1, wherein the compound has Formula I, II, III, III', IV, V, VI, VI', VI", VII, VIII, IX, A, A', A" or B.

Likewise, in another aspect, the present invention features Compound No. 127 according to Table 1, wherein the compound has Formula I, II, III, III', IV, V, VI, VI', VI", VII, VIII, IX, A, A', A" or B.

Likewise, in another aspect, the present invention features Compound No. 128 according to Table 1, wherein the compound has Formula I, II, III, III', IV, V, VI, VI', VI", VII, VIII, IX, A, A', A" or B.

Likewise, in another aspect, the present invention features Compound No. 129 according to Table 1, wherein the compound has Formula I, II, III, III', IV, V, VI, VI', VI", VII, VIII, IX, A, A', A" or B.

Likewise, in another aspect, the present invention features Compound No. 130 according to Table 1, wherein the compound has Formula I, II, III, III', IV, V, VI, VI', VI", VII, VIII, IX, A, A', A" or B.

Likewise, in another aspect, the present invention features Compound No. 11 according to Table 1, wherein the compound has Formula I, II, III, III', IV, V, VI, VI', VI", VII, VIII, IX, A, A', A" or B.

Likewise, in another aspect, the present invention features Compound No. 12 according to Table 1, wherein the compound has Formula I, II, III, III', IV, V, VI, VI', VI", VII, VIII, IX, A, A', A" or B.

Likewise, in another aspect, the present invention features Compound No. 13 according to Table 1, wherein the compound has Formula I, II, III, III', IV, V, VI, VI', VI", VII, VIII, IX, A, A', A" or B.

Likewise, in another aspect, the present invention features Compound No. 14 according to Table 1, wherein the compound has Formula I, II, III, III', IV, V, VI, VI', VI", VII, VIII, IX, A, A', A" or B.

Likewise, in another aspect, the present invention features Compound No. 131 according to Table 1, wherein the compound has Formula I, II, III, III', IV, V, VI, VI', VI", VII, VIII, IX, A, A', A" or B.

Likewise, in another aspect, the present invention features Compound No. 132 according to Table 1, wherein the compound has Formula I, II, III, III', IV, V, VI, VI', VI", VII, VIII, IX, A, A', A" or B.

Likewise, in another aspect, the present invention features Compound No. 133 according to Table 1, wherein the compound has Formula I, II, III, III', IV, V, VI, VI', VI", VII, VIII, IX, A, A', A" or B.

Likewise, in another aspect, the present invention features Compound No. 134 according to Table 1, wherein the compound has Formula I, II, III, III', IV, V, VI, VI', VI", VII, VIII, IX, A, A', A" or B.

In yet another embodiment, the present invention features a compound selected from Table 3. Some of the compounds in Table 3 showed significantly improved intracellular triphosphate drug concentrations in replicon wash-out experiments, as compared to the compound of Example 1. For the replicon wash-out experiments, cells were incubated for 4 hours with the prodrug, and the concentration of the triphosphate drug in the cells was measured at 24-hour.

TABLE 3

Exemplary Compounds

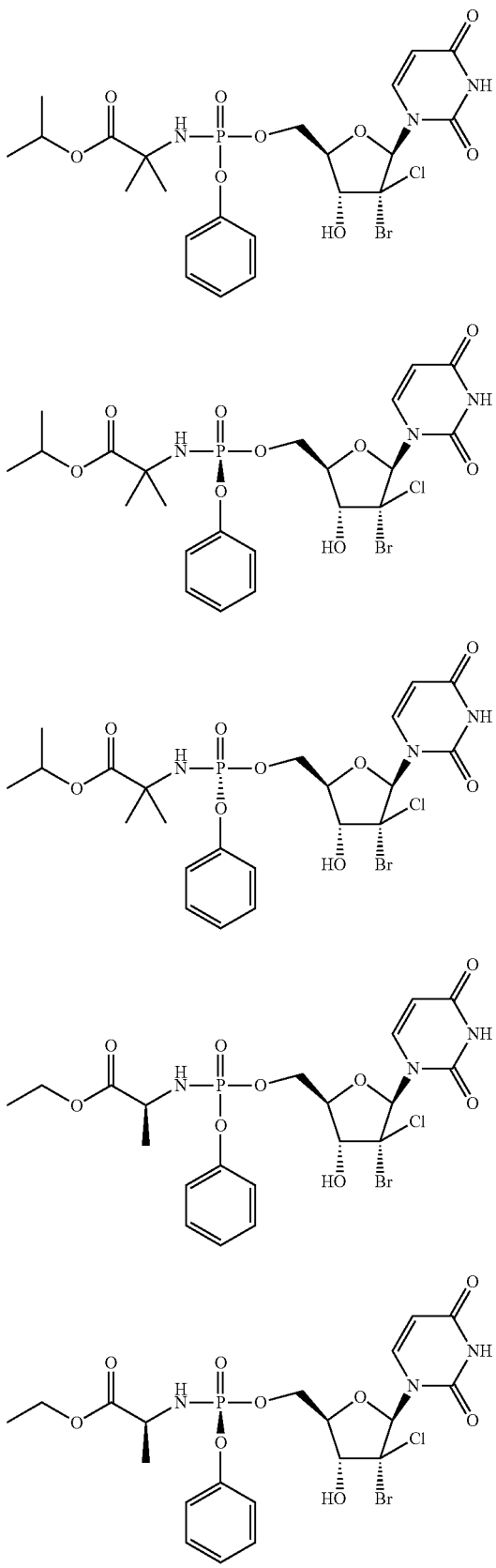

TABLE 3-continued
Exemplary Compounds
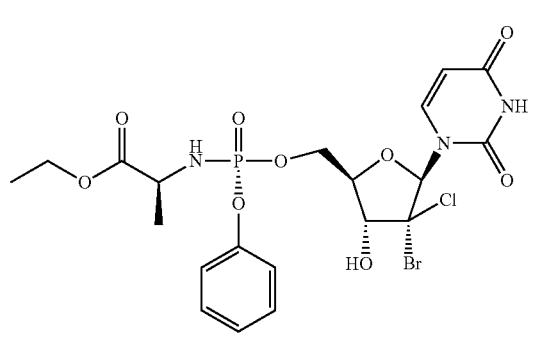 [SMILES: CCOC(=O)[C@H](C)N[P@@](=O)(OC[C@H]1O[C@@H](n2ccc(=O)[nH]c2=O)[C@](Cl)(Br)[C@@H]1O)Oc1ccccc1]
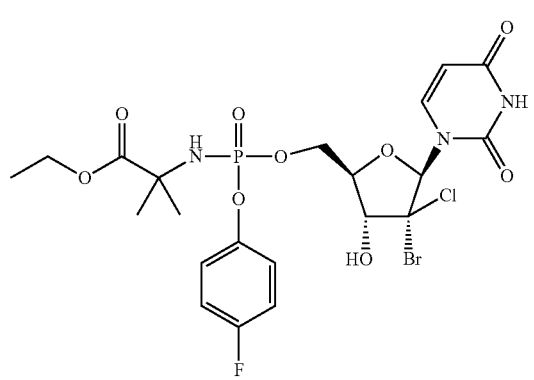 [SMILES: CCOC(=O)C(C)(C)NP(=O)(OC[C@H]1O[C@@H](n2ccc(=O)[nH]c2=O)[C@](Cl)(Br)[C@@H]1O)Oc1ccc(F)cc1]
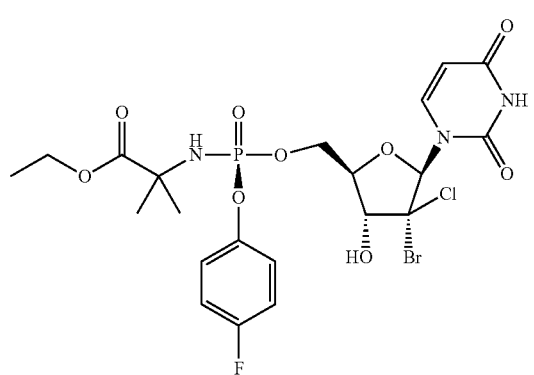 [SMILES: CCOC(=O)C(C)(C)N[P@](=O)(OC[C@H]1O[C@@H](n2ccc(=O)[nH]c2=O)[C@](Cl)(Br)[C@@H]1O)Oc1ccc(F)cc1]
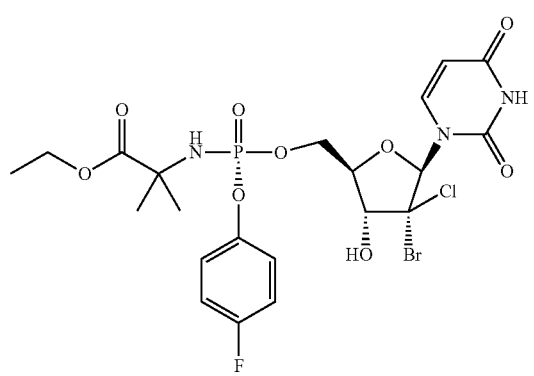 [SMILES: CCOC(=O)C(C)(C)N[P@@](=O)(OC[C@H]1O[C@@H](n2ccc(=O)[nH]c2=O)[C@](Cl)(Br)[C@@H]1O)Oc1ccc(F)cc1]
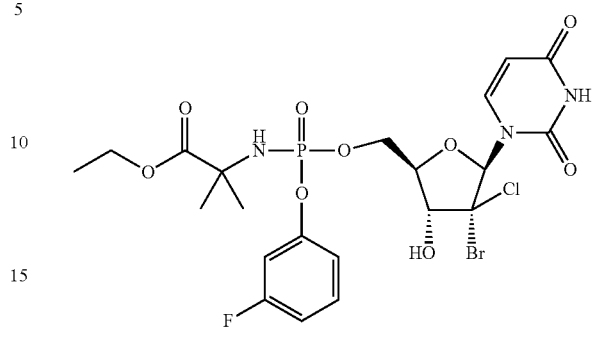
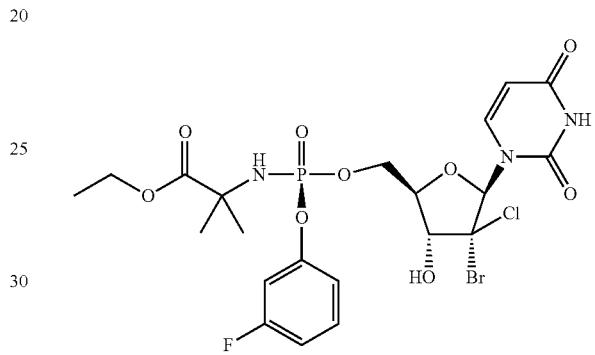
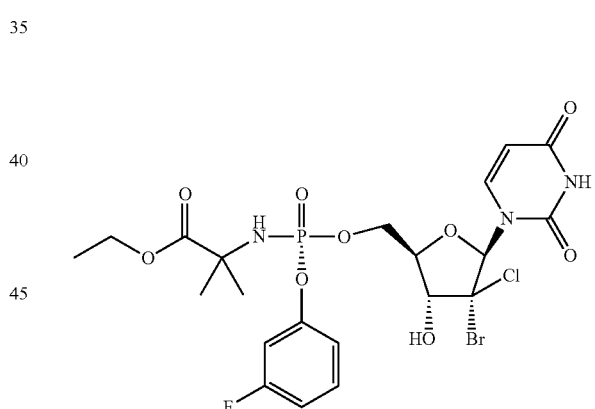
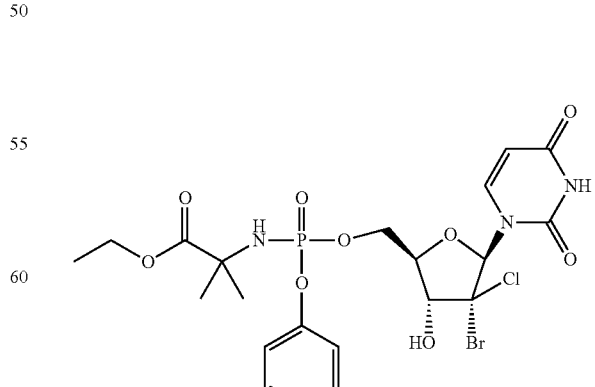

TABLE 3-continued
Exemplary Compounds
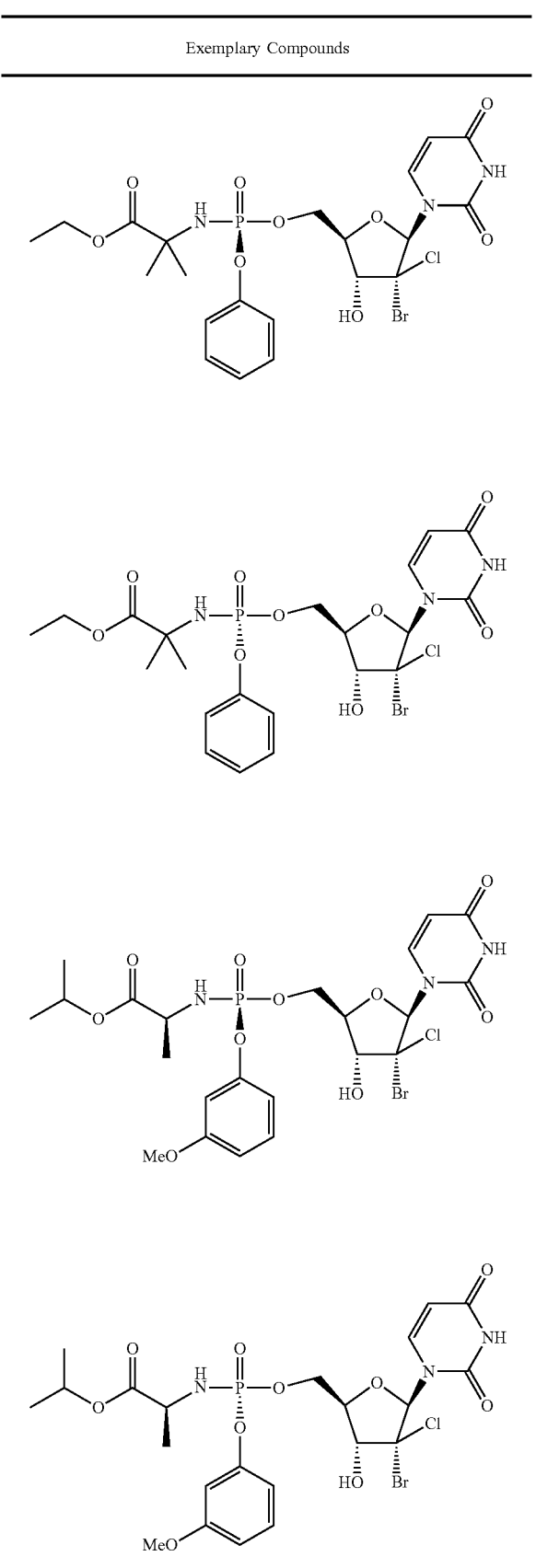
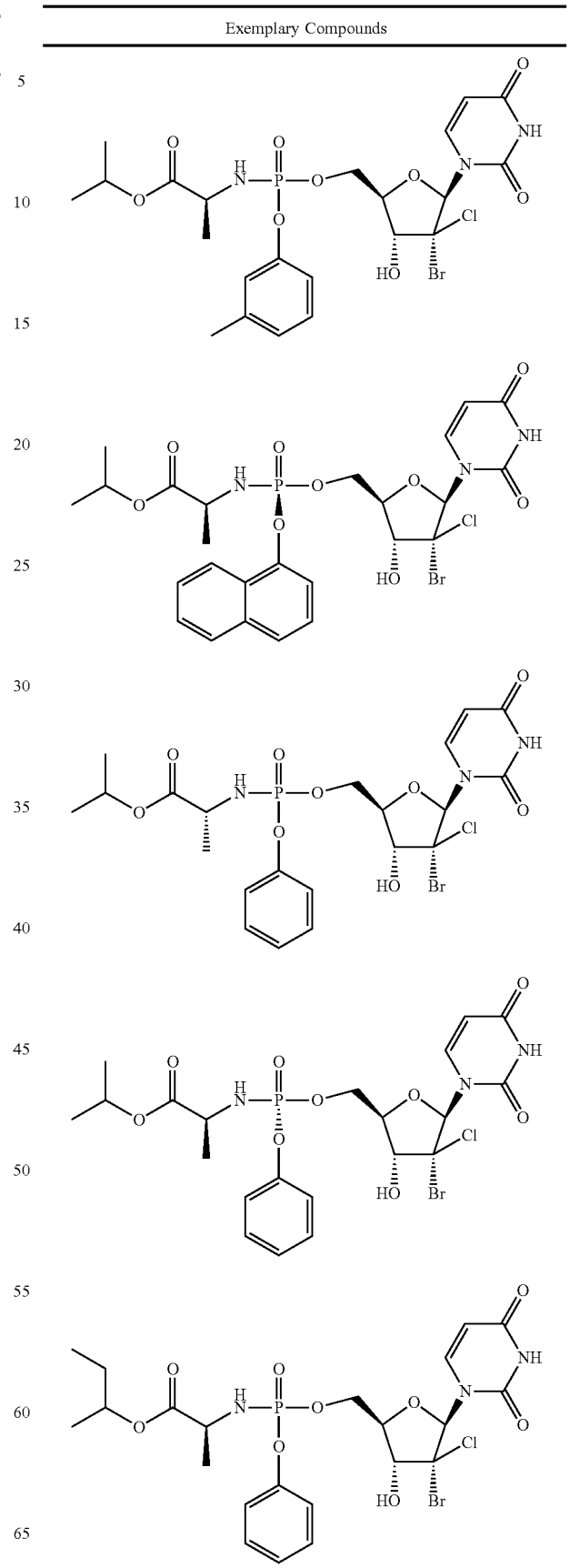

TABLE 3-continued
Exemplary Compounds
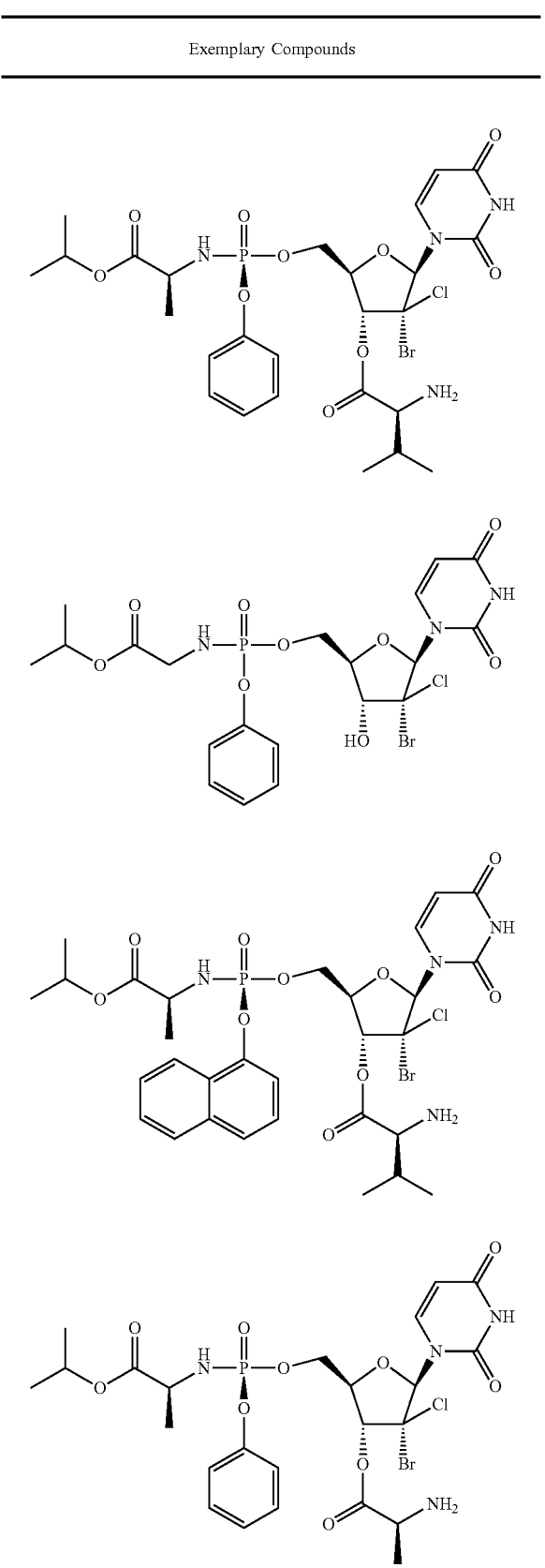
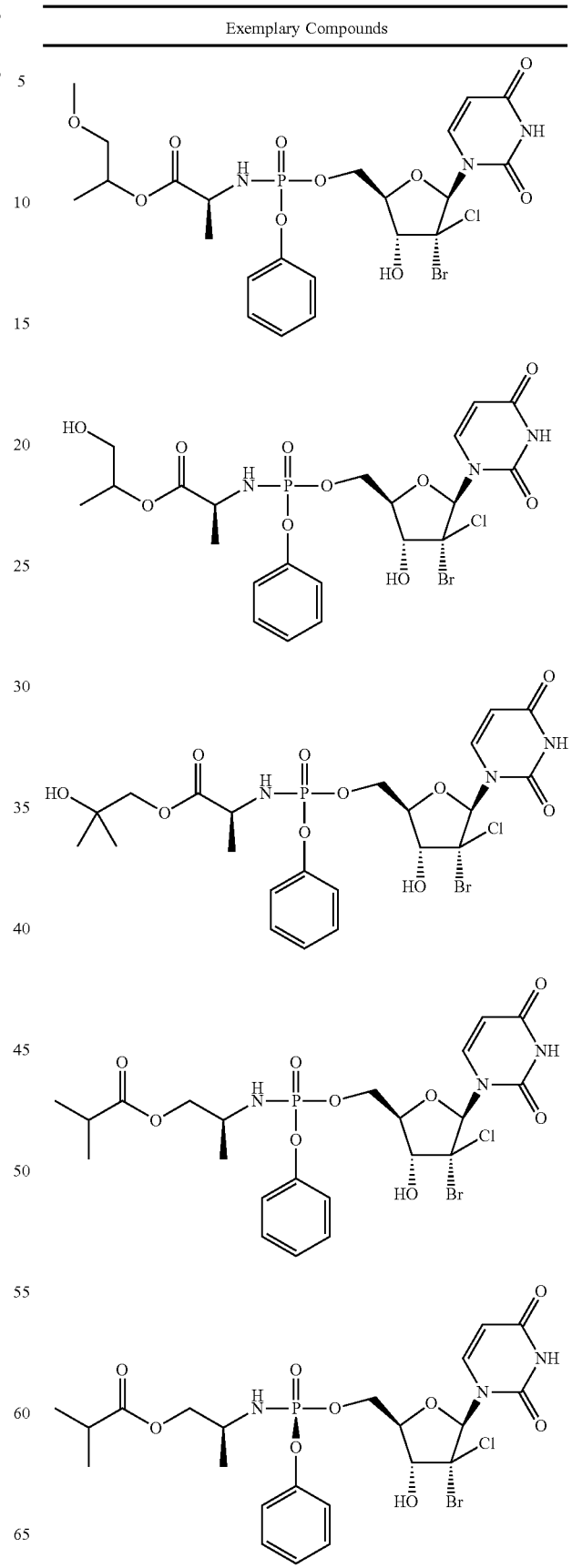

TABLE 3-continued
Exemplary Compounds
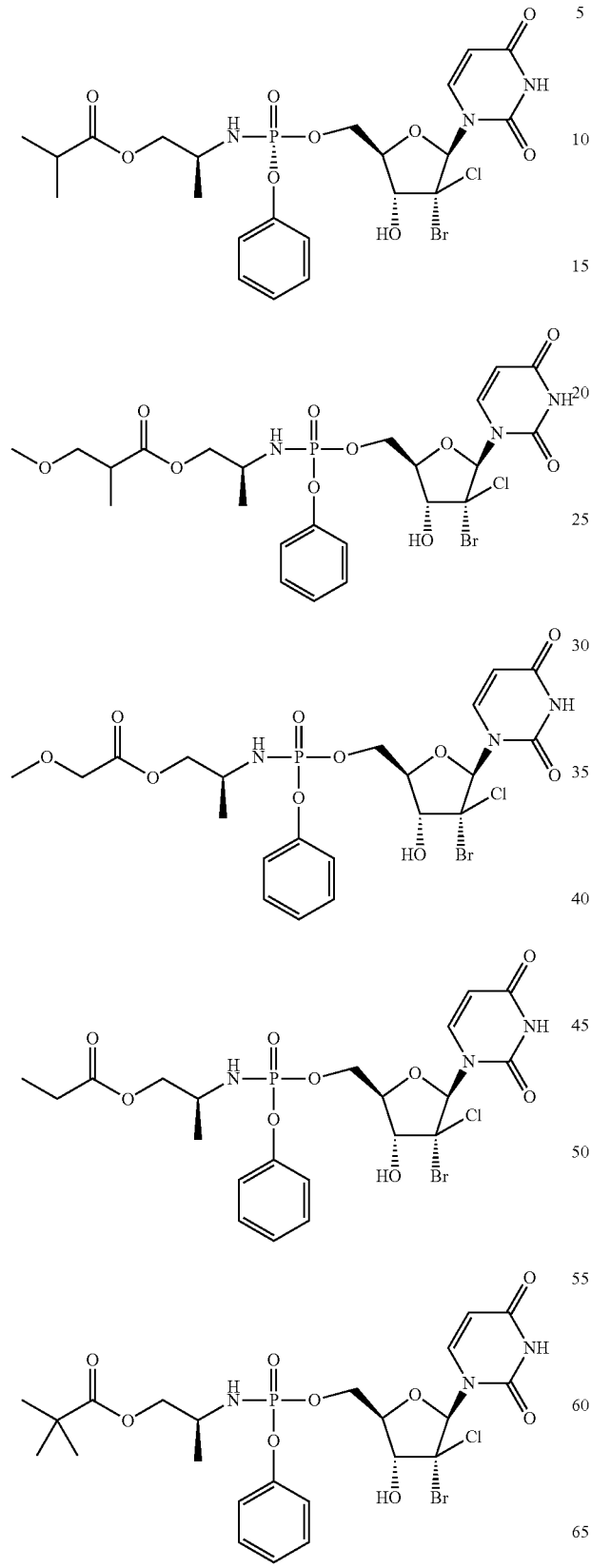
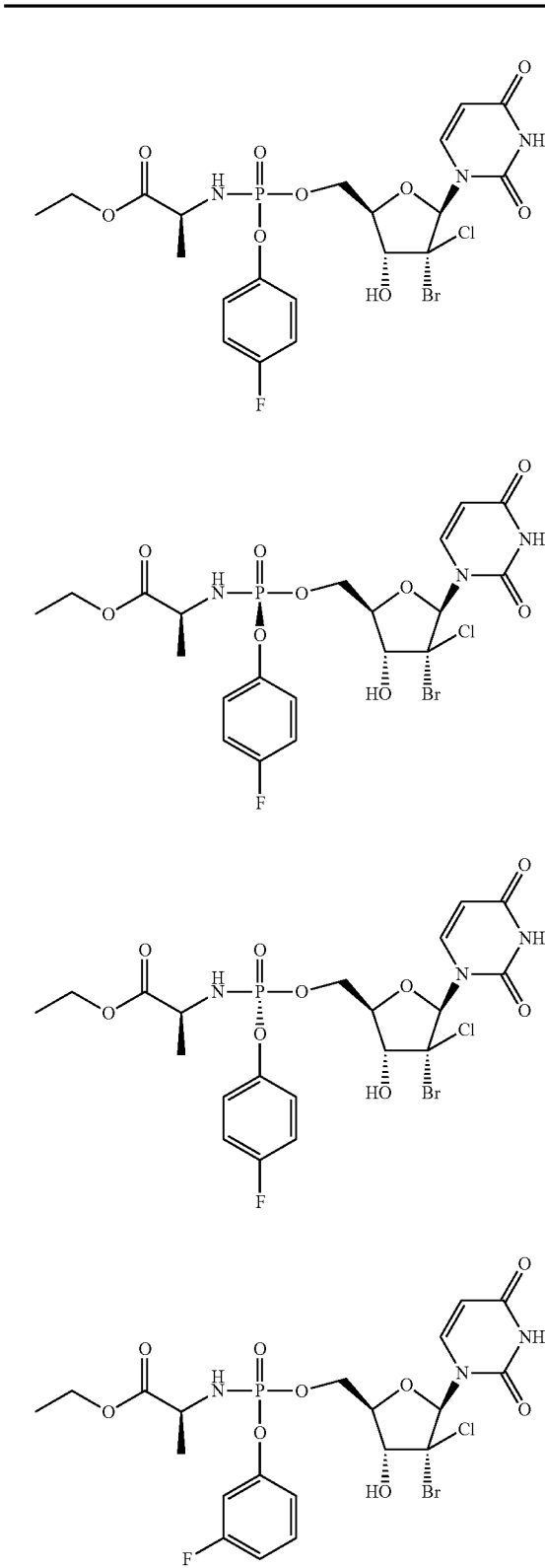

TABLE 3-continued

Exemplary Compounds

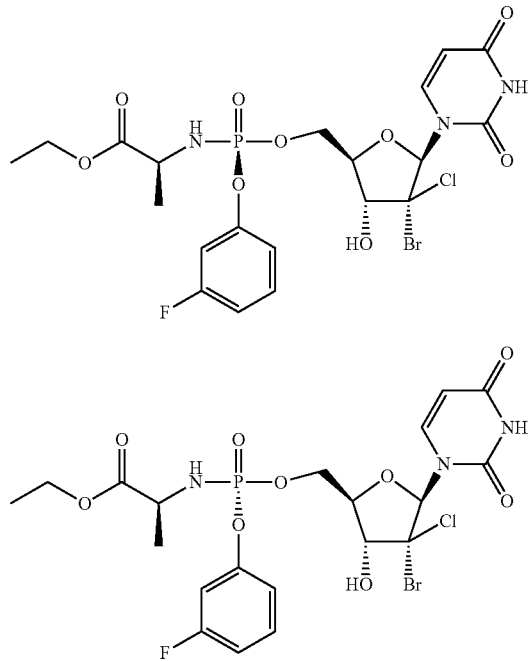

In yet another embodiment, the present invention features a compound the compound selected from Table 4. Table 4 has the same compound list as Table 3, except that for each compound in Table 3, Cl and Br are replaced with Br and F, respectively, in Table 4.

Any compound according to any of the above-described aspects can be prepared and used in prodrug forms. A suitable prodrug has chemically or metabolically cleavable group(s) and becomes, by solvolysis or under physiological conditions, a compound that is pharmaceutically active in vivo. A prodrug can be formed in a conventional manner by reaction of a functional group of the compound (such as an amino, hydroxy or carboxy group). Prodrugs often offer advantages of better metabolism, potency, solubility, tissue compatibility, or delayed release in mammals. Prodrugs include acid derivatives well known to practitioners of the art, such as, for example, esters prepared by reaction of the parent acidic compound with a suitable alcohol, or amides prepared by reaction of the parent acid compound with a suitable amine. Examples of prodrugs include, but are not limited to, acetate, formate, benzoate or other acylated derivatives of alcohol or amine functional groups within the compounds of the invention. For example, prodrugs can be aliphatic or aromatic esters derived from acidic groups on a compound of the invention. For another example, prodrugs can be aliphatic or aromatic esters of hydroxyl or amino groups on a compound of the invention. Phosphate prodrugs of hydroxyl groups are preferred prodrugs. Preferably, prodrugs used herein are phosphoramidate prodrugs. Non-limiting examples of suitable prodrug moieties are provided in Table 2, as described hereinabove.

In yet another aspect, any compound, salt or prodrug according to any aspect, embodiment, example and preference described herein can be isotopically substituted. Preferred isotopic substitutions include substitutions with stable or nonradioactive isotopes such as deuterium, $^{13}C$, $^{15}N$ or $^{18}O$. Incorporation of a heavy atom, such as substitution of deuterium for hydrogen, can give rise to an isotope effect that could alter the pharmacokinetics of the drug. In one example, at least 5 mol % (e.g., at least 10 mol %) of hydrogen in a compound of the present invention is substituted with deuterium. In another example, at least 25 mole % of hydrogen in a compound of the present invention is substituted with deuterium. In a further example, at least 50, 60, 70, 80 or 90 mole % of hydrogen in a compound of the present invention is substituted with deuterium. The natural abundance of deuterium is about 0.015%. Deuterium substitution or enrichment can be achieved, without limitation, by either exchanging protons with deuterium or by synthesizing the molecule with enriched or substituted starting materials. Other methods known in the art can also be used for isotopic substitutions.

In another aspect, the present invention features methods of using any compound/salt/prodrug according to any aspect, embodiment, example and preference described herein (e.g., the compound of Example 1, Example 3, Example 5, Example 6, Example 7 or Example 41, or a pharmaceutically acceptable salt thereof) to treat HCV infection. Such a compound, salt or prodrug has inhibitory activity against HCV polymerase. The method comprises administering an effective amount of such a compound, salt or prodrug to an HCV patient in need thereof. In one embodiment, the patient is infected with HCV genotype 1. In another embodiment, the patient is infected with HCV genotype 2. In yet another embodiment, the patient is infected with HCV genotype 3. In yet another embodiment, the patient is infected with HCV genotype 4. In yet another embodiment, the patient is infected with HCV genotype 5. In yet another embodiment, the patient is infected with HCV genotype 6.

It is contemplated that different compounds of the invention may have different anti-viral activities and/or toxicity/safety profiles. Compounds with less antiviral activities can be dosed more frequently and/or with greater amounts. Compounds with higher antiviral activities can be dosed less frequently and/or with lesser amounts. Moreover, a compound that does not have a commercially desired toxicity/safety profile does not prevent its utility under patent law as an anti-viral agent, despite the fact that the US FDA might not approve it for human treatment due to the agency's benefit-cost analyses and/or other non-patent related concerns.

In yet another aspect, the present invention features methods for treating HCV infection in a subject in need of such treatment. The methods comprise administering at least two direct acting antiviral agents (DAAs) to the subject for a duration of no more than 12 weeks, or for another duration as set forth herein. Said at least two DAAs comprise (1) a compound/salt/prodrug according to any aspect, embodiment, example and preference described herein (e.g., the compound of Example 1, 3, 6 or 7, or a pharmaceutically acceptable salt thereof), and (2) another DAA. The other DAA can be, for example, selected from an HCV protease inhibitor, an HCV polymerase inhibitor, an HCV NS5A inhibitor, or a cyclophilin inhibitor. Preferably, the other DAA is an HCV protease inhibitor, an HCV polymerase inhibitor, or an HCV NS5A inhibitor. More preferably, the other DAA is an HCV NS5A inhibitor, such as those described in US Patent Application Publication Nos. 2010/0317568 and 2012/0004196, both of which are incorporated herein by reference in their entireties. Highly preferably, the other DAA is the compound of Example 35 of US Patent Application Publication No. 2010/0317568. Also, highly preferably, the other DAA is the compound of Example 3.52 of US Patent Application Publication No. 2012/0004196. In one example, the duration of the treatment is 12 weeks. The duration of the treatment can also be, for example, no more than 8 weeks. Preferably, the two or more DAAs are administered in amounts effective to provide a sustained virological response (SVR) or achieve another desired measure of effectiveness in the subject. The subject is not administered ribavirin during the treatment regimen. The subject is also not administered interferon during the treatment regimen. Put another way, the methods exclude the administration of interferon or ribavirin to the subject, thereby avoiding the side effects associated with interferon and ribavirin.

In another aspect, the present invention features methods for treating a population of subjects having HCV infection. The methods comprise administering at least two DAAs to the subjects for a duration of no more than 12 weeks. Said at least two DAAs comprise (1) a compound/salt/prodrug according to any aspect, embodiment, example and preference described herein (e.g., the compound of Example 1, 3, 6 or 7, or a pharmaceutically acceptable salt thereof), and (2) another DAA. The other DAA can be, for example, selected from an HCV protease inhibitor, an HCV polymerase inhibitor, an HCV NS5A inhibitor, or a cyclophilin inhibitor. Preferably, the other DAA is an HCV protease inhibitor, an HCV polymerase inhibitor, or an HCV NS5A inhibitor. More preferably, the other DAA is an HCV NS5A inhibitor, such as those described in US Patent Application Publication Nos. 2010/0317568 and 2012/0004196, both of which are incorporated herein by reference in their entireties. Highly preferably, the other DAA is the compound of Example 35 of US Patent Application Publication No. 2010/0317568. Also, highly preferably, the other DAA is the compound of Example 3.52 of US Patent Application Publication No. 2012/0004196. Preferably, said at least two DAAs are administered to the subjects in amounts effective to result in SVR or another measure of effectiveness in at least about 70% of the population, preferably at least about 80% of the population, or more preferably at least about 90% of the population. The subjects are not administered ribavirin during the treatment regimen. The subjects are also not administered interferon during the treatment regimen. Put another way, the methods exclude the administration of interferon or ribavirin to the subject, thereby avoiding the side effects associated with interferon and ribavirin.

Non-limiting examples of the other DAAs include PSI-7977 (sofosbuvir), PSI-938, BMS-790052 (daclatasvir), BMS-650032 (asunaprevir), BMS-791325, GS-5885 (ledipasvir), GS-9451 (tegobuvir), GS-9190, GS-9256, BI-201335, BI-27127, telaprevir, VX-222, TMC-435 (simeprevir), MK-5172, MK-7009 (vaniprevir), danoprevir, paritaprevir, ombitasvir, ABT-493, and R7128 (mericitabine).

In any method described herein, the DAAs can be administered in any effective dosing schemes and/or frequencies; for example, they can each be administered daily. Each DAA can be administered either separately or in combination, and each DAA can be administered once a day, twice a day, or three times a day. Preferably, the DAAs employed herein are administered once daily.

In yet another aspect, the present invention features a combination of a compound/salt/prodrug according to any aspect, embodiment, example and preference described herein (e.g., the compound of Example 1, 3, 6 or 7, or a pharmaceutically acceptable salt thereof), and another DAA, for use to treat HCV infection. The other DAA can be, for example, selected from an HCV protease inhibitor, an HCV polymerase inhibitor, an HCV NS5A inhibitor, or a cyclophilin inhibitor. Preferably, the other DAA is an HCV protease inhibitor, an HCV polymerase inhibitor, or an HCV NS5A inhibitor. More preferably, the other DAA is an HCV NS5A inhibitor, such as those described in US Patent Application Publication Nos. 2010/0317568 and 2012/0004196, both of which are incorporated herein by reference in their entireties. Highly preferably, the other DAA is the compound of Example 35 of US Patent Application Publication No. 2010/0317568. Also, highly preferably, the other DAA is the compound of Example 3.52 of US Patent Application Publication No. 2012/0004196. The treatment comprises administering the DAAs to a subject infected with HCV. The duration of the treatment regimen is no more than twelve weeks (e.g., the duration being 12 weeks; or the duration being 11, 10, 9, 8, 7, 6, 5, 4, or 3 weeks). Preferably, the duration of the treatment regimen is twelve weeks. The duration of the treatment can also last, for example, no more than eight weeks (e.g., the duration being 8 weeks; or the duration being 7, 6, 5, 4, or 3 weeks). The treatment does not include administering interferon or ribavirin. The DAAs can be administered concurrently or sequentially. Preferably, the DAAs are administered once daily. As a non-limiting example, the patient being treated is infected with HCV genotype 1, such as genotype 1a or 1b. As another non-limiting example, the patient is infected with HCV genotype 2. As another non-limiting example, the patient is infected with HCV genotype 3. As another non-limiting example, the patient is infected with HCV genotype 4. As another non-limiting example, the patient is infected with HCV genotype 5. As another non-limiting example, the patient is infected with HCV genotype 6. As yet another non-limiting example, the patient is a HCV-treatment naïve patient, a HCV-treatment experienced patient, an interferon non-responder (e.g., a null responder), or not a candidate for interferon treatment. As used in this application, the interferon non-responder patients include partial interferon responders and interferon rebound patients. See GUIDANCE FOR INDUSTRY—CHRONIC HEPATITIS C VIRUS INFECTION: DEVELOPING DIRECT-ACTING ANTIVIRAL AGENTS FOR TREATMENT (FDA, September 2010, draft guidance) for the definitions of naïve, partial responder, responder relapser (i.e., rebound), and null responder patients. The interferon non-responder patients also include null responder patients. In one example of this aspect of the invention, the treatment lasts for 12 weeks, and the subject being treated is a naïve patient infected with HCV genotype 1. In another example, the treatment lasts for 11 weeks, and the subject being treated is a naïve patient infected with HCV genotype 1. In still another example, the treatment lasts for 10 weeks, and the subject being treated is a naïve patient infected with HCV genotype 1. In yet another example, the treatment lasts for 9 weeks, and the subject being treated is a naïve patient infected with HCV genotype 1. In yet another example, the treatment lasts for 8 weeks, and the subject being treated is a naïve patient infected with HCV genotype 1. In yet another example, the treatment lasts for 7 weeks, and the subject being treated is a naïve patient infected with HCV genotype 1. In yet another example, the treatment lasts for 6 weeks, and the subject being treated is a naïve patient infected with HCV genotype 1. In yet another example, the treatment lasts for 5 weeks, and the subject being treated is a naïve patient infected with HCV genotype 1. In yet another example, the treatment lasts for 4 weeks, and the subject being treated is a naïve patient infected with HCV genotype 1. In yet another example, the treatment lasts for 3 weeks, and the subject being treated is a naïve patient infected with HCV genotype 1. In yet another example, the treatment lasts for 12 weeks, and the subject being treated is a naïve patient infected with HCV genotype. In another example, the treatment lasts for 11 weeks, and the subject being treated is a naïve patient infected with HCV selected from genotypes 2, 3, 4, 5 or 6. In still another example, the treatment lasts for 10 weeks, and the subject being treated is a naïve patient infected with HCV selected from genotypes 2, 3, 4, 5 or 6. In yet another example, the treatment lasts for 9 weeks, and the subject being treated is a naïve patient infected with HCV selected from genotypes 2, 3, 4, 5 or 6. In yet another example, the treatment lasts for 8 weeks, and the subject being treated is a naïve patient infected with selected from genotypes 2, 3, 4, 5 or 6. In yet another example, the treatment lasts for 7 weeks, and the subject being treated is a naïve patient infected with selected from genotypes 2, 3, 4, 5 or 6. In yet another example, the treatment lasts for 6 weeks, and the subject being treated is a naïve patient infected with selected from genotypes 2, 3, 4, 5 or 6. In yet another example, the treatment lasts for 5 weeks, and the subject being treated is a naïve patient infected with selected from genotypes 2, 3, 4, 5 or 6. In yet another example, the treatment lasts for 4 weeks, and the subject being treated is a naïve patient infected with selected from genotypes 2, 3, 4, 5 or 6. In yet another example, the treatment lasts for 3 weeks, and the subject being treated is a naïve patient infected with selected from genotypes 2, 3, 4, 5 or 6. In yet another example, the treatment lasts for 12 weeks, and the subject being treated is a non-responder (e.g., a null responder) infected with HCV genotype 1. In another example, the treatment lasts for 11 weeks, and the subject being treated is a non-responder (e.g., a null responder) infected with HCV genotype 1. In still another example, the treatment lasts for 10 weeks, and the subject being treated is a non-responder (e.g., a null responder) infected with HCV genotype 1. In yet another example, the treatment lasts for 9 weeks, and the subject being treated is a non-responder (e.g., a null responder) infected with HCV genotype 1. In yet another example, the treatment lasts for 8 weeks, and the subject being treated is a non-responder (e.g., a null responder) infected with HCV genotype 1. In yet another example, the treatment lasts for 7 weeks, and the subject being treated is a non-responder (e.g., a null responder) infected with HCV genotype 1. In yet another example, the treatment lasts for 6 weeks, and the subject being treated is a non-responder (e.g., a null responder) infected with HCV genotype 1. In yet another example, the treatment lasts for 5 weeks, and the subject being treated is a non-responder (e.g., a null responder) infected with HCV genotype 1. In yet another example, the treatment lasts for 4 weeks, and the subject being treated is a non-responder (e.g., a null responder) infected with HCV genotype 1. In yet another example, the treatment lasts for 3 weeks, and the subject being treated is a non-responder (e.g., a null responder) infected with HCV genotype 1. In yet another example, the treatment lasts for 12 weeks, and the subject being treated is a non-responder (e.g., a null responder) infected with HCV selected from genotype 2, 3, 4, 5 or 6. In another example, the treatment lasts for 11 weeks, and the subject being treated is a non-responder (e.g., a null responder) infected with HCV selected from genotype 2, 3, 4, 5 or 6. In still another example, the treatment lasts for 10 weeks, and the subject being treated is a non-responder (e.g., a null responder) infected with HCV selected from genotype 2, 3, 4, 5 or 6. In yet another example, the treatment lasts for 9 weeks, and the subject being treated is a non-responder (e.g., a null responder) infected with HCV selected from genotype 2, 3, 4, 5 or 6. In yet another example, the treatment lasts for 8 weeks, and the subject being treated is a non-responder (e.g., a null responder) infected with HCV selected from genotype 2, 3, 4, 5 or 6. In yet another example, the treatment lasts for 7 weeks, and the subject being treated is a non-responder (e.g., a null responder) infected with HCV selected from genotype 2, 3, 4, 5 or 6. In yet another example, the treatment lasts for 6 weeks, and the subject being treated is a non-responder (e.g., a null responder) infected with HCV selected from genotype 2, 3, 4, 5 or 6. In yet another example, the treatment lasts for 5 weeks, and the subject being treated is a non-responder (e.g., a null responder) infected with HCV selected from genotype 2, 3, 4, 5 or 6. In yet another example, the treatment lasts for 4 weeks, and the subject being treated is a non-responder (e.g., a null responder) infected with HCV selected from genotype 2, 3, 4, 5 or 6. In yet another example, the treatment lasts for 3 weeks, and the subject being treated is a non-responder (e.g., a null responder) infected with HCV selected from genotype 2, 3, 4, 5 or 6.

A treatment regimen of the present invention generally constitutes a complete treatment regimen, i.e., no subsequent interferon-containing regimen is intended. Thus, a treatment or use described herein generally does not include any subsequent interferon-containing treatment. Preferably, a treatment or use described herein does not include any subsequent ribavirin-containing treatment.

The methods of the present invention can provide effective treatment of HCV infection without the use of interferon or ribavirin and for a shorter period of time, for example and without limitation, a treatment duration of no more than twelve weeks, alternatively no more than eleven weeks, alternatively no more than ten weeks, alternatively no more than nine weeks, alternatively no more than eight weeks, alternatively no more than seven weeks, alternatively no more than six weeks, alternatively no more than five weeks, alternatively no more than four weeks, or alternatively, no more than three weeks.

In one aspect, the present invention features methods for treating HCV infection in a subject comprising administering at least two DAAs, in the absence of interferon and ribavirin, to the subject for a duration of no more than twelve weeks, alternatively no more than eight weeks. Put another way, the methods exclude interferon and ribavirin. Said at least two DAAs comprise a compound/salt/prodrug according to any aspect, embodiment, example and preference described herein (e.g., the compound of Example 1, 3, 6 or 7, or a pharmaceutically acceptable salt thereof), and another DAA, which can be co-administered, or administered separately or independently, with the same or different dosing frequencies. Preferably, said at least two DAAs are administered once a day. They can also be administered, for example, twice a day or three times a day. The other DAA can be, for example, selected from an HCV protease inhibitor, an HCV polymerase inhibitor, an HCV NS5A inhibitor, or a cyclophilin inhibitor. Preferably, the other DAA is an HCV protease inhibitor, an HCV polymerase inhibitor, or an HCV NS5A inhibitor. More preferably, the other DAA is an HCV NS5A inhibitor, such as those described in US Patent Application Publication Nos. 2010/0317568 and 2012/0004196. Highly preferably, the other DAA is the compound of Example 35 of US Patent Application Publication No. 2010/0317568. Also, highly preferably, the other DAA is the compound of Example 3.52 of US Patent Application Publication No. 2012/0004196.

Various measures may be used to express the effectiveness of a method of the present invention. One such measure is SVR, which, as used herein, means that the virus is undetectable at the end of therapy and for at least 8 weeks after the end of therapy (SVR8); preferably, the virus is undetectable at the end of therapy and for at least 12 weeks after the end of therapy (SVR12); more preferably, the virus is undetectable at the end of therapy and for at least 16 weeks after the end of therapy (SVR16); and highly preferably, the virus is undetectable at the end of therapy and for at least 24 weeks after the end of therapy (SVR24). SVR24 is often considered as a functional definition of cure; and a high rate of SVR at less than 24 week post-treatment (e.g., SVR8 or SVR12) can be predictive of a high rate of SVR24.

In some embodiments, a treatment regimen of the invention comprises treating a population of subjects having HCV infection (e.g. treatment naïve subjects), and the regimen comprises administering at least two DAAs to the subjects for a duration of no more than 12 weeks, or for another duration disclosed herein, wherein said at least two DAAs comprise a compound/salt/prodrug according to any aspect, embodiment, example and preference described herein (e.g., the compound of Example 1, 3, 6 or 7, or a pharmaceutically acceptable salt thereof), and another DAA, and are administered to the subjects in amounts effective to provide an SVR (e.g., SVR12 or SVR24) in at least about 70% of the population, alternatively at least about 75% of the population, alternatively at least about 80% of the population, alternatively at least about 85% of the population, alternatively at least about 90% of the population, alternatively at least about 95% of the population, alternatively about 100% of the population. The other DAA can be, for example, selected from an HCV protease inhibitor, an HCV polymerase inhibitor, an HCV NS5A inhibitor, or a cyclophilin inhibitor. Preferably, the other DAA is an HCV protease inhibitor, an HCV polymerase inhibitor, or an HCV NS5A inhibitor. More preferably, the other DAA is an HCV NS5A inhibitor, such as those described in US Patent Application Publication Nos. 2010/0317568 and 2012/0004196. Highly preferably, the other DAA is the compound of Example 35 of US Patent Application Publication No. 2010/0317568. Also, highly preferably, the other DAA is the compound of Example 3.52 of US Patent Application Publication No. 2012/0004196.

In some embodiments, a treatment regimen of the invention comprises treating a population of IFN experienced subjects (e.g., interferon non-responders) having HCV infection, and the method comprises administering at least two DAAs to the subjects for a duration of no more than 12 weeks, or for another duration disclosed herein, wherein said at least two DAAs comprise (1) a compound/salt/prodrug according to any aspect, embodiment, example and preference described herein (hereinafter "Compound 1", which preferably is the compound of Example 1 or Example 3 or Example 6 or Example 41 or a pharmaceutically acceptable salt thereof), and another DAA (hereinafter "Compound 2"), and are administered to the subjects in amounts effective to provide an SVR (e.g., SVR12 or SVR24) in at least about 50% of the population, alternatively at least about 55% of the population, alternatively at least about 60% of the population, alternatively at least about 65% of the population, alternatively at least about 70% of the population, alternatively at least about 75% of the population, alternatively at least about 80% of the population, alternatively at least about 85% of the population, alternatively at least about 90% of the population, alternatively at least about 95% of the population, or alternatively about 100% of the population.

In any aspect, embodiment, example and preference described herein, Compound 2 can be, for example, selected from an HCV protease inhibitor, an HCV polymerase inhibitor, an HCV NS5A inhibitor, or a cyclophilin inhibitor. Preferably, Compound 2 is an HCV protease inhibitor, an HCV polymerase inhibitor, or an HCV NS5A inhibitor. More preferably, Compound 2 is an HCV NS5A inhibitor, such as those described in US Patent Application Publication Nos. 2010/0317568 and 2012/0004196. Highly preferably, Compound 2 is the compound of Example 35 of US Patent Application Publication No. 2010/0317568. Also, highly preferably, Compound 2 is the compound of Example 3.52 of US Patent Application Publication No. 2012/0004196.

In one aspect, the present invention features a method of treating HCV infection, comprising administering to a patient in need thereof an effective amount of a combination of at least two DAAs, wherein said at least two DAAs comprise Compound 1 and Compound 2. The treatment lasts 8 weeks and does not include administration of any interferon or ribavirin. The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 and Compound 2, said at least two DAAs can also include one or more additional DAAs selected from, for example, HCV protease inhibitors, HCV polymerase inhibitors, or HCV NS5A inhibitors. Non-limiting examples of such additional DAAs include PSI-7977, PSI-938, TMC-435, BMS-790052, BMS-650032, GS-5885, GS-9190, GS-9451, BI-201335, BI-207127, telaprevir, VX-222, mericitabine, and danoprevir.

In another aspect, the present invention features a method of treating HCV infection, comprising administering to a patient in need thereof an effective amount of a combination of at least two DAAs, wherein said at least two DAAs comprise Compound 1 and Compound 2. The treatment lasts 7 weeks and does not include administration of any interferon or ribavirin. The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 and Compound 2, said at least two DAAs can also include one or more additional DAAs selected from, for example, HCV protease inhibitors, HCV polymerase inhibitors, or HCV NS5A inhibitors. Non-limiting examples of such additional DAAs include PSI-7977, PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 and Compound 2. The treatment lasts 6 weeks and does not include administration of any interferon or ribavirin. The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 and Compound 2, said at least two DAAs can also include one or more additional DAAs selected from, for example, HCV protease inhibitors, HCV polymerase inhibitors, or HCV NS5A inhibitors. Non-limiting examples of such additional DAAs include PSI-7977, PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 and Compound 2. The treatment lasts 5 weeks and does not include administration of any interferon or ribavirin. The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 and Compound 2, said at least two DAAs can also include one or more additional DAAs selected from, for example, HCV protease inhibitors, HCV polymerase inhibitors, or HCV NS5A inhibitors. Non-limiting examples of such additional DAAs include PSI-7977, PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 and Compound 2. The treatment lasts 4 weeks and does not include administration of any interferon or ribavirin. The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 and Compound 2, said at least two DAAs can also include one or more additional DAAs selected from, for example, HCV protease inhibitors, HCV polymerase inhibitors, or HCV NS5A inhibitors. Non-limiting examples of such additional DAAs include PSI-7977, PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 and Compound 2. The treatment lasts 3 weeks and does not include administration of any interferon or ribavirin. The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 and Compound 2, said at least two DAAs can also include one or more additional DAAs selected from, for example, HCV protease inhibitors, HCV polymerase inhibitors, or HCV NS5A inhibitors. Non-limiting examples of such additional DAAs include PSI-7977, PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 and Compound 2. The treatment lasts 24 weeks and does not include administration of any interferon or ribavirin. The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 and Compound 2, said at least two DAAs can also include one or more additional DAAs selected from, for example, HCV protease inhibitors, HCV polymerase inhibitors, or HCV NS5A inhibitors. Non-limiting examples of such additional DAAs include PSI-7977, PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 and Compound 2. The treatment lasts 13 to 23 weeks (e.g., the duration of the treatment is selected from 13, 14, 15, 16, 17, 18, 19, 20, 21, 22 or 23 weeks) and does not include administration of any interferon or ribavirin. The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 and Compound 2, said at least two DAAs can also include one or more additional DAAs selected from, for example, HCV protease inhibitors, HCV polymerase inhibitors, or HCV NS5A inhibitors. Non-limiting examples of such additional DAAs include PSI-7977, PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 and Compound 2. The treatment lasts 12 weeks and does not include administration of any interferon or ribavirin. The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 and Compound 2, said at least two DAAs can also include one or more additional DAAs selected from, for example, HCV protease inhibitors, HCV polymerase inhibitors, or HCV NS5A inhibitors. Non-limiting examples of such additional DAAs include PSI-7977, PSI-938, TMC-435, BMS-790052, BMS-650032, GS-5885, GS-9190, GS-9451, BI-201335, BI-207127, telaprevir, VX-222, mericitabine, and danoprevir. As used in this application, a HCV polymerase inhibitor can be a nucleoside polymerase inhibitor, a nucleotide polymerase inhibitor, a non-nucleoside polymerase inhibitor, or a non-nucleotide polymerase inhibitor.

In yet another aspect, the present invention features a method of treating HCV infection, comprising administering to a patient in need thereof an effective amount of a combination of at least two DAAs, wherein said at least two DAAs comprise Compound 1 and Compound 2. The treatment lasts 11 weeks and does not include administration of any interferon or ribavirin. The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 and Compound 2, said at least two DAAs can also include one or more additional DAAs selected from, for example, HCV protease inhibitors, HCV polymerase inhibitors, or HCV NS5A inhibitors. Non-limiting examples of such additional DAAs include PSI-7977, PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 and Compound 2. The treatment lasts 10 weeks and does not include administration of any interferon or ribavirin. The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 and Compound 2, said at least two DAAs can also include one or more additional DAAs selected from, for example, HCV protease inhibitors, HCV polymerase inhibitors, or HCV NS5A inhibitors. Non-limiting examples of such additional DAAs include PSI-7977, PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 and Compound 2. The treatment lasts 9 weeks and does not include administration of any interferon or ribavirin. The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 and Compound 2, said at least two DAAs can also include one or more additional DAAs selected from, for example, HCV protease inhibitors, HCV polymerase inhibitors, or HCV NS5A inhibitors. Non-limiting examples of such additional DAAs include PSI-7977, PSI-938, TMC-435, BMS-790052, BMS-650032, GS-5885, GS-9190, GS-9451, BI-201335, BI-207127, telaprevir, VX-222, mericitabine, and danoprevir.

A method of the present invention can be used to treat a naïve patient or a treatment experienced patient. Treatment experienced patients include interferon non-responders (e.g., null responders), partial responders, and relapsers. A method of the present invention can also be used to treat patients who are not candidates for interferon treatment. Patients who are not candidates for interferon treatment include, but are not limited to, one or more of the following groups: patients intolerant to interferon, patients who refuse to take interferon treatment, patients with medical conditions which preclude them from taking interferon, and patients who have an increased risk of side effects or infection by taking interferon.

In any method described herein, one or more additional DAAs can be optionally used in the treatment regimen in addition to Compound 1 and Compound 2. These additional DAAs can be HCV protease inhibitors, HCV nucleoside or nucleotide polymerase inhibitors, HCV non-nucleoside polymerase inhibitors, HCV NS3B inhibitors, HCV NS4A inhibitors, HCV NS5A inhibitors, HCV NS5B inhibitors, HCV entry inhibitors, cyclophilin inhibitors, or combinations thereof.

Preferred HCV protease inhibitors for this purpose include, but are not limited to, telaprevir (Vertex), boceprevir (Merck), BI-201335 (Boehringer Ingelheim), GS-9451 (Gilead), and BMS-650032 (BMS). Other suitable protease inhibitors include, but are not limited to, ACH-1095 (Achillion), ACH-1625 (Achillion), ACH-2684 (Achillion), AVL-181 (Avila), AVL-192 (Avila), BMS-650032 (BMS), danoprevir (RG7227/ITMN-191, Roche), GS-9132 (Gilead), GS-9256 (Gilead), IDX-136 (Idenix), IDX-316 (Idenix), IDX-320 (Idenix), MK-5172 (Merck), narlaprevir (Schering-Plough Corp), PHX-1766 (Phenomix), TMC-435 (Tibotec), vaniprevir (MK-7009, Merck), VBY708 (Virobay), VX-500 (Vertex), VX-813 (Vertex), VX-985 (Vertex), or a combination thereof.

Preferred non-nucleoside HCV polymerase inhibitors for use in the present invention include, but are not limited to, GS-9190 (Gilead), BI-207127 (Boehringer Ingelheim), and VX-222 (VCH-222) (Vertex & ViraChem). Preferred nucleotide HCV polymerase inhibitors include, but are not limited to, PSI-7977 (Gilead), and PSI-938 (Gilead). Other suitable and non-limiting examples of suitable HCV polymerase inhibitors include ANA-598 (Anadys), BI-207127 (Boehringer Ingelheim), BILB-1941 (Boehringer Ingelheim), BMS-791325 (BMS), filibuvir, GL59728 (Glaxo), GL60667 (Glaxo), GS-9669 (Gilead), IDX-375 (Idenix), MK-3281 (Merck), tegobuvir, TMC-647055 (Tibotec), VCH-759 (Vertex & ViraChem), VCH-916 (ViraChem), VX-759 (Vertex), GS-6620 (Gilead), IDX-102 (Idenix), IDX-184 (Idenix), INX-189 (Inhibitex), MK-0608 (Merck), RG7128 (Roche), TMC64912 (Medivir), GSK625433 (GlaxoSmithKline), BCX-4678 (BioCryst), ALS-2200 (Alios BioPharma/Vertex), ALS-2158 (Alios BioPharma/Vertex), or a combination thereof. A polymerase inhibitor may be a nucleoside or nucleotide polymerase inhibitor, such as GS-6620 (Gilead), IDX-102 (Idenix), IDX-184 (Idenix), INX-189 (Inhibitex), MK-0608 (Merck), PSI-7977 (Gilead), PSI-938 (Gilead), RG7128 (Roche), TMC64912 (Medivir), ALS-2200 (Alios BioPharma/Vertex), ALS-2158 (Alios BioPharma/Vertex), or a combination therefore. A polymerase inhibitor may also be a non-nucleoside polymerase inhibitor, such as PF-00868554 (Pfizer), ANA-598 (Anadys), BI-207127 (Boehringer Ingelheim), BILB-1941 (Boehringer Ingelheim), BMS-791325 (BMS), filibuvir, GL59728 (Glaxo), GL60667 (Glaxo), GS-9669 (Gilead), IDX-375 (Idenix), MK-3281 (Merck), tegobuvir (Gilead), TMC-647055 (Tibotec), VCH-759 (Vertex & ViraChem), VCH-916 (ViraChem), VX-222 (VCH-222) (Vertex & ViraChem), VX-759 (Vertex), or a combination thereof.

Preferred NS5A inhibitors include, but are not limited to, BMS-790052 (BMS) and GS-5885 (Gilead). Non-limiting examples of suitable NS5A inhibitors include GSK62336805 (GlaxoSmithKline), ACH-2928 (Achillion), AZD2836 (Astra-Zeneca), AZD7295 (Astra-Zeneca), BMS-790052 (BMS), BMS-824393 (BMS), GS-5885 (Gilead), PPI-1301 (Presidio), PPI-461 (Presidio) A-831 (Arrow Therapeutics), A-689 (Arrow Therapeutics) or a combination thereof.

Non-limiting examples of suitable cyclophilin inhibitors include alisporovir (Novartis & Debiopharm), NM-811 (Novartis), SCY-635 (Scynexis), or a combination thereof.

Non-limiting examples of suitable HCV entry inhibitors include ITX-4520 (iTherx), ITX-5061 (iTherx), or a combination thereof.

Specific examples of other DAA agents that are suitable for inclusion in a method of the present invention include, but are not limited to, AP-H005, A-831 (Arrow Therapeutics) (NS5A inhibitor), A-689 (Arrow Therapeutics) (NS5A inhibitor), INX08189 (Inhibitex) (polymerase inhibitor), ITMN-191 (Intermune/Roche) (NS3/4A Protease inhibitor), VBY-376 (Protease Inhibitor) (Virobay), ACH-1625 (Achillion, Protease inhibitor), IDX136 (Idenix, Protease Inhibitor), IDX316 (Idenix, Protease inhibitor), VX-813 (Vertex), SCH 900518 (Schering-Plough), TMC-435 (Tibotec), ITMN-191 (Intermune, Roche), MK-7009 (Merck), IDX-PI (Novartis), R7128 (Roche), PF-868554 (Pfizer) (non-nucleoside polymerase inhibitor), PF-4878691 (Pfizer), IDX-184 (Idenix), IDX-375 (Idenix, NS5B polymerase inhibitor), PPI-461 (Presidio), BILB-1941 (Boehringer Ingelheim), GS-9190 (Gilead), BMS-790052 (BMS), CTS-1027 (Conatus), GS-9620 (Gilead), PF-4878691 (Pfizer), RO5303253 (Roche), ALS-2200 (Alios BioPharma/Vertex), ALS-2158 (Alios BioPharma/Vertex), GSK62336805 (GlaxoSmithKline), or any combinations thereof.

In some embodiments, the present invention features methods for treating patients infected with HCV genotype 1, such as 1a or 1b. The methods comprise administering to such a patient a combination of at least 2 DAAs for no more than 12 weeks (e.g., the duration being 12 weeks), such as no more than 8 weeks (e.g., the duration being 8 weeks), wherein the treatment does not include administration of either interferon or ribavirin, and said at least 2 DAAs comprise Compound 1 and Compound 2. Compound 1 and Compound 2 can be administered in therapeutically effective amounts to provide a SVR (for example, SVR12 or SVR24) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 8 weeks.

In some embodiments, the present invention features methods for treating patients with HCV genotype 2 or 3 infection. The methods comprise administering to such a patient a combination of at least 2 DAAs for no more than 12 weeks (e.g., the duration being 12 weeks), such as no more than 8 weeks (e.g., the duration being 8 weeks), wherein the treatment does not include administration of either interferon or ribavirin, and said at least 2 DAAs comprise Compound 1 and Compound 2. Compound 1 and Compound 2 can be administered in therapeutically effective amounts to provide a SVR (for example, SVR12 or SVR24) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 8 weeks.

In some embodiments, the present invention features methods for treating patients with HCV genotype 2 infection. The methods comprise administering to such a patient a combination of at least 2 DAAs for no more than 12 weeks (e.g., the duration being 12 weeks), such as no more than 8 weeks (e.g., the duration being 8 weeks), wherein the treatment does not include administration of either interferon or ribavirin, and said at least 2 DAAs comprise Compound 1 and Compound 2. Compound 1 and Compound 2 can be administered in therapeutically effective amounts to provide a SVR (for example, SVR12 or SVR24) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 8 weeks.

In some embodiments, the present invention features methods for treating patients with HCV genotype 3 infection. The methods comprise administering to such a patient a combination of at least 2 DAAs for no more than 12 weeks (e.g., the duration being 12 weeks), such as no more than 8 weeks (e.g., the duration being 8 weeks), wherein the treatment does not include administration of either interferon or ribavirin, and said at least 2 DAAs comprise Compound 1 and Compound 2. Compound 1 and Compound 2 can be administered in therapeutically effective amounts to provide a SVR (for example, SVR12 or SVR24) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 8 weeks.

In some embodiments, the present invention features methods for treating patients with HCV genotype 4 infection. The methods comprise administering to such a patient a combination of at least 2 DAAs for no more than 12 weeks (e.g., the duration being 12 weeks), such as no more than 8 weeks (e.g., the duration being 8 weeks), wherein the treatment does not include administration of either interferon or ribavirin, and said at least 2 DAAs comprise Compound 1 and Compound 2. Compound 1 and Compound 2 can be administered in therapeutically effective amounts to provide a SVR (for example, SVR12 or SVR24) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 8 weeks.

In some embodiments, the present invention features methods for treating patients with HCV genotype 5 infection. The methods comprise administering to such a patient a combination of at least 2 DAAs for no more than 12 weeks (e.g., the duration being 12 weeks), such as no more than 8 weeks (e.g., the duration being 8 weeks), wherein the treatment does not include administration of either interferon or ribavirin, and said at least 2 DAAs comprise Compound 1 and Compound 2. Compound 1 and Compound 2 can be administered in therapeutically effective amounts to provide a SVR (for example, SVR12 or SVR24) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 8 weeks.

In some embodiments, the present invention features methods for treating patients with HCV genotype 6 infection. The methods comprise administering to such a patient a combination of at least 2 DAAs for no more than 12 weeks (e.g., the duration being 12 weeks), such as no more than 8 weeks (e.g., the duration being 8 weeks), wherein the treatment does not include administration of either interferon or ribavirin, and said at least 2 DAAs comprise Compound 1 and Compound 2. Compound 1 and Compound 2 can be administered in therapeutically effective amounts to provide a SVR (for example, SVR12 or SVR24) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 8 weeks.

In any method, aspect, embodiment, example and preference described herein, where at least two DAAs comprise Compound 1 and Compound 2, said at least two DAAs preferably consist of Compound 1 and Compound 2. Preferably, Compound 1 is the compound of Example 3 or a pharmaceutically acceptable salt thereof. Also preferably, Compound 1 is the compound of Example 5 or a pharmaceutically acceptable salt thereof. Also preferably, Compound 1 is the compound of Example 6 or a pharmaceutically acceptable salt thereof. Also preferably, Compound 1 is the compound of Example 7 or a pharmaceutically acceptable salt thereof. Also preferably, Compound 1 is the compound of Example 1 or a pharmaceutically acceptable salt thereof. Also preferably, Compound 1 is selected from Table 3. Also preferably, Compound 1 is selected from Table 4.

In any method, aspect, embodiment, example and preference described herein, where at least two DAAs comprise Compound 1 and Compound 2, said at least two DAAs preferably consist of Compound 1, Compound 2 and a third DAA. Preferably, Compound 1 is the compound of Example 3 or a pharmaceutically acceptable salt thereof. Also preferably, Compound 1 is the compound of Example 6 or a pharmaceutically acceptable salt thereof. Also preferably, Compound 1 is the compound of Example 7 or a pharmaceutically acceptable salt thereof. Also preferably, Compound 1 is the compound of Example 41 or a pharmaceutically acceptable salt thereof. Also preferably, Compound 1 is the compound of Example 1 or a pharmaceutically acceptable salt thereof. Also preferably, Compound 1 is selected from Table 3. Also preferably, Compound 1 is selected from Table 4.

It will be understood that the specific dose level for any particular patient will depend upon a variety of factors including the activity of the specific compound employed, the age, body weight, general health, sex, diet, time of administration, route of administration, rate of excretion, drug combination, and the severity of the disease undergoing therapy.

In any method described herein, Compound 1 and Compound 2 may be co-formulated in a single dosage form. Non-limiting examples of suitable dosage forms include liquid or solid dosage forms. Preferably, Compound 1 and Compound 2 are formulated in a single solid dosage form in which at least one of the DAAs is in an amorphous form, or highly preferably molecularly dispersed, in a matrix which comprises a pharmaceutically acceptable water-soluble polymer and a pharmaceutically acceptable surfactant. The other DAAs can also be in an amorphous form or molecularly dispersed in the matrix, or formulated in different form(s) (e.g., in a crystalline form). More preferably, each of the two DAAs is in an amorphous form, or highly preferably molecularly dispersed, in a matrix which comprises a pharmaceutically acceptable water-soluble polymer and a pharmaceutically acceptable surfactant. Preferably, Compound 1 is the compound of Example 3 or a pharmaceutically acceptable salt thereof. Also preferably, Compound 1 is the compound of Example 6 or a pharmaceutically acceptable salt thereof. Also preferably, Compound 1 is the compound of Example 41 or a pharmaceutically acceptable salt thereof. Also preferably, Compound 1 is the compound of Example 5 or a pharmaceutically acceptable salt thereof. Also preferably, Compound 1 is the compound of Example 7 or a pharmaceutically acceptable salt thereof. Also preferably, Compound 1 is the compound of Example 1 or a pharmaceutically acceptable salt thereof. Also preferably, Compound 1 is selected from Table 3. Also preferably, Compound 1 is selected from Table 4.

In any method described herein, the patient being treated can be a treatment-naïve patient. Preferably, Compound 1 is the compound of Example 3 or a pharmaceutically acceptable salt thereof. Also preferably, Compound 1 is the compound of Example 6 or a pharmaceutically acceptable salt thereof. Also preferably, Compound 1 is the compound of Example 5 or a pharmaceutically acceptable salt thereof. Also preferably, Compound 1 is the compound of Example 41 or a pharmaceutically acceptable salt thereof. Also preferably, Compound 1 is the compound of Example 7 or a pharmaceutically acceptable salt thereof. Also preferably, Compound 1 is the compound of Example 1 or a pharmaceutically acceptable salt thereof. Also preferably, Compound 1 is selected from Table 3. Also preferably, Compound 1 is selected from Table 4.

In any method described herein, the patient being treated can be an interferon non-responder. Preferably, Compound 1 is the compound of Example 3 or a pharmaceutically acceptable salt thereof. Also preferably, Compound 1 is the compound of Example 5 or a pharmaceutically acceptable salt thereof. Also preferably, Compound 1 is the compound of Example 6 or a pharmaceutically acceptable salt thereof. Also preferably, Compound 1 is the compound of Example 7 or a pharmaceutically acceptable salt thereof. Also preferably, Compound 1 is the compound of Example 41 or a pharmaceutically acceptable salt thereof. Also preferably, Compound 1 is the compound of Example 1 or a pharmaceutically acceptable salt thereof. Also preferably, Compound 1 is selected from Table 3. Also preferably, Compound 1 is selected from Table 4.

In any method described herein, the patient being treated can be an interferon null-responder. Preferably, Compound 1 is the compound of Example 3 or a pharmaceutically acceptable salt thereof. Also preferably, Compound 1 is the compound of Example 5 or a pharmaceutically acceptable salt thereof. Also preferably, Compound 1 is the compound of Example 6 or a pharmaceutically acceptable salt thereof. Also preferably, Compound 1 is the compound of Example 7 or a pharmaceutically acceptable salt thereof. Also preferably, Compound 1 is the compound of Example 41 or a pharmaceutically acceptable salt thereof. Also preferably, Compound 1 is the compound of Example 1 or a pharmaceutically acceptable salt thereof. Also preferably, Compound 1 is selected from Table 3. Also preferably, Compound 1 is selected from Table 4.

In any method described herein, the patient being treated can be without cirrhosis. Preferably, Compound 1 is the compound of Example 3 or a pharmaceutically acceptable salt thereof. Also preferably, Compound 1 is the compound of Example 5 or a pharmaceutically acceptable salt thereof. Also preferably, Compound 1 is the compound of Example 6 or a pharmaceutically acceptable salt thereof. Also preferably, Compound 1 is the compound of Example 7 or a pharmaceutically acceptable salt thereof. Also preferably, Compound 1 is the compound of Example 41 or a pharmaceutically acceptable salt thereof. Also preferably, Compound 1 is the compound of Example 1 or a pharmaceutically acceptable salt thereof. Also preferably, Compound 1 is selected from Table 3. Also preferably, Compound 1 is selected from Table 4.

In any method described herein, the patient being treated can be a cirrhotic patient. Preferably, Compound 1 is the compound of Example 3 or a pharmaceutically acceptable salt thereof. Also preferably, Compound 1 is the compound of Example 5 or a pharmaceutically acceptable salt thereof. Also preferably, Compound 1 is the compound of Example 6 or a pharmaceutically acceptable salt thereof. Also preferably, Compound 1 is the compound of Example 7 or a pharmaceutically acceptable salt thereof. Also preferably, Compound 1 is the compound of Example 41 or a pharmaceutically acceptable salt thereof. Also preferably, Compound 1 is the compound of Example 1 or a pharmaceutically acceptable salt thereof. Also preferably, Compound 1 is selected from Table 3. Also preferably, Compound 1 is selected from Table 4.

In any method described herein, the patient being treated can be a patient with compensated cirrhosis. Preferably, Compound 1 is the compound of Example 3 or a pharmaceutically acceptable salt thereof. Also preferably, Compound 1 is the compound of Example 5 or a pharmaceutically acceptable salt thereof. Also preferably, Compound 1 is the compound of Example 6 or a pharmaceutically acceptable salt thereof. Also preferably, Compound 1 is the compound of Example 7 or a pharmaceutically acceptable salt thereof. Also preferably, Compound 1 is the compound of Example 41 or a pharmaceutically acceptable salt thereof. Also preferably, Compound 1 is the compound of Example 1 or a pharmaceutically acceptable salt thereof. Also preferably, Compound 1 is selected from Table 3. Also preferably, Compound 1 is selected from Table 4.

In any method, aspect, embodiment, example and preference described herein, Compound 1 preferably is the compound of Example 3 or a pharmaceutically acceptable salt thereof.

In any method, aspect, embodiment, example and preference described herein, Compound 1 preferably is the compound of Example 5 or a pharmaceutically acceptable salt thereof.

In any method, aspect, embodiment, example and preference described herein, Compound 1 preferably is the compound of Example 6 or a pharmaceutically acceptable salt thereof.

In any method, aspect, embodiment, example and preference described herein, Compound 1 preferably is the compound of Example 7 or a pharmaceutically acceptable salt thereof.

In any method, aspect, embodiment, example and preference described herein, Compound 1 preferably is the compound of Example 41 or a pharmaceutically acceptable salt thereof.

In any method, aspect, embodiment, example and preference described herein, Compound 1 preferably is selected from Table 3

In any method, aspect, embodiment, example and preference described herein, Compound 1 preferably is selected from Table 4.

In any method, aspect, embodiment, example and preference described herein, Compound 1 preferably is the compound of Example 1 or a pharmaceutically acceptable salt thereof.

Any compound of Formula VII, VIII, IX, A, A', A" and B as described herein, or any like phosphoramidate prodrug of Formula III', can be prepared by reacting

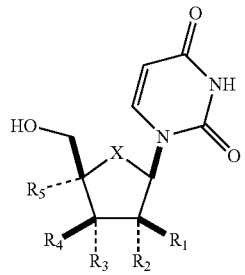

with

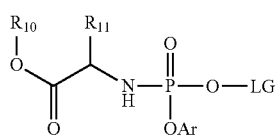

(hereinafter "phosphoramidate prodrug moiety compound"), wherein X, $R_1$, $R_2$, $R_3$, $R_4$ and $R_5$ are as defined in Table 1, wherein $R_{10}$ and $R_{11}$ are each independently $C_1$-$C_6$alkyl, $C_2$-$C_6$alkenyl or $C_2$-$C_6$alkynyl, and Ar is phenyl or naphthyl, and LG is a leaving group which can be selected, for example but not limited to, from one of the following moieties:

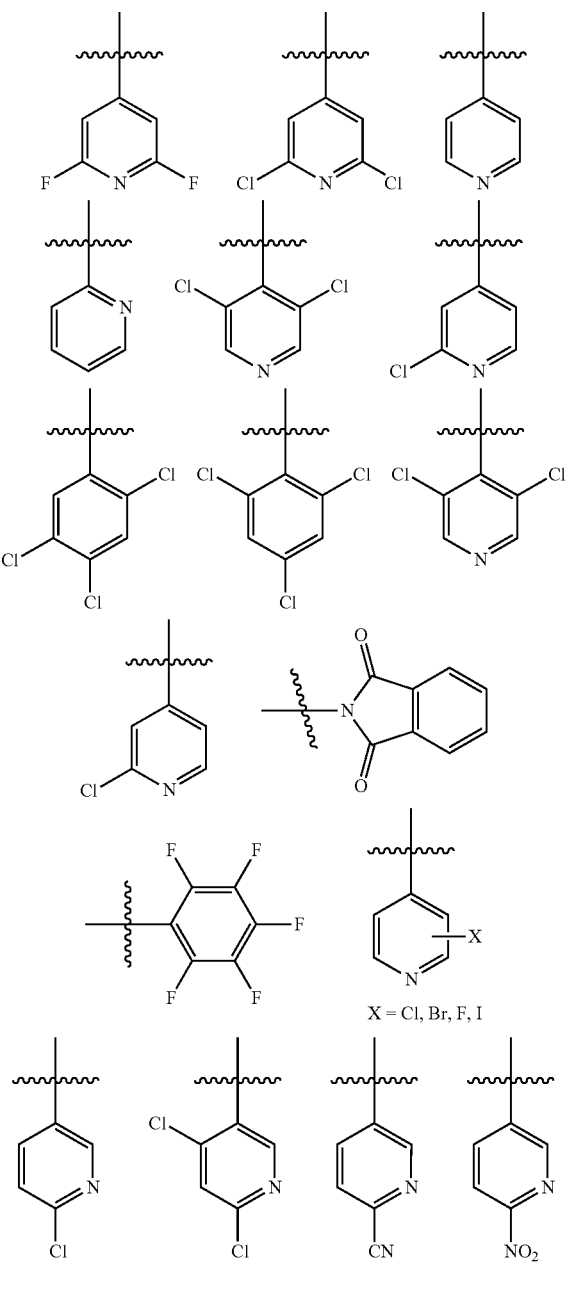

X = Cl, Br, F, I

LG can also be another suitable leaving group.

Any compound of Formula VII and VIII as described herein can be prepared by reacting

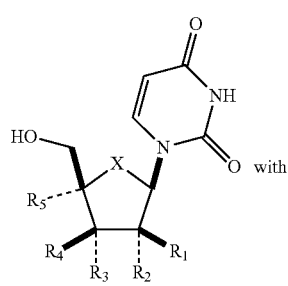 with

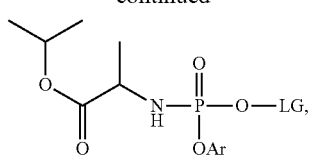

wherein X, $R_1$, $R_2$, $R_3$, $R_4$ and $R_5$ are as defined in Table 1, and Ar is phenyl, and LG is a leaving group which can be selected, for example but not limited to, from one of the following moieties:

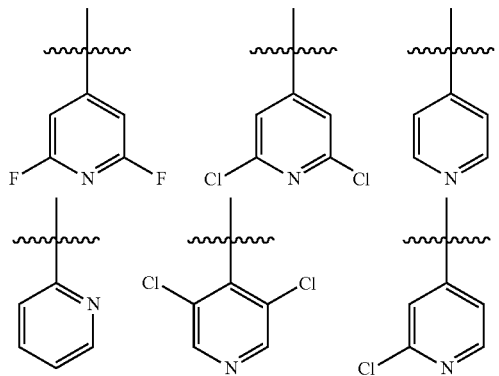

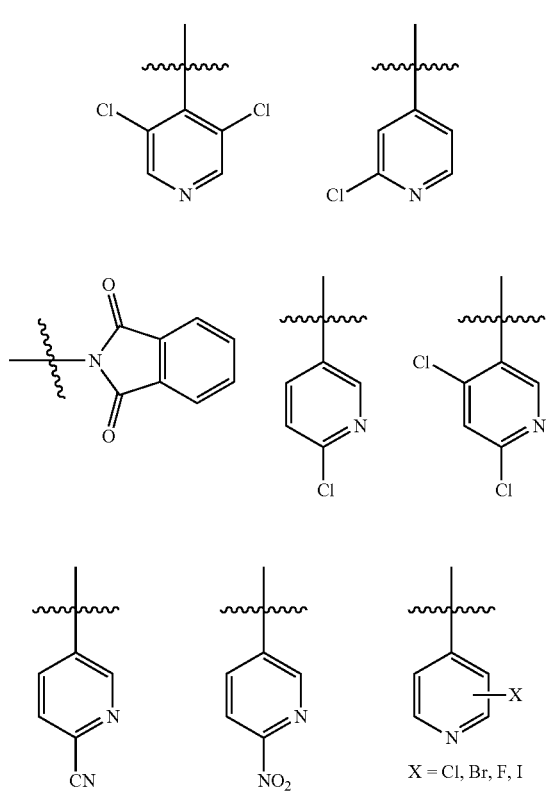

LG can also be another suitable leaving group.

Any compound of Formula VII, VIII, IX, A, A', A" and B as described herein, or any like phosphoramidate prodrug of Formula III', can be prepared by reacting

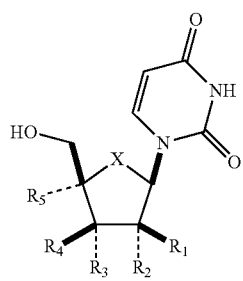

with

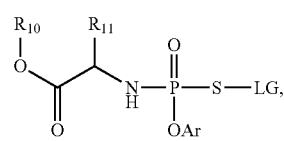

wherein X, $R_1$, $R_2$, $R_3$, $R_4$ and $R_5$ are as defined in Table 1, wherein $R_{10}$ and $R_{11}$ are each independently $C_1$-$C_6$alkyl, $C_2$-$C_6$alkenyl or $C_2$-$C_6$alkynyl, and Ar is phenyl or naphthyl, and LG is a leaving group which can be selected, for example but not limited to, from one of the following moieties:

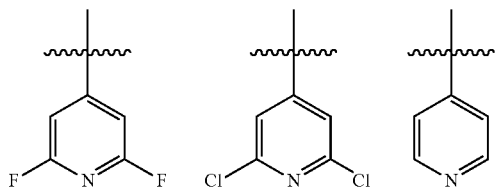

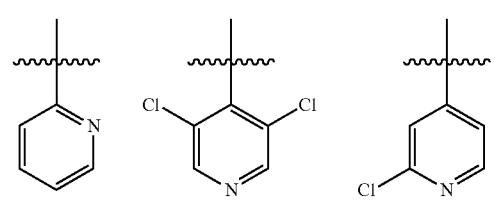

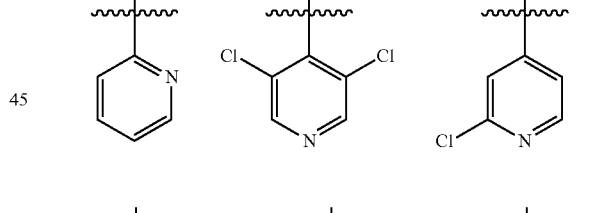

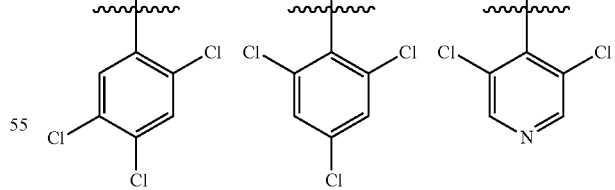

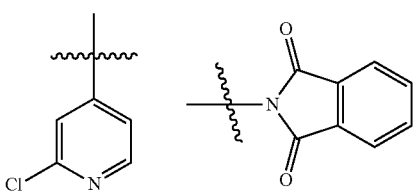

-continued

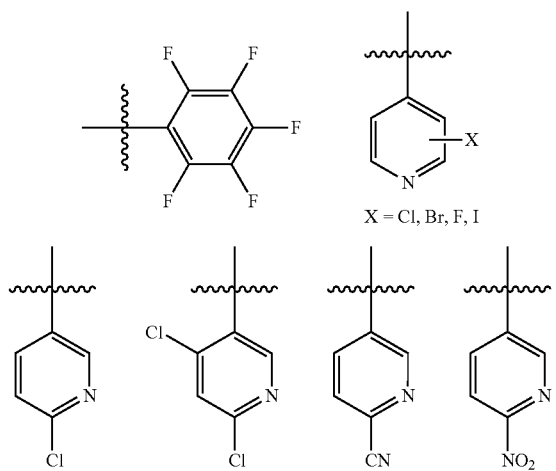

LG can also be another suitable leaving group.

Any compound of Formula VII and VIII as described herein can be prepared by reacting

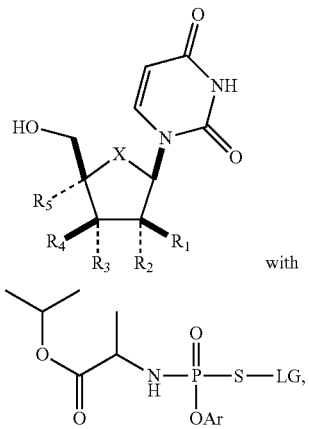

wherein X, $R_1$, $R_2$, $R_3$, $R_4$ and $R_5$ are as defined in Table 1, and Ar is phenyl, and LG is a leaving group which can be selected, for example but not limited to, from one of the following moieties:

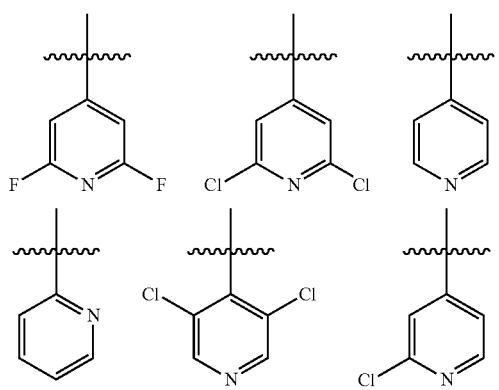

-continued

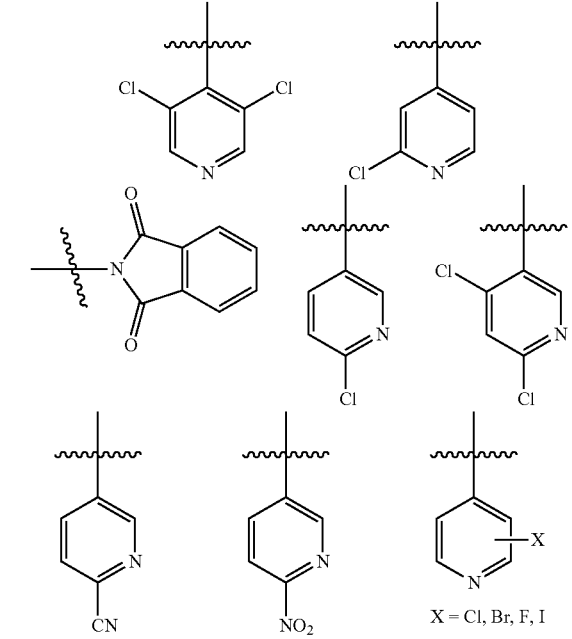

LG can also be another suitable leaving group.

When tested against HCV genotype 1a-H77,

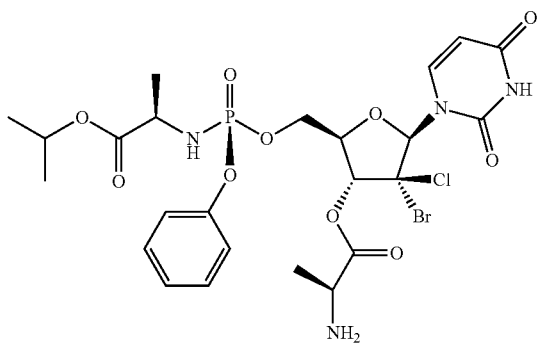 [SMILES: CC(C)OC(=O)[C@@H](C)N[P@](=O)(OC[C@H]1O[C@@H](n2ccc(=O)[nH]c2=O)[C@](Cl)(Br)[C@@H]1OC(=O)[C@H](C)N)Oc1ccccc1]

showed an $EC_{50}$ value of 113 nM. When tested against HCV genotype 1b-Con1, the same compound showed an $EC_{50}$ value of 140 nM. The therapeutic index ($TD_{50}/EC_{50}$) of this compound, as measured in 1a-H77 replicon cells, was over 284-fold.

When tested against HCV genotype 1a-H77,

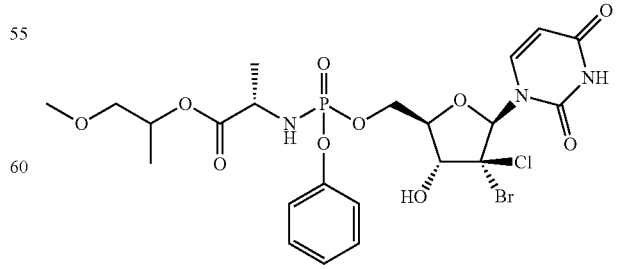

showed an $EC_{50}$ value of 390 nM. When tested against HCV genotype 1b-Con1, the same compound showed an $EC_{50}$ value of 368 nM. The therapeutic index (TD$_{50}$/EC$_{50}$) of this compound, as measured in 1a-H77 replicon cells, was over 256-fold.

When tested against HCV genotype 1a-H77,

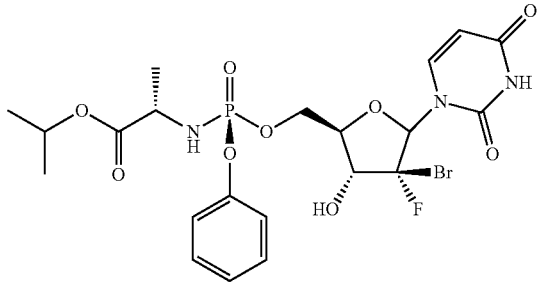 [SMILES: CC(C)OC(=O)[C@H](C)N[P@](=O)(OC[C@H]1OC(n2ccc(=O)[nH]c2=O)[C@@](F)(Br)[C@@H]1O)Oc1ccccc1]

showed an EC$_{50}$ value of 56 nM. When tested against HCV genotype 1b-Con1, the same compound showed an EC$_{50}$ value of about 87 nM. The therapeutic index (TD$_{50}$/EC$_{50}$) of this compound, as measured in 1a-H77 replicon cells, was over 576-fold.

When tested against HCV genotype 1a-H77,

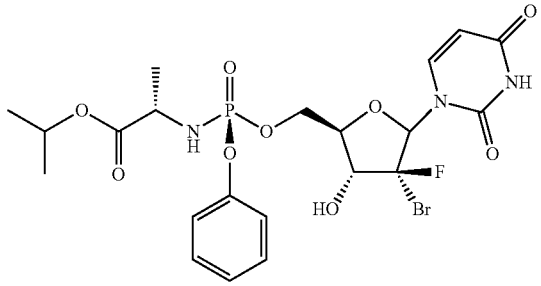 [SMILES: CC(C)OC(=O)[C@H](C)N[P@](=O)(OC[C@H]1OC(n2ccc(=O)[nH]c2=O)[C@](F)(Br)[C@@H]1O)Oc1ccccc1]

showed an EC$_{50}$ value of about 3000 nM. When tested against HCV genotype 1b-Con1, the same compound showed an EC$_{50}$ value of about 2500 nM. The therapeutic index (TD$_{50}$/EC$_{50}$) of this compound, as measured in 1a-H77 replicon cells, was 9-fold.

When tested against HCV genotype 1a-H77,

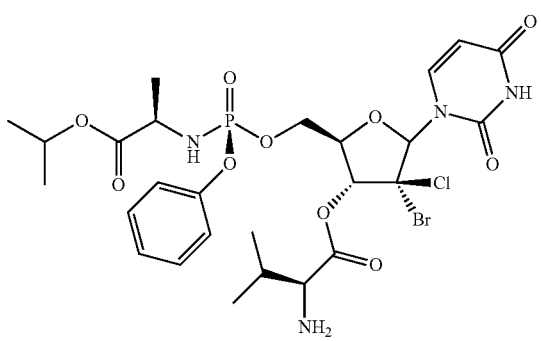 [SMILES: CC(C)OC(=O)[C@@H](C)N[P@](=O)(OC[C@H]1OC(n2ccc(=O)[nH]c2=O)[C@](Cl)(Br)[C@@H]1OC(=O)[C@@H](N)C(C)C)Oc1ccccc1]

showed an EC$_{50}$ value of 141 nM. When tested against HCV genotype 1b-Con1, the same compound showed an EC$_{50}$ value of 158 nM. The therapeutic index (TD$_{50}$/EC$_{50}$) of this compound, as measured in 1a-H77 replicon cells, was 709-fold.

When tested against HCV genotype 1a-H77,

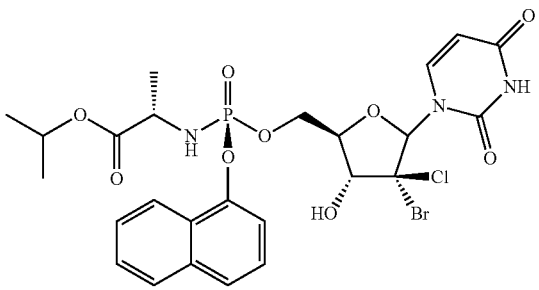 [SMILES: CC(C)OC(=O)[C@H](C)N[P@](=O)(OC[C@H]1OC(n2ccc(=O)[nH]c2=O)[C@](Cl)(Br)[C@@H]1O)Oc1cccc2ccccc12]

showed an EC$_{50}$ value of 106 nM. When tested against HCV genotype 1b-Con1, the same compound showed an EC$_{50}$ value of 139 nM. The therapeutic index (TD$_{50}$/EC$_{50}$) of this compound, as measured in 1a-H77 replicon cells, was about 360-fold.

When tested against HCV genotype 1a-H77,

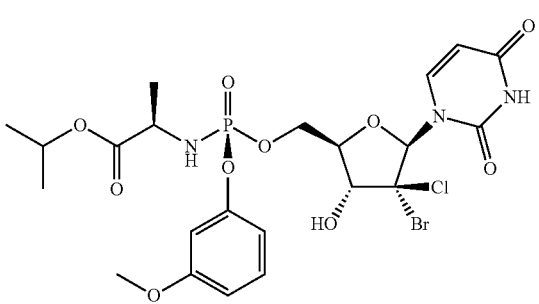 [SMILES: COc1cccc(O[P@](=O)(N[C@H](C)C(=O)OC(C)C)OC[C@H]2O[C@@H](n3ccc(=O)[nH]c3=O)[C@](Cl)(Br)[C@@H]2O)c1]

showed an EC$_{50}$ value of 181 nM. When tested against HCV genotype 1b-Con1, the same compound showed an EC$_{50}$ value of 226 nM. The therapeutic index (TD$_{50}$/EC$_{50}$) of this compound, as measured in 1a-H77 replicon cells, was 551-fold.

When tested against HCV genotype 1a-H77,

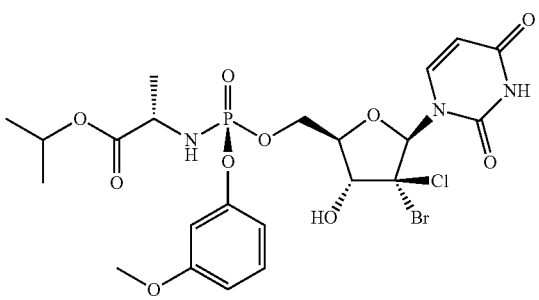 [SMILES: COc1cccc(O[P@](=O)(N[C@@H](C)C(=O)OC(C)C)OC[C@H]2O[C@@H](n3ccc(=O)[nH]c3=O)[C@](Cl)(Br)[C@@H]2O)c1]

showed an EC$_{50}$ value of 98 nM. When tested against HCV genotype 1b-Con1, the same compound showed an EC$_{50}$ value of 127 nM. The therapeutic index (TD$_{50}$/EC$_{50}$) of this compound, as measured in 1a-H77 replicon cells, was over 149-fold.

When tested against HCV genotype 1a-H77,

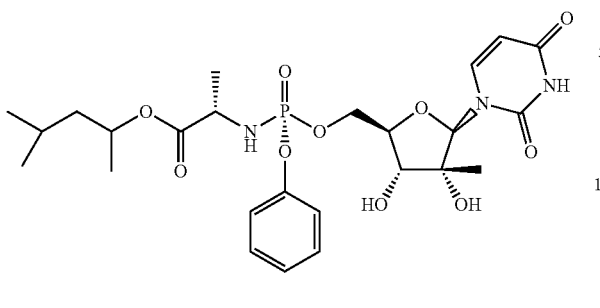

showed an $EC_{50}$ value of 13 nM. When tested against HCV genotype 1b-Con1, the same compound showed an $EC_{50}$ value of 29 nM. The therapeutic index ($TD_{50}/EC_{50}$) of this compound, as measured in 1a-H77 replicon cells, was about 2049-fold.

When tested against HCV genotype 1a-H77,

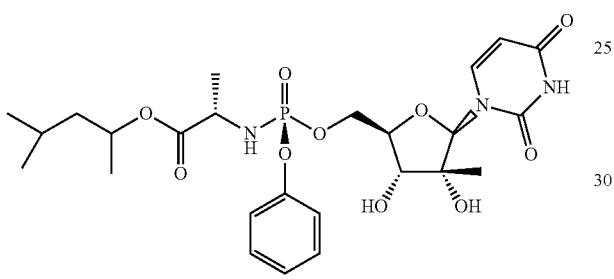

showed an $EC_{50}$ value of 1200 nM. When tested against HCV genotype 1b-Con1, the same compound showed an $EC_{50}$ value of 977 nM. The therapeutic index ($TD_{50}/EC_{50}$) of this compound, as measured in 1a-H77 replicon cells, was over 82-fold.

When tested against HCV genotype 1a-H77,

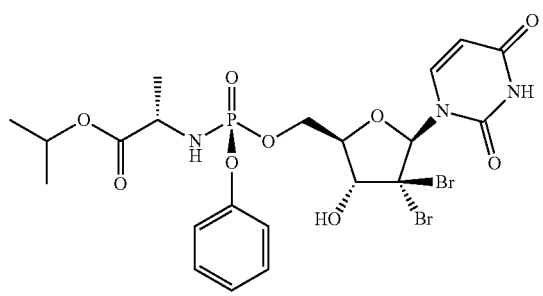

showed an $EC_{50}$ value of 480 nM. When tested against HCV genotype 1b-Con1, the same compound showed an $EC_{50}$ value of 522 nM. The therapeutic index ($TD_{50}/EC_{50}$) of this compound, as measured in 1a-H77 replicon cells, was over 245-fold.

It should be understood that the above-described embodiments and the following examples are given by way of illustration, not limitation. Various changes and modifications within the scope of the present invention will become apparent to those skilled in the art from the present description.

Example 1. (S)-isopropyl 2-(((S)-(((2R,3R,4R,5R)-4-bromo-4-chloro-5-(2,4-dioxo-3,4-dihydropyrimidin-1(2H)-yl)-3-hydroxytetrahydrofuran-2-yl)methoxy)(phenoxy)phosphoryl)amino) propanoate

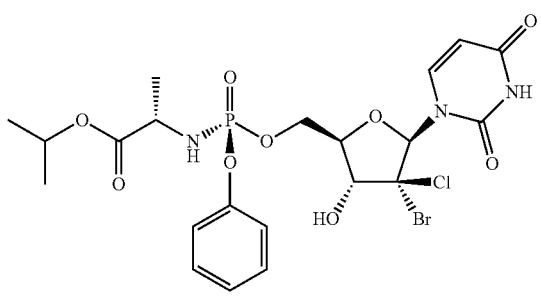 [SMILES: CC(C)OC(=O)[C@H](C)N[P@](=O)(OC[C@H]1O[C@@H](n2ccc(=O)[nH]c2=O)[C@](Cl)(Br)[C@@H]1O)Oc1ccccc1]

Example 1A. (4S,5R)-4-hydroxy-5-(hydroxymethyl)dihydrofuran-2(3H)-one

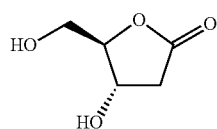

A 500 mL round-bottomed flask was charged with 2-deoxy-D-ribose (10 g, 74.6 mmol) and water (60 mL), followed by the dropwise addition of bromine (59.6 g, 373 mmol). The contents were then stirred at room temperature for 5 days. The reaction mixture was then diluted with water (300 mL) and then extracted with tert-butyl methyl ether (3×200 mL). The aqueous layer was then neutralized with the addition of silver carbonate until the pH of the aqueous solution reached 6. The resulting solids were removed by filtration and the filtrate was concentrated under vacuum to provide a residue which was dissolved in ethyl acetate (200 mL), followed by the addition of magnesium sulfate. After sitting overnight, the solids were filtered off and the filtrate was concentrated to provide the title compound as an oil (7.72 g, 78%). $^1$H NMR (400 MHz, $CDCl_3$) δ 1.83 (t, J=5.9 Hz, 1H), 2.13 (d, J=4.3 Hz, 1H), 2.57 (dd, J=18.1, 4.0 Hz, 1H), 3.00 (dd, J=18.0, 7.2 Hz, 1H), 3.85 (m, 1H), 3.97 (m, 1H), 4.46 (q, J=3.2 Hz, 1H), 4.65 (m, 1H).

Example 1B. (4S,5R)-4-((triisopropylsilyl)oxy)-5-(((triisopropylsilyl)oxy)methyl)dihydrofuran-2(3H)-one

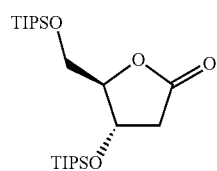

A 250 mL round-bottomed flask was charged with the product of Example 1A (7.5 g, 56.8 mmol) and N,N-dimethylformamide (50 mL), followed by the addition of triisopropylsilyl chloride (30.1 mL, 142 mmol) and 4-(dimethylamino)pyridine (0.35 g, 2.84 mmol). The contents were then stirred at room temperature for 16 hrs. To the reaction mixture was then added a solution of aqueous hydrochloric acid (0.5 N, 300 mL) followed by extraction with ethyl acetate (3×200 mL). The combined organic extracts were dried over magnesium sulfate, and filtered. The filtrate was then concentrated and the residue purified by column chromatography using a 220 g silica gel column, eluting with 0-25% ethyl acetate in heptanes to provide 21.8 g (86%) of the title compound. $^1$H NMR (400 MHz, CDCl$_3$) δ 1.04 (m, 42H), 2.47 (dd, J=17.6, 2.0 Hz, 1H), 2.92 (dd, J=17.6, 6.6 Hz, 1H), 3.91 (dd, J=11.4, 2.4 Hz, 1H), 3.96 (dd, J=11.3, 3.0 Hz, 1H), 4.44 (m, 1H), 4.69 (m, 1H).

Example 1C. (4R,5R)-3-chloro-4-((triisopropylsilyl)oxy)-5-(((triisopropylsilyl)oxy)methyl) dihydrofuran-2(3H)-one

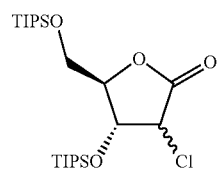

Dry (4R,5S)-4-((triisopropylsilyl)oxy)-5-(((triisopropylsilyl)oxy)methyl)dihydrofuran-2(3H)-one (Example 1B) (1.54 g, 3.46 mmol) was azeotroped with toluene (2×20 mL) and concentrated to dryness. The dry material was then dissolved in dichloromethane (20 mL) followed by addition of triethylamine (2.90 mL, 20.77 mmol) and cooled to 0° C. Trimethylsilyltrifluoromethanesulfonate (1.877 ml, 10.39 mmol) was added dropwise and allowed to stir for 30 min at 0° C. 2-chloro-1,3-bis(methoxycarbonyl)guanidine (Palau'Chlor) (0.878 g, 3.98 mmol) was dissolved in 12 mL of dichloromethane and added via syringe dropwise over 15 min resulting in a pale yellow solution. Gradually the reaction developed a darker yellow color over 15-20 min. Thin layer chromatography visualization (PMA+) after 90 min in 5% ethyl acetate/heptanes showed most starting material was consumed with two spots nearly co-eluting which likely are corresponding chloro anomers. Saturated sodium bicarbonate solution was added and diluted with ethyl acetate with stirring. Filtered off undissolved solid washing well with ethyl acetate. Filtrate separated, washed with brine, dried over magnesium sulfate, filtered and concentrated. The residue was further diluted a second time with 1:1 dichloromethane/heptanes and filtered the undissolved material washing with same solvent mixture and concentrating filtrate to give a yellow-orange oil. Material was purified on a 80 g silica gel column eluting with 0-10% ethyl acetate in heptanes. The desired product was collected which exhibited a weak UV signature (254 nM) as a broad peak around 20 min (0.89 g, 53.6%). MS (DCI (+) m/e 496 (M+NH$_4$).

Example 1D. (3R,4R,5R)-3-bromo-3-chloro-4-((triisopropylsilyl)oxy)-5-(((triisopropylsilyl)oxy)methyl)dihydrofuran-2(3H)-one

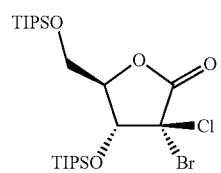

Dry (4R,5R)-3-chloro-4-((triisopropylsilyl)oxy)-5-(((triisopropylsilyl)oxy)methyl) dihydrofuran-2(3H)-one (1.49 g, 3.11 mmol) (Example 1C) was dissolved in dry tetrahydrofuran (10 ml, 0.3M)) followed by addition of N-bromosuccinimide (0.968 g, 5.44 mmol) and cooled to −78° C. resulting in a suspension. Lithium bis(trimethylsilyl) amide (5.44 mL, 5.44 mmol, 1M) was then added dropwise via syringe over 10 min yielding a thick yellow solution. The resultant mixture was kept at −78° C. for 45 minutes and was still turbid albeit more free flowing. Thin layer chromatography aliquot was quenched with methanol and showed a higher R$_f$ product from that of starting chloroketone with starting material consumed. Thin layer chromatography in 10% ethyl acetate/heptanes was visualized with PMA stain. Let reaction go for 1 hour then quenched with 1 ml of methanol followed by addition of saturated ammonium chloride and allowed to warm to room temp and extracted with ethyl acetate three times, washed with brine, back extracted aqueous layer with ethyl acetate and pooled organics, and dried over magnesium sulfate, filtered and concentrated. Dissolved residue in dichloromethane and loaded onto a 40 g silica gel column eluting with 0-10% ethyl acetate/heptanes. The desired product was collected and concentrated to give a lite yellow viscous oil (1.64 g, 2.64 mmol, 85%). $^1$H NMR (400 MHz, CDCl$_3$) δ 4.75 (d, J=7.6 Hz, 1H), 4.24-4.10 (m, 2H), 3.99 (dd, J=12.5, 1.9 Hz, 1H), 1.32-0.97 (m, 42H). MS (DCI (+) m/e 576 (M+NH$_4$).

Example 1E. (3R,4R,5R)-3-bromo-3-chloro-4-((triisopropylsilyl)oxy)-5-(((triisopropylsilyl)oxy)methyl)tetrahydrofuran-2-ol

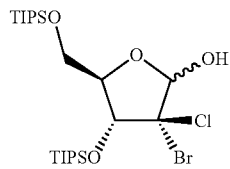

Dry (3R,4R,5R)-3-bromo-3-chloro-4-((triisopropylsilyl)oxy)-5-(((triisopropylsilyl)oxy) methyl)dihydrofuran-2(3H)-one (1.64 g, 2.94 mmol) (Example 1D) was dissolved in toluene (25 ml) under N$_2$ and cooled to −78° C. Diisopropylaluminumhydride in toluene (23.51 ml, 23.51 mmol, 1M) added via syringe slowly and reaction was stirred for 1 h and was done after this time by thin layer chromatography 5% ethyl acetate in heptanes visualized with PMA+ stain to give a more polar spot as major with several minor spots which were faint with PMA stain. The reaction was then quenched at −78° C. with saturated Rochelle's Salt and then allowed to warm slowly to ambient temperature and added ethyl acetate to give biphasic turbid mixture which was stirred overnight. After stirring overnight reaction was now a clear biphasic mixture which was transferred to separatory funnel and the organic layer separated. Aqueous phase was extracted two times with ethyl acetate, and combined organics where dried over magnesium sulfate, filtered and concentrated and dried to give a lite yellow oil as the desired product (1.65 g, 2.95 mmol, 95% yield). NMR shows anomer mixture as expected but was not purified further. MS (DCI (+) m/e 578 (M+NH$_4$).

Example 1F. (3R,4R,5R)-3-bromo-3-chloro-4-((triisopropylsilyl)oxy)-5-(((triisopropylsilyl)oxy)methyl)tetrahydrofuran-2-yl methanesulfonate

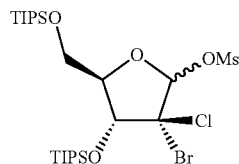

Dry (3R,4R,5R)-3-bromo-3-chloro-4-((triisopropylsilyl)oxy)-5-(((triisopropylsilyl)oxy) methyl)tetrahydrofuran-2-ol (0.730 g, 1.303 mmol) (Example 1E) was dissolved in dichloromethane (15 mL) followed by addition of triethylamine (0.636 mL, 4.56 mmol) and cooled to 0° C. Methanesulfonyl chloride (0.256 mL, 3.26 mmol) was added dropwise via syringe and after stirring for 20 min at 0° C. the reaction was warmed to ambient temperature overnight. Reaction after this time was a turbid yellow/orange. Diluted with ethyl acetate and washed with 1N HCl, followed by saturated sodium bicarbonate, and brine. Dried over magnesium sulfate, filtered and concentrated to give a yellow oil as the desired product (0.825 g, 1.293 mmol, 99% yield) as a brownish yellow oil. as a mixture of mesylate anomers which was used as is without further purification.

Example 1G. N-(1-((2R,3R,4R,5R)-3-bromo-3-chloro-4-((triisopropylsilyl)oxy)-5-(((triisopropylsilyl)oxy)methyl)tetrahydrofuran-2-yl)-2-oxo-1,2-dihydropyrimidin-4-yl)benzamide

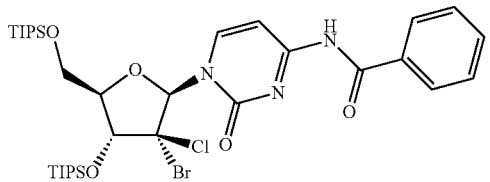

N-(2-oxo-1,2-dihydropyrimidin-4-yl)benzamide (1.902 g, 8.84 mmol) was suspended in dichloroethane (20 mL) in a dry round bottom flask under nitrogen atmosphere followed by addition of N,O-bis(trimethylsilyl)acetamide (2.397 g, 11.78 mmol) and heated to reflux for 2 h yielding a homogeneous solution. Cooled after heating to ambient temperature. Dry (3R,4R,5R)-3-bromo-3-chloro-4-((triisopropylsilyl)oxy)-5-(((triisopropylsilyl)oxy)methyl)tetrahydrofuran-2-yl methanesulfonate (1.88 g, 2.95 mmol), (Example 1F) was dissolved in dichloroethane (20 mL) and added to above solution after cooling to 0° C. and under nitrogen. Tin tetrachloride (1.535 g, 5.89 mmol) was then added dropwise to above cooled solution. After addition the reaction was warmed to ambient temperature followed by heating at 70° C. for 16 h resulting in a dark brown solution. Thin layer chromatography in 30% ethyl acetate/heptanes visualized at 254 nM shows ~1:2 ratio of alpha/beta anomers. Added saturated sodium bicarbonate (15 ml) to give a turbid mixture. Diluted with ethyl acetate and filtered through a celite plug washing well with ethyl acetate. Filtrate transferred to a separatory funnel and washed again with saturated sodium bicarbonate solution, brine and organics dried over magnesium sulfate, filtered and concentrated. Dissolved residue in dichloromethane and loaded onto a 120 g silica gel column eluting with 0-40% ethyl acetate in heptanes. Observed chromatographic peak ratio of about 1:2 for alpha, beta anomers respectively which were separated to give the beta anomer as a white solid, (0.570 g, 25.6%). $^1$H NMR (400 MHz, DMSO-$d_6$) δ 11.52-11.26 (m, 1H), 8.24 (d, J=7.7 Hz, 1H), 7.98 (d, 2H), 7.62 (t, J=7.3 Hz, 1H), 7.50 (t, J=7.7 Hz, 2H), 7.39 (d, J=7.6 Hz, 1H), 6.84 (s, 1H), 4.33 (d, 1H), 4.20 (d, J=12.4 Hz, 1H), 3.98 (dd, J=20.0, 10.4 Hz, 2H), 1.25-0.98 (m, 42H). MS (ESI (+) m/e 758 (M+1).

Example 1H. 1-((2R,3R,4R,5R)-3-bromo-3-chloro-4-hydroxy-5-(hydroxymethyl)tetrahydrofuran-2-yl)pyrimidine-2,4(1H,3H)-dione

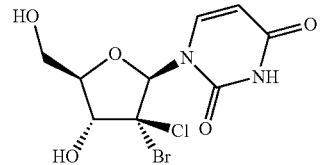 [SMILES: O=c1ccn([C@@H]2O[C@H](CO)[C@@H](O)[C@@]2(Cl)Br)c(=O)[nH]1]

A 50 mL round-bottomed flask was charged with the product of Example 1G (560 mg, 0.739 mmol) and acetic acid (8.47 mL, 148 mmol), followed by water (1.33 mL, 74 mmol) were added and then the flask was heated at 110° C. for 14 hrs. After cooling to room temperature, the solution was concentrated to an oil and then triturated with toluene two times and then the residue used directly in the next reaction. The material was then dissolved in methanol (20 mL) and then ammonium fluoride (226 mg, 6.11 mmol) added and the mixture heated at 60° C. for 17 hrs. After cooling to room temperature, the reaction mixture was then was then concentrated and the residue purified by column chromatography using a silica gel column, eluting with 0-25% methanol in dichloromethane to provide 77 mg (37%) of the crude title compound. The material was then purified again using supercritical fluid chromatography (SFC) on a chiral column. Preparative SFC was performed on a THAR/Waters SFC 80 system running under SuperChrom software control. The preparative SFC was equipped with a 8-way column switcher, CO2 pump, modifier pump, automated back pressure regulator (ABPR), UV detector, and 6-position fraction collector. The mobile phase comprised of supercritical CO2 supplied by a dewar of bone-dry non-certified CO2 pressurized to 350 psi with a modifier of methanol at a flow rate of 70 g/min. The column was at ambient temperature and the backpressure regulator was set to maintain 100 bar. The sample was dissolved in methanol at a concentration of 19.25 mg/mL and was loaded into the modifier stream in 100 μL (~2 mg) injections. The mobile phase was held isocratically at 20% methanol:CO2. Fraction collection was time triggered. The instrument was fitted with a ChiralCel OJ-H column with dimensions 21 mm I.D.×250 mm length with 5 μm particles. The retention time of the desired compound was from 2.05-2.30 minutes. This provided 41 mg of the title product in 97% purity. $^1$H NMR (400 MHz, DMSO-d6) δ 3.63 (m, 1H), 3.79 (m, 2H), 4.02 (d, J=8.7 Hz, 1H), 5.48 (s, 1H), 5.69 (d, J=8.2 Hz, 1H), 6.60 (s, 1H), 6.83 (s, 1H), 8.07 (d, J=8.3 Hz, 1H), 11.53 (s, 1H). MS ESI− m/z 341 (M−H)+.

Example 1I. (S)-isopropyl 2-(((S)-(((2R,3R,4R,5R)-4-bromo-4-chloro-5-(2,4-dioxo-3,4-dihydropyrimidin-1(2H)-yl)-3-hydroxytetrahydrofuran-2-yl)methoxy)(phenoxy)phosphoryl)amino) propanoate

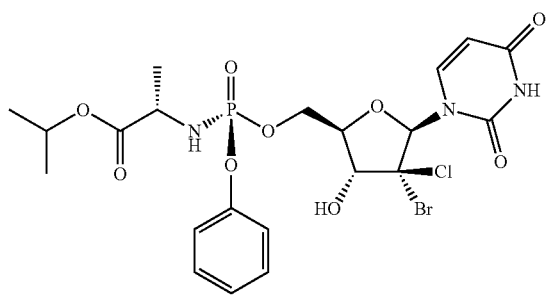 [SMILES: CC(C)OC(=O)[C@H](C)N[P@](=O)(OC[C@H]1O[C@@H](n2ccc(=O)[nH]c2=O)[C@](Cl)(Br)[C@@H]1O)Oc1ccccc1]

The product of Example 1H and the corresponding phosphoramidate prodrug moiety compound were mixed in a reaction flask. The contents were then stirred at room temperature for 3 hrs. The reaction mixture was extracted, and the combined organic extracts were dried and filtered. The filtrate was then concentrated and the residue purified by column chromatography using a silica gel column, eluting with 0-100% ethyl acetate in heptanes followed by a second column chromatography using a silica gel column, eluting with 0-5% methanol in dichloromethane to provide 41 mg (60%) of the title compound. $^1$H NMR (400 MHz, DMSO-d6) δ 1.14 (d, J=6.3 Hz, 6H), 1.21 (d, J=7.1 Hz, 3H), 3.79 (m, 1H), 4.00 (m, 1H), 4.08 (m, 1H), 4.30 (m, 2H), 4.84 (m, 1H), 5.56 (d, J=8.2 Hz, 1H), 6.08 (dd, J=13.1, 10.1 Hz, 1H), 6.62 (s, 1H), 6.99 (d, J=5.5 Hz, 1H), 7.20 (m, 3H), 7.36 (m, 2H), 7.63 (d, J=8.1 Hz, 1H), 11.58 (s, 1H). MS ESI+ m/z 612 (M+H)+.

When tested against HCV genotype 1a-H77, the compound of Example 1 showed an EC$_{50}$ value of 109 nM. When tested against HCV genotype 1b-Con1, the compound of Example 1 showed an EC$_{50}$ value of 208 nM. No cytotoxicity was observed during the study.

The therapeutic index (TD$_{50}$/EC$_{50}$) of the compound of Example 1, as measured in a toxicity study using 1a-H77 replicon cells, was about 788-fold.

Example 2. (S)-isopropyl 2-(((S)-(((2R,3R,4R,5R)-4-bromo-5-(2,4-dioxo-3,4-dihydropyrimidin-1(2H)-yl)-4-fluoro-3-hydroxytetrahydrofuran-2-yl)methoxy)(phenoxy)phosphoryl)amino) propanoate

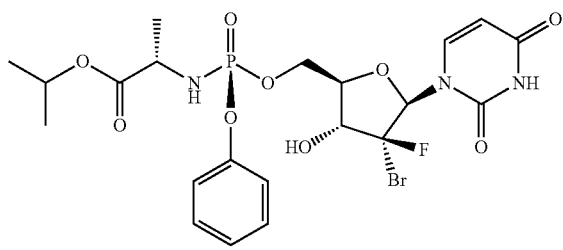 [SMILES: CC(C)OC(=O)[C@H](C)N[P@](=O)(OC[C@H]1O[C@@H](n2ccc(=O)[nH]c2=O)[C@](F)(Br)[C@@H]1O)Oc1ccccc1]

Example 2A. (4R,5R)-3-fluoro-4-((triisopropylsilyl)oxy)-5-(((triisopropylsilyl)oxy)methyl) dihydrofuran-2(3H)-one

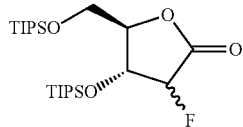

To (4S,5R)-4-((triisopropylsilyl)oxy)-5-(((triisopropylsilyl)oxy)methyl)dihydrofuran-2(3H)-one (5.466 g, 12.29 mmol) in tetrahydrofuran (THF) (40 mL) was added N-fluorobenzenesulfonimide (5.0562 g, 16.03 mmol), cooled to −78° C. A 1 M solution of lithium bis(trimethylsilyl)amide in toluene (13.5 mL, 13.50 mmol) was added dropwise over 20 minutes. Stirred for another 20 minutes. Quenched by dropwise addition of an aqueous solution of HCl (1 N, 20 mL) at −78° C., removed the bath, and heptane (40 mL) and HCl (1 N, 50 mL) were added. The mixture was stirred and warmed to room temperature. The layers were separated. The organic layer was washed with HCl (1 N, 40 mL), water (20 mL) and brine (20 mL). The combined aqueous layers were back-extracted with heptane (30 mL×2). The combined organic layers were dried (MgSO4) and concentrated. The residue was purified by flash chromatography using a Biotage® SNAP 340 g silica cartridge eluted with a gradient of 0-60% dichloromethane/heptane and gave the title compound (4.31 g, 8.79 mmol, 71.6% yield). $^1$H NMR (400 MHz, Chloroform-d) δ ppm 1.04-1.12 (m, 84H), 3.94 (dd, J=12.2, 2.4 Hz, 2H), 4.11 (dt, J=12.2, 2.1 Hz, 2H), 4.19 (dt, J=7.0, 2.3 Hz, 2H), 4.91 (t, J=7.2 Hz, 1H), 4.96 (t, J=7.2 Hz, 1H), 5.07 (d, J=7.4 Hz, 1H), 5.20 (d, J=7.4 Hz, 1H)

Example 2B. (3R,4R,5R)-3-bromo-3-fluoro-4-((triisopropylsilyl)oxy)-5-(((triisopropylsilyl)oxy)methyl)dihydrofuran-2(3H)-one

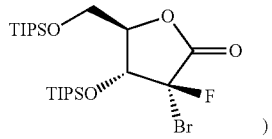

Example 2C. (3S,4R,5R)-3-bromo-3-fluoro-4-((triisopropylsilyl)oxy)-5-(((triisopropylsilyl)oxy)methyl)dihydrofuran-2(3H)-one

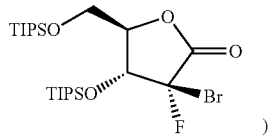

To a solution of the product of Example 2A (2.837 g, 6.13 mmol) in tetrahydrofuran (THF) (30 mL) was added N-bromosuccinimide (1.637 g, 9.20 mmol), cooled to −78° C. To the solution was added dropwise a 0.5 M solution of potassium bis(trimethylsilyl)amide in toluene (25 mL, 12.50 mmol) over 18 minutes. Stirred for 10 min. Quenched with an aqueous solution of 1N HCl (15 mL) at −78° C., removed the bath, more HCl (1 N, 35 mL) and heptane (50 mL) were added, warmed to room temperature. The layers were separated. The organic layer was washed with HCl (50 mL), water (30 mL), Na$_2$S$_2$O$_3$ (0.1 N, 50×2 mL) and brine (30 mL). The combined aqueous layers were back-extracted with heptane (50 mL). The combined organic layers were dried (MgSO4) and concentrated. The residue was purified by flash chromatography using a Biotage® SNAP 100 g silica cartridge eluted with a gradient of 0-5% ethyl acetate/heptane and gave the title compound Example 2B containing small amount of Example 2C (2.09 g, 3.86 mmol, 62.9% yield). $^1$H NMR (400 MHz, Chloroform-d) δ ppm 0.98-1.11 (m, 89H), 3.97 (dd, J=12.5, 1.9 Hz, 1H), 4.05 (dt, J=7.7, 1.9 Hz, 1H), 4.16 (dt, J=12.5, 2.3 Hz, 1H), 4.79 (dd, J=14.6, 7.7 Hz, 1H)

Example 2D. (3R,4R,5R)-3-bromo-3-fluoro-4-((triisopropylsilyl)oxy)-5-(((triisopropylsilyl)oxy)methyl)tetrahydrofuran-2-ol

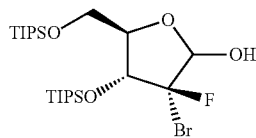

To a solution of the products of Examples 2B and 2C (2.09 g, 3.86 mmol) in toluene (12 mL) cooled to −78° C. was added dropwise a 1 M solution of DIBAL-H (4.3 mL, 4.30 mmol) in toluene. The solution was stirred at −78° C. for 1.5 hours. Quenched the reaction with a 10% aqueous solution of Rochelle's salt (20 mL) at −78° C., and the mixture was allowed to warm up. The mixture was filtered through a pad of Celite®, rinsed with methyl t-butyl ether. The layers of the filtrate were separated. The organic layer was washed with 1 N HCl (20 mL×2), water (15 mL) and brine (15 mL). Dried (MgSO4), concentrated and purified by flash chromatography using a Biotage® SNAP 100 g silica cartridge eluted with a gradient of 0-30% dichloromethane/heptane and gave the title compound (1.8052 g, 3.32 mmol, 86% yield). $^1$H NMR (501 MHz, Chloroform-d) δ ppm 1.04-1.21 (m, 59H), 3.48 (d, J=12.7 Hz, 0.4H), 3.77-3.84 (m, 2H), 3.86-3.91 (m, 2H), 3.94 (dt, J=6.6, 2.0 Hz, 1H), 4.08 (tdd, J=4.6, 3.5, 1.0 Hz, 0.4H), 4.67 (ddd, J=11.6, 4.6, 0.9 Hz, 0.4H), 4.72 (dd, J=12.8, 6.6 Hz, 1H), 5.17 (ddd, J=12.7, 5.9, 0.9 Hz, 0H), 5.34 (dd, J=9.2, 1.2 Hz, 1H)

Example 2E. (3R,4R,5R)-3-bromo-3-fluoro-4-((triisopropylsilyl)oxy)-5-(((triisopropylsilyl)oxy)methyl)tetrahydrofuran-2-yl benzoate

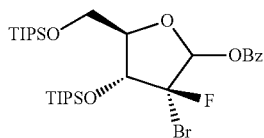

To a solution of the product of Example 2D (1.8052 g, 3.32 mmol) in pyridine (Py) (10 mL) was added N,N-dimethylpyridin-4-amine (0.041 g, 0.332 mmol) followed by dropwise addition of benzoyl chloride (0.56 mL, 4.82 mmol). The suspension was stirred at room temperature for 1 hour. The reaction mixture was concentrated at reduced pressure. The residue was purified by flash chromatography using a Biotage® SNAP 100 g silica cartridge eluted with a gradient of 0-35% dichloromethane/heptane and gave the title compound (2.15 g, 3.32 mmol, 100% yield). $^1$H NMR (400 MHz, Chloroform-d) δ ppm 0.95-0.99 (m, 24H), 1.17 (t, J=5.7 Hz, 22H), 3.86-3.95 (m, 2H), 4.03 (dt, J=11.9, 2.3 Hz, 1H), 4.84 (dd, J=12.3, 8.0 Hz, 1H), 6.69 (d, J=1.5 Hz, 1H), 7.47 (d, J=7.7 Hz, 2H), 7.61 (t, J=7.5 Hz, 1H), 8.02-8.06 (m, 2H)

Example 2F. (Z)—N-(1-((2R,3R,4R,5R)-3-bromo-3-fluoro-4-((triisopropylsilyl)oxy)-5-(((triisopropylsilyl)oxy)methyl)tetrahydrofuran-2-yl)-2-oxo-1,2-dihydropyrimidin-4-yl)benzimidic acid

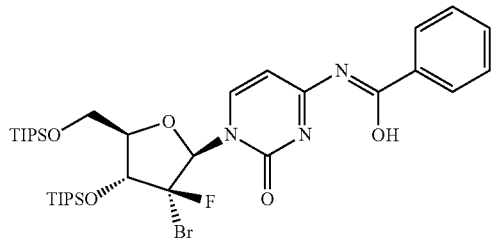

To a suspension of (Z)—N-(2-hydroxypyrimidin-4-yl)benzimidic acid (1.0089 g, 4.69 mmol) in chlorobenzene (5.5 mL) was added (E)-trimethylsilyl N-(trimethylsilyl)acetimidate (1.2 mL, 4.89 mmol). Stirred at 80° C. for 45 minutes, and cooled to room temperature.

To the product of Example 2E (1 g, 1.544 mmol) was cannulated the above solution of bis-silylated cytosine. To the resulting solution was added freshly distilled (114-116° C., 760 mmHg) perchlorostannane (0.73 mL, 6.22 mmol) at room temperature. The solution was stirred at 100° C. overnight. The reaction suspension was poured into an aqueous solution of NaHCO$_3$ (1 N, 40 mL) at room temperature. The reaction flask was rinsed with methyl t-butyl ether (15 mL) and added into the bicarbonate mixture. The mixture was stirred at room temperature for 1 hour, filtered through Celite®, rinsed with methyl t-butyl ether (50 mL). The layers of the filtrate were separated and the organic layer was washed with water (20 mL), 1 N HCl (15 mL) and brine (15 mL). The filter cake and the reaction flasks were rinsed with dichloromethane. The organic layers were combined, dried (MgSO4) and concentrated to give a light yellow oil, which was purified by flash chromatography using a RediSep® Rf gold 40 g silica cartridge eluted with a gradient of 0-25% ethyl acetate/heptane and gave the title compound as a white solid (654.2 mg, 0.883 mmol, 57.2% yield). $^1$H NMR (501 MHz, DMSO-d$_6$) δ ppm 1.08 (dt, J=7.4, 2.1 Hz, 37H), 1.12-1.22 (m, 5H), 3.95-4.01 (m, 2H), 4.12-4.17 (m, 1H), 4.48 (dd, J=15.6, 7.6 Hz, 1H), 6.65 (d, J=4.8 Hz, 1H), 7.41 (d, J=7.6 Hz, 1H), 7.50-7.55 (m, 2H), 7.64 (ddt, J=7.8, 6.9, 1.2 Hz, 1H), 7.99-8.03 (m, 2H), 8.21 (d, J=7.6 Hz, 1H), 11.43 (s, 1H)); MS (APCI) m/z 741.32 (M+H)$^+$.

Example 2G. 1-((2R,3R,4R,5R)-3-bromo-3-fluoro-4-hydroxy-5-(hydroxymethyl)tetrahydrofuran-2-yl)pyrimidine-2,4(1H,3H)-dione

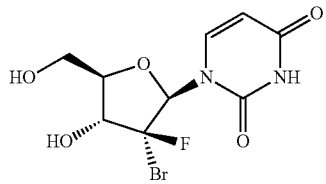 [SMILES: O=c1ccn([C@@H]2O[C@H](CO)[C@@H](O)[C@@]2(F)Br)c(=O)[nH]1]

To the product of Example 2F (86.8 mg, 0.117 mmol) was added acetic acid (AcOH) (0.6 mL) and water (0.15 mL). The suspension was stirred at 100° C. overnight. The solution was cooled to room temperature and concentrated. The residue was azeotroped with toluene and dissolved in methanol (MeOH) (0.3 mL). Ammonium fluoride (45.5 mg, 1.229 mmol) was added and the suspension was stirred at 60° C. overnight. Ammonia hydrofluoride (27 mg, 0.729 mmol) was added, stirred at 60° C. overnight and cooled to room temperature. The reaction mixture was diluted with dichloromethane, filtered and rinsed with 10% MeOH in dichloromethane. The filtrate was concentrated to a solid, which was purified by flash chromatography using a RediSep® Rf gold 12 g silica cartridge eluted with a gradient of 0-10% MeOH/dichloromethane and gave the title compound (33 mg, 0.102 mmol, 87% yield) as a white gummy solid after azeotroped with toluene. $^1$H NMR (501 MHz, DMSO-$d_6$) δ ppm 3.63 (ddd, J=12.5, 5.4, 3.3 Hz, 1H), 3.73-3.81 (m, 2H), 4.07-4.17 (m, 1H), 5.33 (t, J=5.3 Hz, 1H), 5.70 (d, J=8.2 Hz, 1H), 6.39 (d, J=7.7 Hz, 1H), 6.67 (d, J=6.0 Hz, 1H), 7.89 (dd, J=8.2, 1.6 Hz, 1H), 11.55 (s, 1H); MS (APCI+) m/z 326.27 (M+H)$^+$.

Example 2H. (S)-isopropyl 2-(((S)-(((2R,3R,4R,5R)-4-bromo-5-(2,4-dioxo-3,4-dihydropyrimidin-1(2H)-yl)-4-fluoro-3-hydroxytetrahydrofuran-2-yl)methoxy)(phenoxy)phosphoryl)amino)propanoate

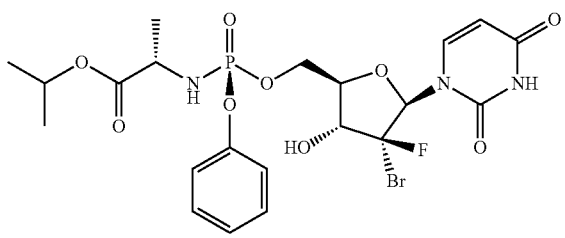 [SMILES: CC(C)OC(=O)[C@H](C)N[P@](=O)(OC[C@H]1O[C@@H](n2ccc(=O)[nH]c2=O)[C@](F)(Br)[C@@H]1O)Oc1ccccc1]

The product of Example 2G (42.55 mg, 0.094 mmol) was reacted with the corresponding phosphoramidate prodrug moiety compound. The resulting product was diluted with acetonitrile and purified on a reversed-phase Waters HPLC using a Nova-Pak® HR C18, 6 μm, 60 Å, 40 mm×100 mm, PrepPak cartridge eluting with a gradient of 20-90% acetonitrile in aqueous 0.1% trifluoroacetic acid (60 mL/minute) to give the titled (12.88 mg, 0.020 mmol, 43.4% yield) $^1$H NMR (501 MHz, DMSO-$d_6$) δ ppm 1.16 (d, J=6.3 Hz, 6H), 1.23 (dd, J=7.1, 0.9 Hz, 3H), 3.80 (td, J=10.2, 7.1 Hz, 1H), 4.02 (dt, J=5.8, 2.8 Hz, 1H), 4.16-4.26 (m, 1H), 4.31 (ddd, J=11.9, 6.6, 2.9 Hz, 1H), 4.86 (p, J=6.2 Hz, 1H), 5.61 (dd, J=8.2, 2.2 Hz, 1H), 6.07 (dd, J=13.1, 10.0 Hz, 1H), 6.41 (d, J=11.3 Hz, 1H), 6.83 (s, 1H), 7.18 (dd, J=7.3, 0.9 Hz, 1H), 7.21 (ddt, J=7.7, 2.3, 1.2 Hz, 2H), 7.35-7.40 (m, 2H), 7.56 (dd, J=8.1, 2.3 Hz, 1H), 11.60 (d, J=2.2 Hz, 1H); MS (ESI−) m/z 591.9 (M−H)$^-$.

Example 3. (S)-isopropyl 2-(((S)-(((2R,3R,4S,5R)-4-bromo-5-(2,4-dioxo-3,4-dihydropyrimidin-1(2H)-yl)-4-fluoro-3-hydroxytetrahydrofuran-2-yl)methoxy)(phenoxy)phosphoryl)amino)propanoate

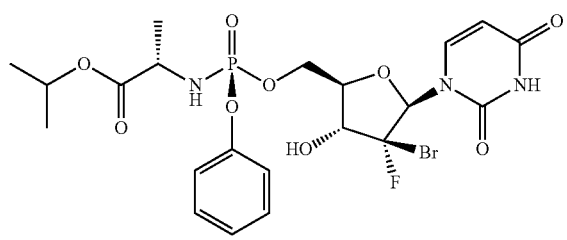 [SMILES: CC(C)OC(=O)[C@H](C)N[P@](=O)(OC[C@H]1O[C@@H](n2ccc(=O)[nH]c2=O)[C@@](F)(Br)[C@@H]1O)Oc1ccccc1]

Example 3A. (4R,5R)-3-bromo-3-fluoro-4-((triisopropylsilyl)oxy)-5-(((triisopropylsilyl)oxy) methyl)dihydrofuran-2(3H)-one

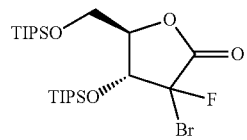

The titled compound was prepared using the conditions described in Examples 2B and 2C. Using the product of Example 2A (5.8357 g, 12.61 mmol) in tetrahydrofuran (THF) (55 mL), N-bromosuccinimide (2.69028 g, 15.12 mmol) and lithium bis(trimethylsilyl)amide (15.5 mL, 15.50 mmol), the title compound was obtained as a mixture of the products of Examples 2B and 2C in a ratio of 1/3.4 (5.9467 g, 9.88 mmol, 78% yield). $^1$H NMR (400 MHz, Chloroform-d) δ ppm 1.04-1.21 (m, 58H), 3.94-4.12 (m, 3H), 4.13-4.18 (m, 0.4H), 4.46 (ddd, J=6.4, 4.9, 2.5 Hz, 1H), 4.79 (dd, J=14.6, 7.7 Hz, 0.4H), 4.93 (dd, J=4.5, 2.8 Hz, 1H); MS (ESI+) m/z 541.0 (M+H)$^+$.

Example 3B. (3S,4R,5R)-3-bromo-3-fluoro-4-((triisopropylsilyl)oxy)-5-(((triisopropylsilyl)oxy)methyl)tetrahydrofuran-2-ol

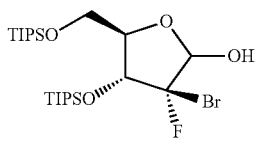

The titled compound was prepared using the conditions described in Example 2D. Using the product of Example 3A (6.0767 g, 11.22 mmol), the title compound was obtained as clean material (3.49 g, 6.42 mmol, 57.2% yield) and as a mixture containing the corresponding Br,F-diatereomers (2.8 g, 5.15 mmol, 45.9% yield). $^1$H NMR (400 MHz, Chloroform-d) δ ppm 1.06-1.14 (m, 84H), 3.58 (dd, J=12.1, 1.8 Hz, 1H), 3.82-3.86 (m, 2H), 3.88-3.99 (m, 4H), 4.08 (dt, J=5.7, 2.3 Hz, 1H), 4.22 (dtd, J=5.9, 4.1, 1.8 Hz, 1H), 4.75 (dd, J=6.0, 3.5 Hz, 1H), 4.87 (dd, J=16.1, 5.7 Hz, 1H), 5.15 (dd, J=9.7, 5.5 Hz, 1H), 5.39 (dd, J=12.0, 2.1 Hz, 1H)

Example 3C. (3S,4R,5R)-3-bromo-3-fluoro-4-((tri-isopropylsilyl)oxy)-5-(((triisopropylsilyl)oxy)methyl)tetrahydrofuran-2-yl benzoate

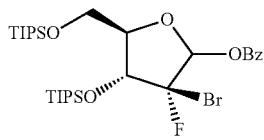

The titled compound was prepared using the conditions described in Example 2E. Using the product of Example 3B (3.66566 g, 6.74 mmol), the title compound was obtained as a colorless oil (4.0742 g, 6.29 mmol, 93% yield). $^1$H NMR (501 MHz, Chloroform-d) δ ppm 1.06-1.31 (m, 67H), 3.86 (dd, J=11.8, 2.4 Hz, 0.6H), 3.95-4.07 (m, 4H), 4.32 (qd, J=4.3, 1.0.6 Hz, 1.2H), 4.87 (dd, J=4.2, 2.0 Hz, 1.2H), 4.96 (dd, J=19.6, 7.4 Hz, 0.6H), 6.42 (d, J=9.5 Hz, 0.6H), 6.73 (s, 1H), 7.41-7.47 (m, 4H), 7.56-7.61 (m, 2H), 8.02-8.05 (m, 1.2H), 8.08-8.11 (m, 2H)

Example 3D. (Z)—N-(1-((2R,3S,4R,5R)-3-bromo-3-fluoro-4-((triisopropylsilyl)oxy)-5-(((triisopropylsilyl)oxy)methyl)tetrahydrofuran-2-yl)-2-oxo-1,2-dihydropyrimidin-4-yl)benzimidic acid

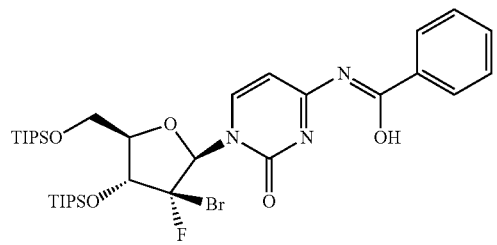

The titled compound was prepared using the conditions described in Example 2F. Using the product of Example 3C (4.0742 g, 6.29 mmol), stirring at 106° C. overnight, the material containing the title compound was purified by flash chromatography using a RediSep® Rf 220 g silica cartridge eluted with a gradient of 0-25% ethyl acetate/heptane. The resulting material was re-purified by flash chromatography using a RediSep® Rf gold 12 g silica cartridge eluted with a gradient of 0-25% ethyl acetate/dichloromethane and gave the title compound (230.38 mg, 0.311 mmol, 4.94% yield) as an off-white solid. $^1$H NMR (500 MHz, DMSO-d$_6$) δ ppm 0.99-1.26 (m, 42H), 3.98 (dd, J=12.2, 2.9 Hz, 1H), 4.05 (d, J=8.5 Hz, 1H), 4.17 (dd, J=12.1, 2.4 Hz, 1H), 4.70 (dd, J=15.5, 8.2 Hz, 1H), 6.45 (d, J=16.0 Hz, 1H), 7.41 (s, 1H), 7.52 (t, J=7.7 Hz, 4H), 7.60-7.66 (m, 2H), 7.88-7.93 (m, 2H), 7.97-8.07 (m, 3H), 11.40 (s, 2H); MS (APCI+) m/z 741.36 (M+H)$^+$.

Example 3E. 1-((2R,3S,4R,5R)-3-bromo-3-fluoro-4-hydroxy-5-(hydroxymethyl)tetrahydrofuran-2-yl)pyrimidine-2,4(1H,3H)-dione

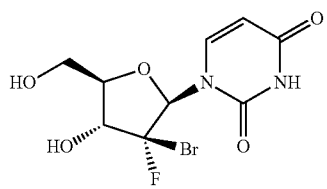 [SMILES: O=c1ccn([C@@H]2O[C@H](CO)[C@@H](O)[C@]2(F)Br)c(=O)[nH]1]

The titled compound was prepared using the conditions described in Example 2G. Using the product of Example 3D (230.38 mg, 0.311 mmol), the material containing the title compound was purified by flash chromatography using a RediSep® Rf gold 12 g silica cartridge eluted with a gradient of 0-10% methanol (MeOH)/dichloromethane. The resulting material was re-purified by flash chromatography using a RediSep® Rf gold 12 g silica cartridge eluted with a gradient of 0-40% of acetonitrile (containing 10% MeOH) in dichloromethane and gave the title compound (59 mg, 0.172 mmol, 55.4% yield). $^1$H NMR (501 MHz, DMSO-d$_6$) δ ppm 3.64 (ddd, J=12.6, 5.2, 3.0 Hz, 1H), 3.79-3.87 (m, 2H), 4.24-4.33 (m, 1H), 5.35 (t, J=5.1 Hz, 1H), 5.73-5.76 (m, 1H), 6.24 (d, J=16.9 Hz, 1H), 6.50 (d, J=7.1 Hz, 1H), 7.84 (d, J=8.1 Hz, 1H), 11.57 (s, 1H); MS (DCI+) m/z 342.1 (M+NH$_4$)$^+$.

Example 3F. (S)-isopropyl 2-(((S)-(((2R,3R,4S,5R)-4-bromo-5-(2,4-dioxo-3,4-dihydropyrimidin-1(2H)-yl)-4-fluoro-3-hydroxytetrahydrofuran-2-yl)methoxy)(phenoxy)phosphoryl)amino)propanoate

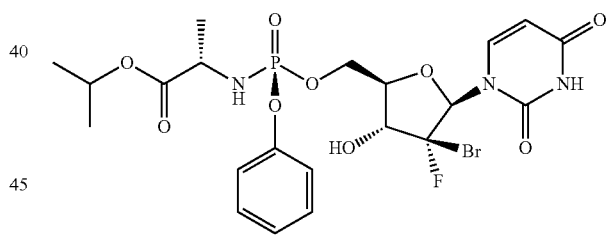

The product of Example 3E (26 mg, 0.080 mmol) was reacted with the corresponding phosphoramidate prodrug moiety compound. The resulting product was concentrated and then purified by flash chromatography using a RediSep® Rf gold 12 g silica cartridge eluted with a gradient of 0-100% ethyl acetate/dichloromethane. The resulting material was re-purified by preparative thin layer chromatography eluted in 50% acetone/heptane and gave the title compound (31 mg, 0.050 mmol, 62.6% yield) as a light yellow solid. $^1$H NMR (400 MHz, DMSO-d$_6$) δ ppm 1.14 (d, J=2.2 Hz, 6H), 1.23 (dd, J=7.2, 1.0 Hz, 3H), 3.74-3.86 (m, 1H), 4.00-4.05 (m, 1H), 4.22-4.40 (m, 2H), 4.86 (hept, J=6.3 Hz, 1H), 5.63 (d, J=8.2 Hz, 1H), 6.06 (dd, J=13.0, 10.0 Hz, 1H), 6.23 (d, J=17.7 Hz, 1H), 6.65 (d, J=7.1 Hz, 1H), 7.16-7.24 (m, 3H), 7.35-7.40 (m, 2H), 7.56 (d, J=8.1 Hz, 1H), 11.58 (s, 1H); MS (ESI+) m/z 593.9 (M+H)$^+$.

The compound of Example 3 had at least about 50-fold lower EC$_{50}$ (i.e., was at least 50-fold more active) than the compound of Example 2 in genotype 1a replicon assays, and had at least about 25-fold lower $EC_{50}$ (i.e., at least 25-fold more active) than the compound of Example 2 in genotype 1b replicon assays. The compound of Example 3 also showed much less cytotoxicity in Huh-7 MTT assays. The compound of Example 3 was also shown to be more active (i.e., lower $EC_{50}$ values) than sofosbuvir in both genotype 1a and 1b replicon assays. In human hepatocyte wash-out experiments (cells incubated for 4 hours with 100 µM of a compound of interest and then the active triphosphate was measured at 24 hours), the compound of Example 3 had a similar intracellular triphosphate concentration as sofosbuvir. In the dog pharmacokinetic liver biopsy experiments (a single dose of 5 mg/kg of a compound of interest was administered to dogs, and the biopsy and measurement of the concentration of the triphosphate active in the dog liver were done at both 4 and 24 hours), the compound of Example 3 showed an intracellular triphosphate concentration similar to or better than sofosbuvir.

Example 4. (S)-isopropyl 2-(((S)-(((2R,3R,5R)-4,4-dibromo-5-(2,4-dioxo-3,4-dihydropyrimidin-1(2H)-yl)-3-hydroxytetrahydrofuran-2-yl)methoxy)(phenoxy)phosphoryl)amino)propanoate

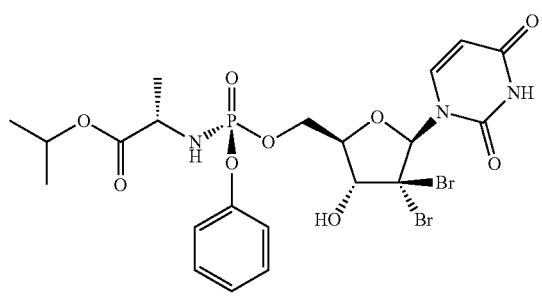

Example 4A. (4S,5R)-4-hydroxy-5-(hydroxymethyl)dihydrofuran-2(3H)-one

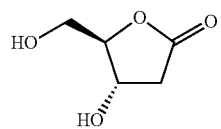

A 500 mL round-bottomed flask was charged with 2-deoxy-D-ribose (10 g, 74.6 mmol) and water (60 mL), followed by the dropwise addition of bromine (59.6 g, 373 mmol). The contents were then stirred at room temperature for 5 days. The reaction mixture was then diluted with water (300 mL) and then extracted with tert-butyl methyl ether (3×200 mL). The aqueous layer was then neutralized with the addition of silver carbonate until the pH of the aqueous solution reached 6. The resulting solids were removed by filtration and the filtrate was concentrated under vacuum to provide a residue which was dissolved in ethyl acetate (200 mL), followed by the addition of magnesium sulfate. After sitting overnight, the solids were filtered off and the filtrate was concentrated to provide the title compound as an oil (7.72 g, 78%). $^1$H NMR (400 MHz, $CDCl_3$) δ 1.83 (t, J=5.9 Hz, 1H), 2.13 (d, J=4.3 Hz, 1H), 2.57 (dd, J=18.1, 4.0 Hz, 1H), 3.00 (dd, J=18.0, 7.2 Hz, 1H), 3.85 (m, 1H), 3.97 (m, 1H), 4.46 (q, J=3.2 Hz, 1H), 4.65 (m, 1H).

Example 4B. (4S,5R)-4-((triisopropylsilyl)oxy)-5-(((triisopropylsilyl)oxy)methyl)dihydrofuran-2(3H)-one

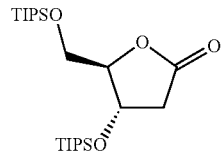

A 250 mL round-bottomed flask was charged with the product of Example 4A (7.5 g, 56.8 mmol) and N,N-dimethylformamide (50 mL), followed by the addition of triisopropylsilyl chloride (30.1 mL, 142 mmol) and 4-(dimethylamino)pyridine (0.35 g, 2.84 mmol). The contents were then stirred at room temperature for 16 hrs. To the reaction mixture was then added a solution of aqueous hydrochloric acid (0.5 N, 300 mL) followed by extraction with ethyl acetate (3×200 mL). The combined organic extracts were dried over magnesium sulfate, and filtered. The filtrate was then concentrated and the residue purified by column chromatography using a 220 g silica gel column, eluting with 0-25% ethyl acetate in heptanes to provide 21.8 g (86%) of the title compound. $^1$H NMR (400 MHz, $CDCl_3$) δ 1.04 (m, 42H), 2.47 (dd, J=17.6, 2.0 Hz, 1H), 2.92 (dd, J=17.6, 6.6 Hz, 1H), 3.91 (dd, J=11.4, 2.4 Hz, 1H), 3.96 (dd, J=11.3, 3.0 Hz, 1H), 4.44 (m, 1H), 4.69 (m, 1H).

Example 4C. (4R,5R)-3-bromo-4-((triisopropylsilyl)oxy)-5-(((triisopropylsilyl)oxy)methyl) dihydrofuran-2(3H)-one

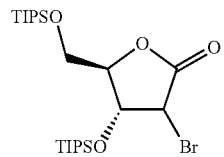

(4R,5S)-4-((triisopropylsilyl)oxy)-5-(((triisopropylsilyl)oxy)methyl)dihydrofuran-2(3H)-one (Example 4B) (5.0 g, 11.24 mmol) was azeotroped with toluene (2×20 mL) and concentrated to dryness. This material was then dissolved in dichloromethane (50 mL) followed by addition of triethylamine (9.40 mL, 67.4 mmol) and cooled to 0° C. Trimethylsilyltrifluoromethanesulfonate (6.09 ml, 33.7 mmol) was added dropwise and allowed to stir for 30 min at 0° C. N-Bromosuccinimide (NBS) (0.878 g, 3.98 mmol) was then dissolved in 50 mL of dichloromethane and added via syringe dropwise over 5 min and then the resultant mixture was stirred at 0° C. for an additional 90 minutes. A saturated aqueous sodium bicarbonate solution was then added and the mixture extracted with dichloromethane, the combined organic extracts dried over magnesium sulfate, and filtered. The filtrate was then concentrated and the residue purified by column chromatography using a 220 g silica gel column, eluting with 0-10% ethyl acetate in heptanes to provide 1.98 g (34%) of the title compound. MS (ESI (+) m/e 540 $(M+NH_4)$.

Example 4D. (4R,5R)-3,3-dibromo-4-((triisopropylsilyl)oxy)-5-(((triisopropylsilyl)oxy)methyl) dihydrofuran-2(3H)-one

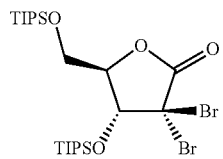

Dry (4R,5R)-3-bromo-4-((triisopropylsilyl)oxy)-5-(((triisopropylsilyl)oxy)methyl) dihydrofuran-2(3H)-one (1.85 g, 3.53 mmol) (Example 4C) was dissolved in dry tetrahydrofuran (20 ml) followed by addition of 1,2-dibromotetrachloroethane (1.73 g, 5.30 mmol) and cooled to −78° C. Lithium bis(trimethylsilyl) amide (5.30 mL, 5.30 mmol, 1M) was then added dropwise via syringe over 5 min yielding a colorless homogenous solution. The mixture was kept at −78° C. for 60 minutes. Then quenched with 0.25 ml of acetic acid followed by addition of half saturated aqueous saturated ammonium chloride and allowed to warm to room temp and extracted with ethyl acetate three times, washed with brine, back extracted aqueous layer with ethyl acetate and pooled organics, and dried over magnesium sulfate, filtered and concentrated. Then columned the residue with 0-5% ethyl acetate in heptanes. The desired product was collected and concentrated to provide the desired product as a colorless oil (1.45 g, 68%). $^1$H NMR (400 MHz, CDCl$_3$) δ 5.03 (d, J=7.2 Hz, 1H), 4.22-4.18 (m, 2H), 3.98 (dd, J=13.3, 1.7 Hz, 1H), 1.32-1.08 (m, 42H). MS (ESI (+) m/e 620 (M+NH$_4$).

Example 4E. (4R,5R)-3,3-dibromo-4-((triisopropylsilyl)oxy)-5-(((triisopropylsilyl)oxy)methyl) tetrahydrofuran-2-ol

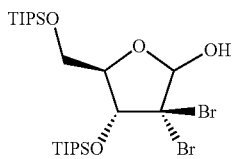

Dry (4R,5R)-3,3-dibromo-4-((triisopropylsilyl)oxy)-5-(((triisopropylsilyl)oxy)methyl) dihydrofuran-2(3H)-one (1.4 g, 2.32 mmol) (Example 4D) was dissolved in toluene (10 ml) under N$_2$ and cooled to −78° C. Diisopropylaluminumhydride in toluene (2.56 ml, 2.56 mmol, 1M) was added via syringe slowly over 2 minutes time and the mixture was stirred for 30 minutes and was done after this time by thin layer chromatography. Then the reaction quenched at this temperature with saturated Rochelle's Salt (15 mL of a 1.0 M aqueous solution) and then allowed to warm slowly to ambient temperature and added heptane to give biphasic turbid mixture which was stirred overnight. After stirring overnight the reaction was filtered through celite and rinsed with ethyl acetate. Aqueous phase was extracted two times with ethyl acetate, and combined organics where dried over magnesium sulfate, filtered and concentrated then columned the residue with 0-10% ethyl acetate in heptanes to provide the desired product (790 mg, 56%) as a colorless oil of lactol anomers. NMR shows anomer mixture as expected but was not purified further.

Example 4F. (4R,5R)-3,3-dibromo-4-((triisopropylsilyl)oxy)-5-(((triisopropylsilyl)oxy)methyl) tetrahydrofuran-2-yl benzoate

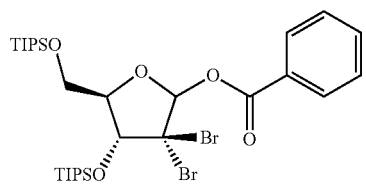

Dry (4R,5R)-3,3-dibromo-4-((triisopropylsilyl)oxy)-5-(((triisopropylsilyl)oxy)methyl) tetrahydrofuran-2-ol (0.780 g, 1.29 mmol) (Example 4E) was dissolved in pyridine (5 mL) and cooled to 0° C. followed by the addition of benzoyl chloride (0.225 mL, 1.94 mmol) dropwise via syringe. After stirring this mixture for 2 hours at room temperature the reaction was diluted with ethyl acetate and washed with half saturated aqueous ammonium chloride. The organic extract was then dried over magnesium sulfate, filtered and concentrated then columned the residue with 0-10% ethyl acetate in heptanes to provide the desired product (840 mg, 92%) as a colorless oil of benzoate anomers. NMR shows anomer mixture as expected but was not purified further. MS (ESI (+) m/e 726 (M+NH$_4$).

Example 4G. N-(1-((2R,4R,5R)-3,3-dibromo-4-((triisopropylsilyl)oxy)-5-(((triisopropylsilyl)oxy)methyl)tetrahydrofuran-2-yl)-2-oxo-1,2-dihydropyrimidin-4-yl)benzamide

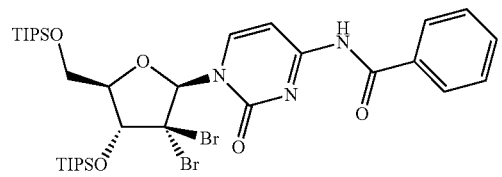

N-(2-oxo-1,2-dihydropyrimidin-4-yl)benzamide (243 mg, 1.13 mmol) was suspended in chlorobenzene (3 mL) in a dry round bottom flask under nitrogen atmosphere followed by addition of N,O-bis(trimethylsilyl)acetamide (0.35 mL, 1.41 mmol) and heated at 80° C. for 45 minutes yielding a homogeneous solution. The mixture was then cooled after heating to ambient temperature. Dry N-(1-((2R,4R,5R)-3,3-dibromo-4-((triisopropylsilyl)oxy)-5-(((triisopropylsilyl)oxy)methyl)tetrahydrofuran-2-yl)-2-oxo-1,2-dihydropyrimidin-4-yl)benzamide (400 mg, 0.564 mmol), (Example 4F) was dissolved in chlorobenzene (3 mL) and added to the mixture followed by the addition of tin (IV) chloride (0.199 mL, 1.69 mmol) added dropwise. After addition the reaction was heated at 80° C. for 2 hours. Then added saturated sodium bicarbonate (10 ml) to give a turbid mixture. Diluted with ethyl acetate and stirred mixture for 30 minutes followed by filtration through a celite plug washing well with ethyl acetate. Filtrate transferred to a separatory funnel and washed again with saturated sodium bicarbonate solution, brine and organics dried over magnesium sulfate, filtered and concentrated. The residue was then columned eluting with 0-50% ethyl acetate in heptanes. Observed chromatographic peak ratio of about 1:2 for alpha, beta anomers respectively which were separated to give the beta anomer as a colorless solid, (0.22 g, 49%). ¹H NMR (400 MHz, DMSO-d$_6$) δ 11.42 (m, 1H), 8.20 (d, J=7.6 Hz, 1H), 7.96 (d, 2H), 7.59 (m, 1H), 7.48 (m, 2H), 7.36 (m, 1H), 6.83 (s, 1H), 4.45 (d, 1H), 4.19 (m, 1H), 3.95 (m, 2H), 1.25-0.98 (m, 42H). MS (ESI (+) m/e 802 (M+H).

Example 4H. 1-((2R,4R,5R)-3,3-dibromo-4-hydroxy-5-(hydroxymethyl)tetrahydrofuran-2-yl)pyrimidine-2,4(1H,3H)-dione

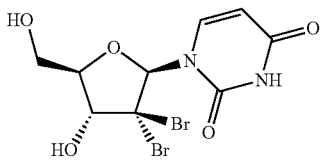

A 25 mL round-bottomed flask was charged with the product of Example 4G (210 mg, 0.262 mmol) and acetic acid (3.0 mL, 52.4 mmol), followed by water (0.944 mL, 52.4 mmol) were added and then the flask was heated at 110° C. for 23 hrs. After cooling to room temperature, the solution was concentrated to an oil and then triturated with toluene two times and then the residue used directly in the next reaction. The material was then dissolved in methanol (3 mL) and then ammonium fluoride (97 mg, 2.62 mmol) added and the mixture heated at 60° C. for 21 hrs. After cooling to room temperature, the reaction mixture was then was then concentrated and the residue purified by column chromatography using a silica gel column, eluting with 0-10% methanol in dichloromethane to provide 45 mg (46%) of the title compound as a colorless solid. ¹H NMR (400 MHz, DMSO-d6) δ 11.47 (s, 1H), 8.04 (d, J=8.6 Hz, 1H), 6.78 (s, 1H), 6.60 (s, 1H), 5.68 (d, J=8.1 Hz, 1H), 5.45 (m, 1H), 4.15 (d, J=8.6 Hz, 1H), 3.78 (m, 2H), 3.61 (m, 1H). MS ESI– m/z 385 (M–H)+.

Example 4I. (S)-isopropyl 2-(((S)-(((2R,3R,5R)-4,4-dibromo-5-(2,4-dioxo-3,4-dihydropyrimidin-1(2H)-yl)-3-hydroxytetrahydrofuran-2-yl)methoxy)(phenoxy)phosphoryl)amino)propanoate

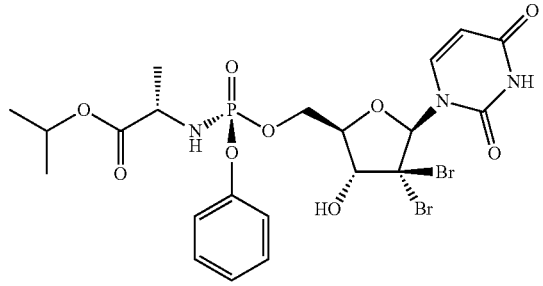

The product of Example 4H (42 mg, 0.109 mmol) was reacted with the corresponding phosphoramidate prodrug moiety compound. The resulting product was extracted with ethyl acetate (2×10 mL). The combined organic extracts were dried over magnesium sulfate, and filtered. The filtrate was then concentrated and the residue purified by column chromatography using a silica gel column, eluting with 0-100% ethyl acetate in heptanes to provide 46 mg (65%) of the title compound. ¹H NMR (400 MHz, DMSO-d6) δ 11.58 (s, 1H), 7.62 (d, J=5.9 Hz, 1H), 7.36 (m, 2H), 7.19 (m, 3H), 6.95 (m, 1H), 6.63 (s, 1H), 6.07 (m, 1H), 5.56 (d, J=8.2 Hz, 1H), 4.83 (m, 1H), 4.15 (m, 3H), 4.01 (m, 1H), 3.81 (m, 1H), 1.21 (d, J=7.1 Hz, 3H), 1.14 (d, J=6.2 Hz, 6H). MS ESI– m/z 654 (M–H)+.

Example 5. Ethyl 2-(((((2R,3R,4R,5R)-4-bromo-4-chloro-5-(2,4-dioxo-3,4-dihydropyrimidin-1(2H)-yl)-3-hydroxytetrahydrofuran-2-yl)methoxy)(phenoxy)phosphoryl)amino)-2-methylpropanoate

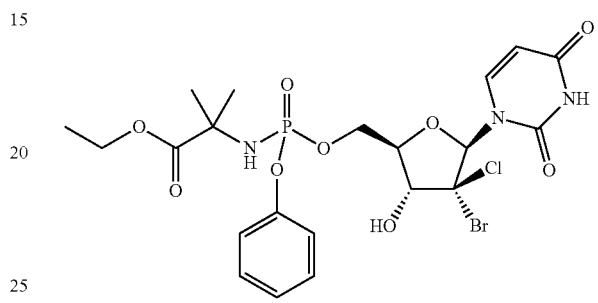

A solution of the product from Example 1H (744 mg, 2.178 mmol) in anhydrous THF (10 ml), and DMPU (1 ml) was cooled to 0° C. A 1.0 M solution of tert-butylmagnesium chloride in THF (2.396 ml, 2.396 mmol) was added dropwise, and the resulting mixture was stirred for 30 min before the corresponding phosphoramidate prodrug moiety compound was added in one portion. The reaction mixture was allowed to warm to room temperature and stirred for 12 hrs. The reaction was quenched with a saturated solution of NH$_4$Cl, and the mixture was extracted with dichloromethane (2×). The combined organic layers were dried over sodium sulfate, filtered and concentrated in vacuo, and the product was isolated by C18 HPLC using a solvent gradient of 5-95% acetonitrile in water (0.1% TFA). The title compound was obtained as a colorless solid (0.82 g, 62%). ¹H NMR (400 MHz, DMSO-d$_6$) δ 11.57 (d, J=2.3 Hz, 1H), 7.70-7.54 (m, 1H), 7.40-7.32 (m, 2H), 7.23-7.12 (m, 3H), 7.01 (s, 1H), 6.63 (s, 1H), 6.03-5.91 (m, 1H), 5.57-5.48 (m, 1H), 4.42-4.25 (m, 2H), 4.13-3.97 (m, 4H), 1.40-1.30 (m, 6H), 1.15-1.09 (m, 3H).

Example 6. Ethyl 2-(((R)-(((2R,3R,4R,5R)-4-bromo-4-chloro-5-(2,4-dioxo-3,4-dihydropyrimidin-1(2H)-yl)-3-hydroxytetrahydrofuran-2-yl)methoxy)(phenoxy)phosphoryl)amino)-2-methylpropanoate

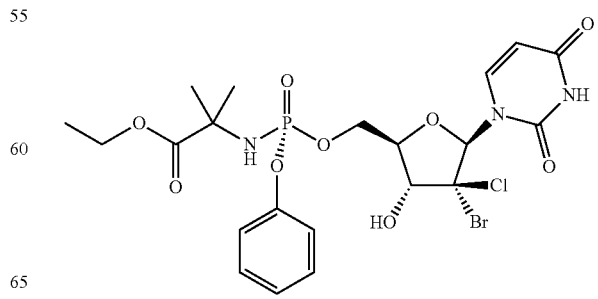

The product from Example 1C was purified by chiral SFC chromatography using a Chiralpak AD-H column, eluting with isocratic mobile phase that consisted of supercritical $CO_2$ and 40% methanol. The title compound was the first of two stereoisomers to elute. $^1$H NMR (400 MHz, DMSO-$d_6$) δ 11.56 (d, J=2.2 Hz, 1H), 7.58 (d, J=8.2 Hz, 1H), 7.38-7.30 (m, 2H), 7.22-7.17 (m, 2H), 7.13 (t, J=7.5 Hz, 1H), 7.03 (s, 1H), 6.61 (s, 1H), 5.99 (d, J=9.7 Hz, 1H), 5.49 (dd, J=8.2, 2.2 Hz, 1H), 4.41-4.23 (m, 2H), 4.07-3.95 (m, 4H), 1.37-1.34 (m, 3H), 1.30 (s, 3H), 1.11 (t, J=7.1 Hz, 3H).

The compound of Example 6 showed an EC50 value of about 2-3 M in genotype 1a replicon assay, and an $EC_{50}$ value of about 2-3 μM in genotype 1b replicon assay. In human hepatocyte wash-out experiments (cells incubated for 4 hours with 100 μM of a compound of interest and then the active triphosphate was measured at 24 hours), the compound of Example 6 showed a significantly higher intracellular triphosphate concentration than the compound of Example 1. In the dog pharmacokinetic liver biopsy experiments (a single dose of 5 mg/kg of a compound of interest was administered to dogs, and the biopsy and measurement of the concentration of the triphosphate active in the dog liver were done at both 4 and 24 hours), the compound of Example 6 also showed a significantly higher intracellular triphosphate concentration than the compound of Example 1.

Example 7. Ethyl 2-(((S)-(((2R,3R,4R,5R)-4-bromo-4-chloro-5-(2,4-dioxo-3,4-dihydropyrimidin-1(2H)-yl)-3-hydroxytetrahydrofuran-2-yl)methoxy)(phenoxy)phosphoryl)amino)-2-methylpropanoate

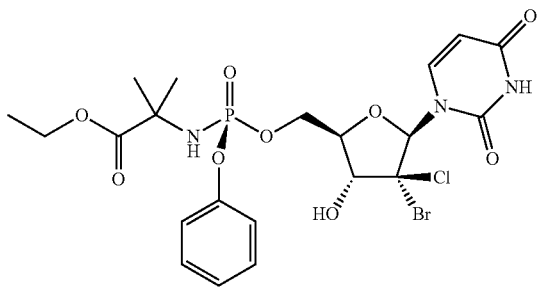 [SMILES: CCOC(=O)C(C)(C)N[P@](=O)(OC[C@H]1O[C@@H](n2ccc(=O)[nH]c2=O)[C@](Cl)(Br)[C@@H]1O)Oc1ccccc1]

The product from Example 1C was purified by chiral SFC chromatography using a Chiralpak AD-H column, eluting with isocratic mobile phase that consisted of supercritical $CO_2$ and 40% methanol. The title compound was the second of two stereoisomers to elute. $^1$H NMR (501 MHz, DMSO-$d_6$) δ 11.58 (d, J=2.2 Hz, 1H), 7.66 (d, J=8.2 Hz, 1H), 7.36 (dd, J=8.6, 7.3 Hz, 2H), 7.24-7.14 (m, 3H), 7.01 (s, 1H), 6.62 (s, 1H), 5.96 (d, J=9.6 Hz, 1H), 5.52 (dd, J=8.2, 2.2 Hz, 1H), 4.40-4.25 (m, 2H), 4.14-3.97 (m, 4H), 1.37 (s, 3H), 1.33 (s, 3H), 1.12 (t, J=7.1 Hz, 3H).

The compound of Example 7 showed an EC50 value of about 0.6 μM in genotype 1a replicon assay, and an $EC_{50}$ value of about 1 μM in genotype 1b replicon assay. In human hepatocyte wash-out experiments (cells incubated for 4 hours with 100 μM of a compound of interest and then the active triphosphate was measured at 24 hours), the compound of Example 7 showed a significantly higher intracellular triphosphate concentration than the compound of Example 1. In the dog pharmacokinetic liver biopsy experiments (a single dose of 5 mg/kg of a compound of interest was administered to dogs, and the biopsy and measurement of the concentration of the triphosphate active in the dog liver were done at both 4 and 24 hours), the compound of Example 7 also showed a significantly higher intracellular triphosphate concentration than the compound of Example 1.

Example 8. Ethyl ((((2R,3R,4R,5R)-4-bromo-4-chloro-5-(2,4-dioxo-3,4-dihydropyrimidin-1(2H)-yl)-3-hydroxytetrahydrofuran-2-yl)methoxy)(phenoxy)phosphoryl)-L-alaninate

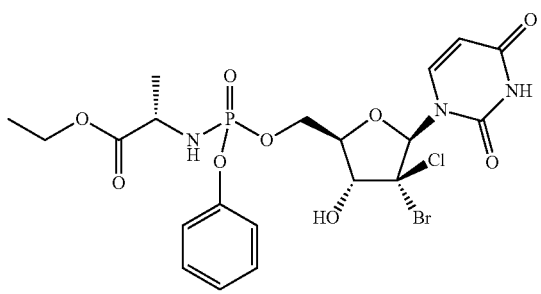 [SMILES: CCOC(=O)[C@H](C)NP(=O)(OC[C@H]1O[C@@H](n2ccc(=O)[nH]c2=O)[C@](Cl)(Br)[C@@H]1O)Oc1ccccc1]

The title compound was prepared using a method similar to that described for Example 5. $^1$H NMR (400 MHz, DMSO-$d_6$) δ 11.56 (s, 1H), 7.62 (d, J=8.2 Hz, 1H), 7.35 (ddd, J=9.3, 7.2, 2.1 Hz, 2H), 7.22-7.11 (m, 3H), 7.08-6.93 (m, 1H), 6.64-6.58 (m, 1H), 6.17-6.03 (m, 1H), 5.58-5.51 (m, 1H), 4.41-4.21 (m, 2H), 4.02 (qd, J=7.1, 2.1 Hz, 4H), 3.88-3.73 (m, 1H), 1.23-1.09 (m, 6H).

Example 9. Ethyl ((S)-(((2R,3R,4R,5R)-4-bromo-4-chloro-5-(2,4-dioxo-3,4-dihydropyrimidin-1(2H)-yl)-3-hydroxytetrahydrofuran-2-yl)methoxy) (phenoxy)phosphoryl)-L-alaninate

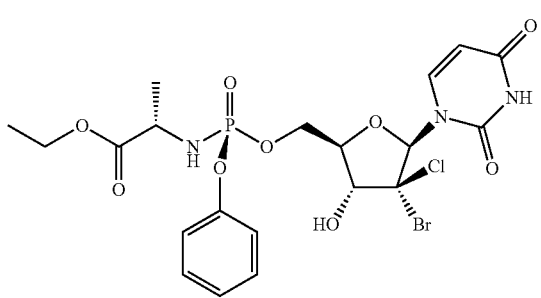 [SMILES: CCOC(=O)[C@H](C)N[P@](=O)(OC[C@H]1O[C@@H](n2ccc(=O)[nH]c2=O)[C@](Cl)(Br)[C@@H]1O)Oc1ccccc1]

The product from Example 8 was purified by chiral SFC chromatography using a Chiralpak AD-H column, eluting with 35% methanol in supercritical $CO_2$ to provide the title compound. $^1$H NMR (400 MHz, DMSO-$d_6$) δ 11.55 (s, 1H), 7.62 (d, J=8.2 Hz, 1H), 7.40-7.31 (m, 2H), 7.21-7.11 (m, 3H), 7.04 (s, 1H), 6.63 (s, 1H), 6.12 (dd, J=12.8, 9.9 Hz, 1H), 5.55 (d, J=8.1 Hz, 1H), 4.38 (dd, J=12.0, 5.6 Hz, 1H), 4.33-4.23 (m, 1H), 4.08-3.95 (m, 4H), 3.85-3.71 (m, 1H), 1.18 (dd, J=7.1, 1.2 Hz, 3H), 1.11 (t, J=7.1 Hz, 3H).

Example 10. Ethyl ((R)-(((2R,3R,4R,5R)-4-bromo-4-chloro-5-(2,4-dioxo-3,4-dihydropyrimidin-1(2H)-yl)-3-hydroxytetrahydrofuran-2-yl)methoxy)(phenoxy)phosphoryl)-L-alaninate

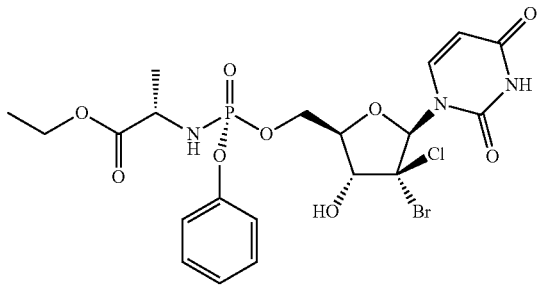 [SMILES: CCOC(=O)[C@H](C)N[P@@](=O)(OC[C@H]1O[C@@H](n2ccc(=O)[nH]c2=O)[C@](Cl)(Br)[C@@H]1O)Oc1ccccc1]

The product from Example 8 was purified by chiral SFC chromatography using a Chiralpak AD-H column, eluting with 35% methanol in supercritical CO$_2$ to provide the title compound. $^1$H NMR (501 MHz, DMSO-d$_6$) δ 11.58 (s, 1H), 7.63 (d, J=8.2 Hz, 1H), 7.39-7.34 (m, 2H), 7.23-7.15 (m, 3H), 6.99 (d, J=5.8 Hz, 1H), 6.62 (s, 1H), 6.10 (dd, J=13.0, 10.0 Hz, 1H), 5.56 (d, J=8.3 Hz, 1H), 4.37-4.24 (m, 2H), 4.11-3.97 (m, 4H), 3.89-3.79 (m, 1H), 1.23 (dd, J=7.2, 0.9 Hz, 3H), 1.14 (t, J=7.1 Hz, 3H).

Example 11. Isopropyl 2-(((((2R,3R,4R,5R)-4-bromo-4-chloro-5-(2,4-dioxo-3,4-dihydropyrimidin-1(2H)-yl)-3-hydroxytetrahydrofuran-2-yl)methoxy)(phenoxy)phosphoryl)amino)-2-methylpropanoate

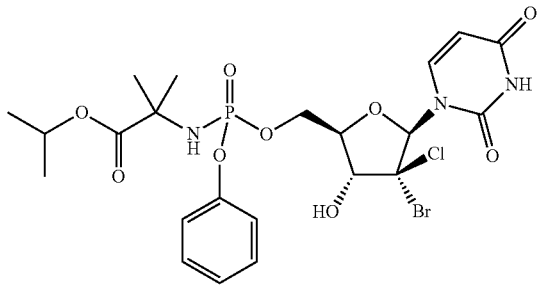 [SMILES: CC(C)OC(=O)C(C)(C)NP(=O)(OC[C@H]1O[C@@H](n2ccc(=O)[nH]c2=O)[C@](Cl)(Br)[C@@H]1O)Oc1ccccc1]

The title compound was prepared using a method similar to that described for Example 5. $^1$H NMR (400 MHz, DMSO-d$_6$) δ 11.60-11.55 (m, 1H), 7.70-7.55 (m, 1H), 7.41-7.31 (m, 2H), 7.25-7.12 (m, 3H), 7.05-6.94 (m, 1H), 6.66-6.59 (m, 1H), 5.98-5.85 (m, 1H), 5.55-5.47 (m, 1H), 4.88-4.77 (m, 1H), 4.41-4.25 (m, 2H), 4.13-3.96 (m, 2H), 1.38-1.30 (m, 6H), 1.16-1.10 (m, 6H).

Example 12. Isopropyl 2-(((S)-(((2R,3R,4R,5R)-4-bromo-4-chloro-5-(2,4-dioxo-3,4-dihydropyrimidin-1(2H)-yl)-3-hydroxytetrahydrofuran-2-yl)methoxy)(phenoxy)phosphoryl)amino)-2-methylpropanoate

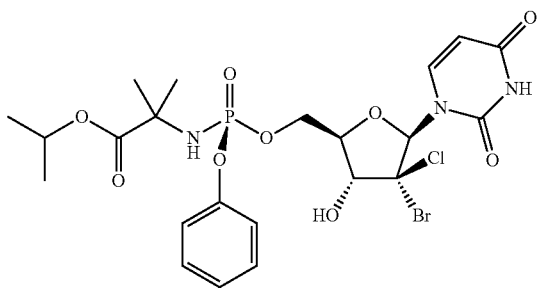 [SMILES: CC(C)OC(=O)C(C)(C)N[P@](=O)(OC[C@H]1O[C@@H](n2ccc(=O)[nH]c2=O)[C@](Cl)(Br)[C@@H]1O)Oc1ccccc1]

The product from Example 11 was purified by chiral SFC chromatography using a Chiralcel OJ-H column, eluting with 30% isopropanol in supercritical CO$_2$ to provide the title compound. $^1$H NMR (501 MHz, DMSO-d$_6$) δ 11.53 (s, 1H), 7.66 (d, J=8.2 Hz, 1H), 7.39-7.33 (m, 2H), 7.24-7.19 (m, 2H), 7.17 (t, J=7.4 Hz, 1H), 6.99 (d, J=5.7 Hz, 1H), 6.62 (s, 1H), 5.89 (d, J=9.6 Hz, 1H), 5.52 (d, J=8.2 Hz, 1H), 4.83 (hept, J=6.4 Hz, 1H), 4.41-4.26 (m, 2H), 4.14-3.97 (m, 2H), 1.36 (s, 3H), 1.32 (s, 3H), 1.13 (t, J=6.4 Hz, 6H).

Example 13. Isopropyl 2-(((R)-(((2R,3R,4R,5R)-4-bromo-4-chloro-5-(2,4-dioxo-3,4-dihydropyrimidin-1(2H)-yl)-3-hydroxytetrahydrofuran-2-yl)methoxy)(phenoxy)phosphoryl)amino)-2-methylpropanoate

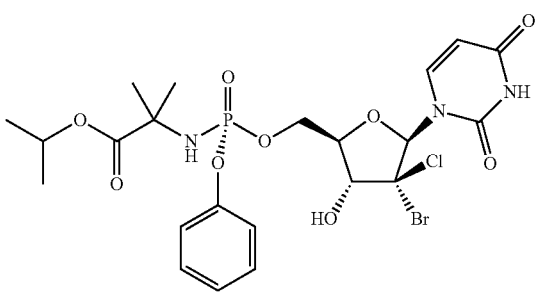 [SMILES: CC(C)OC(=O)C(C)(C)N[P@@](=O)(OC[C@H]1O[C@@H](n2ccc(=O)[nH]c2=O)[C@](Cl)(Br)[C@@H]1O)Oc1ccccc1]

The product from Example 11 was purified by chiral SFC chromatography using a Chiralcel OJ-H column, eluting with 30% isopropanol in supercritical CO$_2$ to provide the title compound. $^1$H NMR (400 MHz, DMSO-d$_6$) δ 11.56 (s, 1H), 7.57 (d, J=8.1 Hz, 1H), 7.34 (dd, J=8.5, 7.3 Hz, 2H), 7.23-7.17 (m, 2H), 7.17-7.09 (m, 1H), 7.03 (s, 1H), 6.62 (s, 1H), 5.93 (d, J=9.6 Hz, 1H), 5.48 (d, J=8.1 Hz, 1H), 4.82 (hept, J=6.3 Hz, 1H), 4.43-4.22 (m, 2H), 4.01 (s, 2H), 1.35-1.32 (m, 3H), 1.30 (s, 3H), 1.12 (t, J=6.0 Hz, 6H).

Example 14. Isopropyl (((((2R,3R,4R,5R)-4-bromo-4-chloro-5-(2,4-dioxo-3,4-dihydropyrimidin-1(2H)-yl)-3-hydroxytetrahydrofuran-2-yl)methoxy)(phenoxy)phosphoryl)-D-alaninate

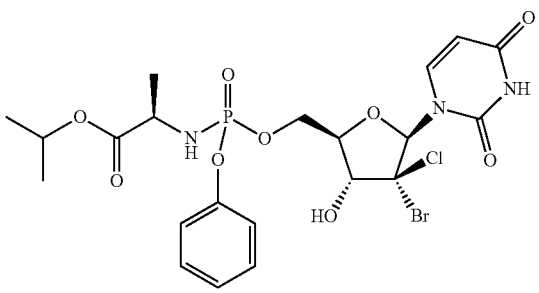 [SMILES: CC(C)OC(=O)[C@@H](C)NP(=O)(OC[C@H]1O[C@@H](n2ccc(=O)[nH]c2=O)[C@](Cl)(Br)[C@@H]1O)Oc1ccccc1]

The title compound was prepared using a method similar to that described for Example 5. $^1$H NMR (400 MHz, DMSO-d$_6$) δ 11.61-11.56 (m, 1H), 7.71-7.54 (m, 1H), 7.36 (dd, J=8.6, 7.1 Hz, 2H), 7.26-7.13 (m, 3H), 7.08-6.95 (m, 1H), 6.63 (s, 1H), 6.19-6.00 (m, 1H), 5.62-5.51 (m, 1H), 4.89-4.77 (m, 1H), 4.42-4.24 (m, 1H), 4.14-3.96 (m, 2H), 3.82-3.70 (m, 1H), 1.22-1.16 (m, 3H), 1.13 (dt, J=5.6, 2.7 Hz, 6H).

Example 15. Isopropyl ((R)-(((2R,3R,4R,5R)-4-bromo-4-chloro-5-(2,4-dioxo-3,4-dihydropyrimidin-1(2H)-yl)-3-hydroxytetrahydrofuran-2-yl)methoxy)(phenoxy)phosphoryl)-D-alaninate

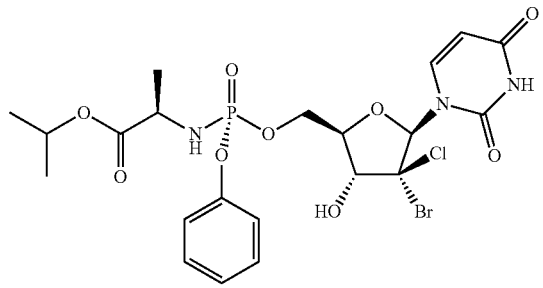 [SMILES: CC(C)OC(=O)[C@@H](C)N[P@@](=O)(OC[C@H]1O[C@@H](n2ccc(=O)[nH]c2=O)[C@](Cl)(Br)[C@@H]1O)Oc1ccccc1]

The product from Example 14 was purified by chiral SFC chromatography using a Chiralpak AD-H column, eluting with 40% methanol in supercritical $CO_2$ to provide the title compound. $^1$H NMR (400 MHz, DMSO-d$_6$) δ 11.59 (d, J=2.3 Hz, 1H), 7.58 (d, J=8.2 Hz, 1H), 7.43-7.33 (m, 2H), 7.26-7.13 (m, 3H), 7.05 (s, 1H), 6.63 (s, 1H), 6.14 (dd, J=13.6, 10.1 Hz, 1H), 5.59 (dd, J=8.1, 2.2 Hz, 1H), 4.84 (hept, J=6.3 Hz, 1H), 4.41-4.23 (m, 2H), 4.00 (s, 2H), 3.82-3.69 (m, 1H), 1.23-1.18 (m, 3H), 1.13 (dd, J=6.3, 4.6 Hz, 6H).

Example 16. Isopropyl ((((2R,3R,4R,5R)-4-bromo-4-chloro-5-(2,4-dioxo-3,4-dihydropyrimidin-1(2H)-yl)-3-hydroxytetrahydrofuran-2-yl)methoxy)(3-methoxyphenoxy)phosphoryl)-L-alaninate

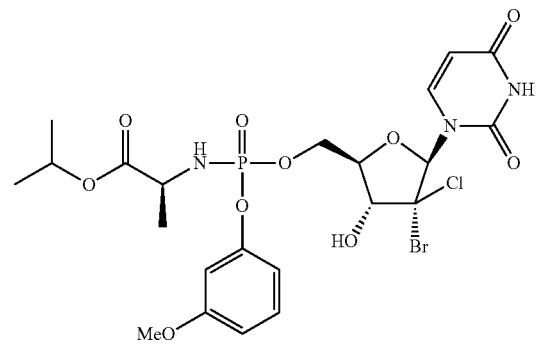 [SMILES: COc1cccc(OP(=O)(N[C@@H](C)C(=O)OC(C)C)OC[C@H]2O[C@@H](n3ccc(=O)[nH]c3=O)[C@](Cl)(Br)[C@@H]2O)c1]

The title compound was prepared using a method similar to that described for Example 5. $^1$H NMR (501 MHz, DMSO-d$_6$) δ 11.60-11.56 (m, 1H), 7.70-7.60 (m, 1H), 7.28-7.21 (m, 1H), 7.10-6.94 (m, 1H), 6.81-6.72 (m, 3H), 6.68-6.60 (m, 1H), 6.16-6.03 (m, 1H), 5.60-5.54 (m, 1H), 4.87-4.79 (m, 1H), 4.42-4.23 (m, 2H), 4.13-3.96 (m, 2H), 3.84-3.66 (m, 4H), 1.24-1.17 (m, 3H), 1.16-1.11 (m, 6H).

Example 17. Isopropyl ((S)-(((2R,3R,4R,5R)-4-bromo-4-chloro-5-(2,4-dioxo-3,4-dihydropyrimidin-1(2H)-yl)-3-hydroxytetrahydrofuran-2-yl)methoxy)(3-methoxyphenoxy)phosphoryl)-L-alaninate

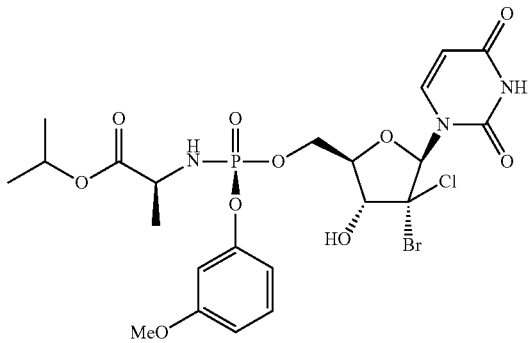 [SMILES: COc1cccc(O[P@](=O)(N[C@@H](C)C(=O)OC(C)C)OC[C@H]2O[C@@H](n3ccc(=O)[nH]c3=O)[C@](Cl)(Br)[C@@H]2O)c1]

The title compound was prepared using a method similar to that described for Example 5. $^1$H NMR (400 MHz, DMSO-d6) δ 11.57 (d, J=2.2 Hz, 1H), 7.62 (d, J=8.2 Hz, 1H), 7.28-7.19 (m, 1H), 6.98 (s, 1H), 6.80-6.70 (m, 3H), 6.61 (s, 1H), 6.07 (dd, J=13.1, 10.0 Hz, 1H), 5.55 (dd, J=8.1, 2.2 Hz, 1H), 4.82 (hept, J=6.3 Hz, 1H), 4.37-4.21 (m, 2H), 4.12-3.93 (m, 2H), 3.85-3.71 (m, 1H), 3.71 (s, 3H), 1.20 (d, J=7.1 Hz, 3H), 1.12 (d, J=6.3 Hz, 6H).

Example 18. Isopropyl ((S)-(((2R,3R,4R,5R)-4-bromo-4-chloro-5-(2,4-dioxo-3,4-dihydropyrimidin-1(2H)-yl)-3-hydroxytetrahydrofuran-2-yl)methoxy)(naphthalen-1-yloxy)phosphoryl)-L-alaninate

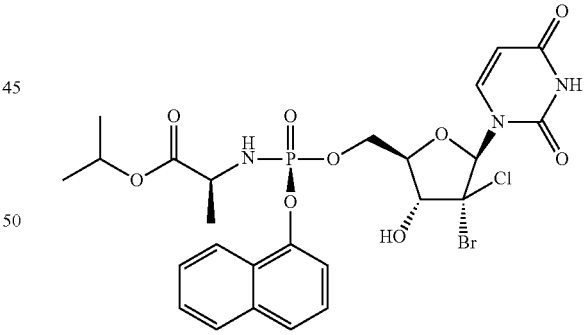

The title compound was prepared using a method similar to that described for Example 5. $^1$H NMR (400 MHz, DMSO-d$_6$) δ 11.56 (d, J=2.2 Hz, 1H), 11.36 (s, 1H), 8.16-8.07 (m, 1H), 7.99-7.90 (m, 1H), 7.74 (dd, J=6.6, 2.6 Hz, 1H), 7.62-7.52 (m, 2H), 7.52-7.41 (m, 2H), 6.99 (d, J=5.6 Hz, 1H), 6.61 (s, 1H), 6.25 (dd, J=12.6, 10.0 Hz, 1H), 5.41 (dd, J=8.2, 2.1 Hz, 1H), 4.90-4.79 (m, 1H), 4.45-4.30 (m, 2H), 4.17-3.97 (m, 2H), 3.94-3.81 (m, 1H), 1.23 (d, J=7.1 Hz, 3H), 1.12 (dd, J=6.2, 1.4 Hz, 6H).

Example 19. (2R,3R,4R,5R)-4-bromo-4-chloro-5-(2,4-dioxo-3,4-dihydropyrimidin-1(2H)-yl)-2-((((S)—(((S)-1-isopropoxy-1-oxopropan-2-yl)amino)(phenoxy)phosphoryl)oxy)methyl)tetrahydrofuran-3-yl L-valinate Example 19B. (2R,3R,4R,5R)-4-bromo-4-chloro-5-(2,4-dioxo-3,4-dihydropyrimidin-1(2H)-yl)-2-((((S)—(((S)-1-isopropoxy-1-oxopropan-2-yl)amino)(phenoxy)phosphoryl)oxy)methyl)tetrahydrofuran-3-yl L-valinate

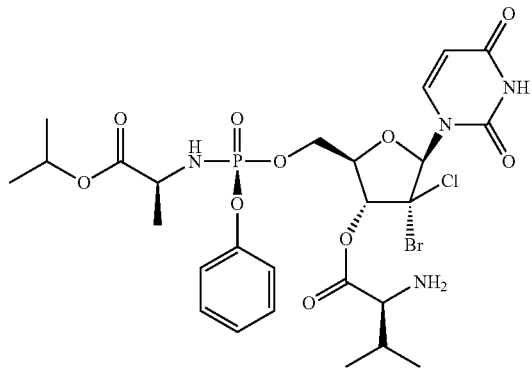

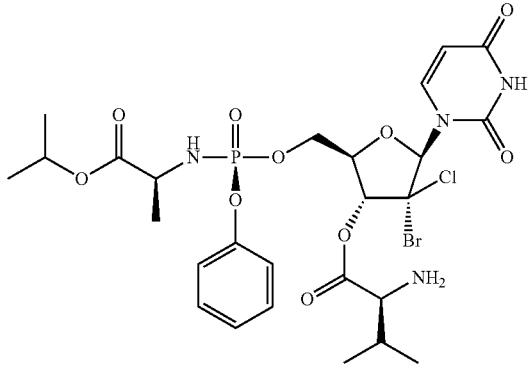 [SMILES: CC(C)OC(=O)[C@H](C)N[P@](=O)(OC[C@H]1O[C@@H](n2ccc(=O)[nH]c2=O)[C@](Cl)(Br)[C@@H]1OC(=O)[C@@H](N)C(C)C)Oc1ccccc1]

Example 19A. (2R,3R,4R,5R)-4-bromo-4-chloro-5-(2,4-dioxo-3,4-dihydropyrimidin-1(2H)-yl)-2-((((S)—(((S)-1-isopropoxy-1-oxopropan-2-yl)amino)(phenoxy)phosphoryl)oxy)methyl)tetrahydrofuran-3-yl (tert-butoxycarbonyl)-L-valinate

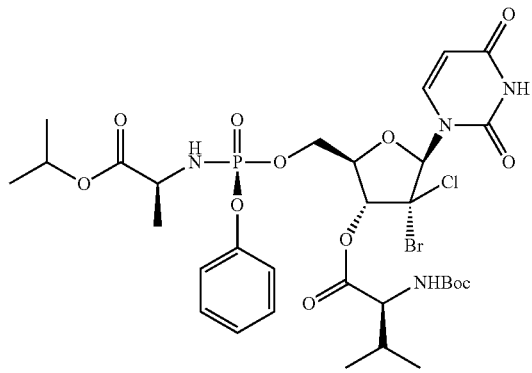 [SMILES: CC(C)OC(=O)[C@H](C)N[P@](=O)(OC[C@H]1O[C@@H](n2ccc(=O)[nH]c2=O)[C@](Cl)(Br)[C@@H]1OC(=O)[C@@H](NC(=O)OC(C)(C)C)C(C)C)Oc1ccccc1]

A mixture of Boc-L-Valine (0.427 g, 1.965 mmol), carbonyldiimidazole (0.319 g, 1.965 mmol) (0.319 g, 1.965 mmol), and triethylamine (0.685 ml, 4.91 mmol) in anhydrous tetrahydrofuran (16 ml) was stirred at 50° C. under N$_2$ for 90 min. The resulting mixture was cooled to room temperature, and the product from Example 1I (1.00 g, 1.637 mmol) and 4-dimethylaminopyridine (0.020 g, 0.164 mmol) were added. The resulting mixture was stirred at 60° C. overnight. The mixture was cooled to rt and partitioned between 1 N aq HCl and EtOAc (3×). The combined organic layers were dried over sodium sulfate. The drying agent was filtered off, and the solvent was removed in vacuo. The crude product was purified by column chromatography on silica gel using a solvent gradient of 0-5% methanol in dichloromethane. The title compound was obtained a colorless solid (0.958 g, 72%).

A solution of the product from Example 19A (0.565 g, 0.698 mmol) in dichloromethane (4 ml) and trifluoroacetic acid (1 ml, 12.98 mmol) was stirred at room temperature for 1 hr and then concentrated in vacuo. The residue was dissolved in ethyl acetate and washed with saturated aq. sodium bicarbonate. The layers were separated and the organic layer was dried over sodium sulfate. The drying agent was filtered off, and the solvent was removed in vacuo. The crude product was purified by column chromatography on silica gel using a solvent gradient of 50-100% ethyl acetate in heptanes. The title compound was obtained as a colorless solid (0.439 g, 89%). 1H NMR (400 MHz, DMSO-d6) δ 7.72 (d, J=8.2 Hz, 1H), 7.34 (dd, J=8.6, 7.2 Hz, 2H), 7.23-7.10 (m, 2H), 6.61 (s, 1H), 6.07 (dd, J=13.0, 10.0 Hz, 1H), 5.69-5.60 (m, 1H), 5.51 (s, 1H), 4.83 (hept, J=6.3 Hz, 1H), 4.27 (dtd, J=15.7, 7.4, 6.9, 4.5 Hz, 3H), 3.76 (tq, J=10.1, 7.1 Hz, 1H), 3.23 (d, J=5.7 Hz, 1H), 1.99-1.84 (m, 1H), 1.23-1.17 (m, 3H), 1.12 (dd, J=6.2, 1.8 Hz, 6H), 0.90 (d, J=6.8 Hz, 3H), 0.84 (d, J=6.8 Hz, 3H).

Example 20. (2R,3R,4R,5R)-4-bromo-4-chloro-5-(2,4-dioxo-3,4-dihydropyrimidin-1(2H)-yl)-2-((((S)—(((S)-1-isopropoxy-1-oxopropan-2-yl)amino)(naphthalen-1-yloxy)phosphoryl)oxy)methyl)tetrahydrofuran-3-yl L-valinate

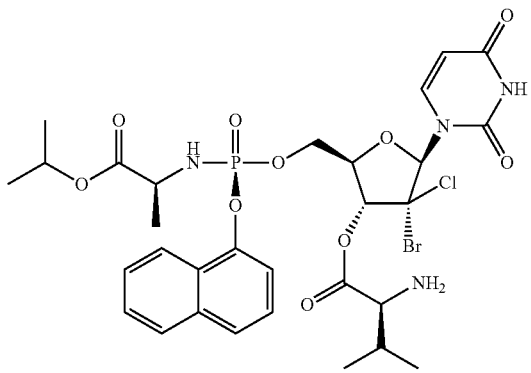 [SMILES: CC(C)OC(=O)[C@H](C)N[P@](=O)(OC[C@H]1O[C@@H](n2ccc(=O)[nH]c2=O)[C@](Cl)(Br)[C@@H]1OC(=O)[C@@H](N)C(C)C)Oc1cccc2ccccc12]

The title compound was prepared using a method similar to that described for Example 19, substituting the product from Example 18 for the product from Example 1I. 1H NMR (400 MHz, DMSO-d6) δ 11.53 (s, 1H), 8.12-8.07 (m, 1H), 7.96-7.89 (m, 1H), 7.73 (dd, J=6.7, 2.6 Hz, 1H), 7.62 (d, J=8.3 Hz, 1H), 7.57-7.52 (m, 2H), 7.48-7.41 (m, 2H), 6.59 (s, 1H), 6.26 (dd, J=12.6, 9.9 Hz, 1H), 5.57-5.49 (m, 2H), 4.83 (hept, J=6.3 Hz, 1H), 4.42-4.24 (m, 3H), 3.85 (tq, J=10.1, 7.1 Hz, 1H), 3.22 (d, J=5.7 Hz, 1H), 1.89 (ddd, J=13.6, 6.9, 5.7 Hz, 1H), 1.22 (d, J=7.1 Hz, 3H), 1.11 (d, J=6.3 Hz, 6H), 0.87 (d, J=6.7 Hz, 3H), 0.82 (d, J=6.7 Hz, 3H).

Example 21. (2R,3R,4R,5R)-4-bromo-4-chloro-5-(2,4-dioxo-3,4-dihydropyrimidin-1(2H)-yl)-2-((((S)—(((S)-1-isopropoxy-1-oxopropan-2-yl)amino)(phenoxy)phosphoryl)oxy)methyl)tetrahydrofuran-3-yl L-alaninate

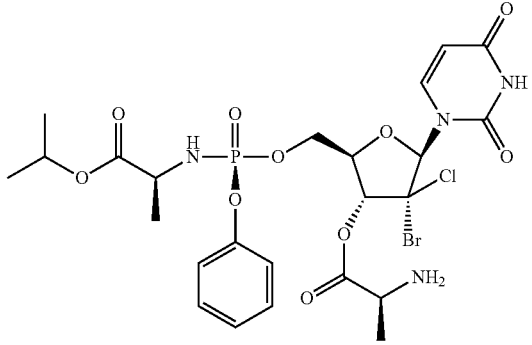 [SMILES: CC(C)OC(=O)[C@H](C)N[P@](=O)(OC[C@H]1O[C@@H](n2ccc(=O)[nH]c2=O)[C@](Cl)(Br)[C@@H]1OC(=O)[C@H](C)N)Oc1ccccc1]

The title compound was prepared using the methods described for Example 19, substituting Boc-L-Alanine for Boc-L-Valine. 1H NMR (400 MHz, DMSO-d6) δ 11.64 (d, J=2.2 Hz, 1H), 8.46 (br s, 2H), 7.73 (d, J=8.2 Hz, 1H), 7.35 (dd, J=8.7, 7.2 Hz, 2H), 7.17 (dd, J=11.4, 7.8 Hz, 3H), 6.62 (s, 1H), 6.09 (dd, J=13.0, 10.1 Hz, 1H), 5.68 (dd, J=8.2, 2.2 Hz, 1H), 5.58 (br s, 1H), 4.83 (p, J=6.3 Hz, 1H), 4.32 (dqt, J=19.8, 7.6, 4.0 Hz, 3H), 3.77 (tq, J=10.2, 7.1 Hz, 1H), 1.46 (d, J=7.2 Hz, 3H), 1.20 (d, J=7.0 Hz, 3H), 1.12 (d, J=6.3 Hz, 6H).

Example 22. Isopropyl ((R)-(((2R,3R,4R,5R)-4-bromo-4-chloro-5-(2,4-dioxo-3,4-dihydropyrimidin-1(2H)-yl)-3-hydroxytetrahydrofuran-2-yl)methoxy)(phenoxy)phosphoryl)-L-alaninate

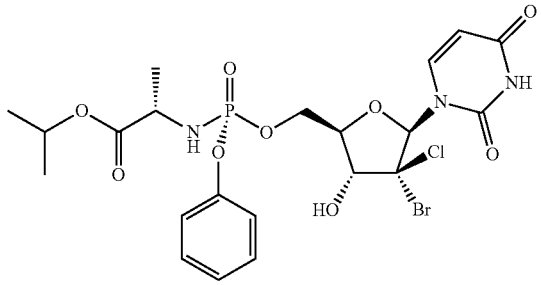 [SMILES: CC(C)OC(=O)[C@H](C)N[P@@](=O)(OC[C@H]1O[C@@H](n2ccc(=O)[nH]c2=O)[C@](Cl)(Br)[C@@H]1O)Oc1ccccc1]

The title compound was prepared using a method similar to that described for Example 5, followed by purification by chiral SFC chromatography using a Regis Whelk-O (S,S) column, eluting with 20% methanol in supercritical $CO_2$. $^1$H NMR (400 MHz, DMSO-d$_6$) δ 11.58 (d, J=2.1 Hz, 1H), 7.63 (d, J=8.2 Hz, 1H), 7.36 (dd, J=8.6, 7.2 Hz, 2H), 7.17 (d, J=8.3 Hz, 3H), 7.05 (s, 1H), 6.64 (s, 1H), 6.12 (dd, J=12.9, 9.9 Hz, 1H), 5.57 (dd, J=8.1, 2.2 Hz, 1H), 4.84 (hept, J=6.3 Hz, 1H), 4.39 (dd, J=12.1, 5.7 Hz, 1H), 4.34-4.25 (m, 1H), 4.04 (s, 2H), 3.81-3.68 (m, 1H), 1.19 (d, J=7.2 Hz, 3H), 1.13 (dd, J=6.3, 2.6 Hz, 6H).

Example 23. Isopropyl ((((2R,3R,4R,5R)-4-bromo-4-chloro-5-(2,4-dioxo-3,4-dihydropyrimidin-1(2H)-yl)-3-hydroxytetrahydrofuran-2-yl)methoxy)(m-tolyloxy)phosphoryl)-L-alaninate

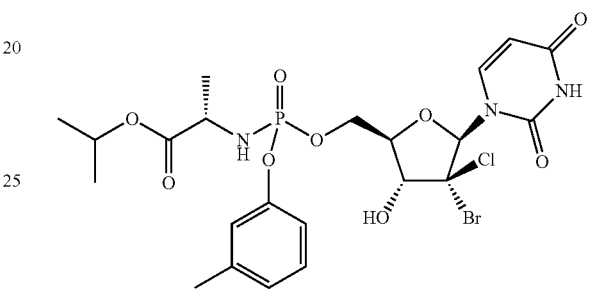

The title compound was prepared using a method similar to that described for Example 5. $^1$H NMR (400 MHz, DMSO-d$_6$) δ 11.56 (d, J=1.9 Hz, 1H), 7.61 (d, J=8.1 Hz, 1H), 7.21 (t, J=7.8 Hz, 1H), 6.98 (dd, J=12.5, 6.3 Hz, 3H), 6.64-6.57 (m, 1H), 6.12-5.97 (m, 1H), 5.54 (dd, J=8.1, 2.3 Hz, 1H), 4.83 (hept, J=6.2 Hz, 1H), 4.37-4.20 (m, 2H), 4.12-3.93 (m, 2H), 3.83-3.70 (m, 1H), 2.25 (s, 3H), 1.22-1.16 (m, 3H), 1.15-1.09 (m, 6H).

Example 24. Isopropyl ((((2R,3R,4R,5R)-4-bromo-4-chloro-5-(2,4-dioxo-3,4-dihydropyrimidin-1(2H)-yl)-3-hydroxytetrahydrofuran-2-yl)methoxy)(4-fluorophenoxy)phosphoryl)-L-alaninate

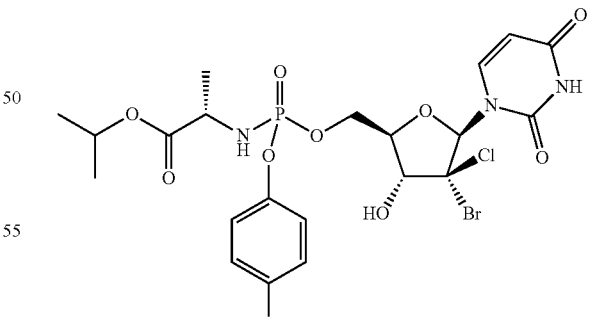

The title compound was prepared using a method similar to that described for Example 5. $^1$H NMR (400 MHz, DMSO-d$_6$) δ 11.58 (s, 1H), 7.64 (d, J=8.3 Hz, 1H), 7.28-7.15 (m, 3H), 7.09-6.94 (m, 1H), 6.67-6.59 (m, 1H), 6.19-6.04 (m, 1H), 5.64-5.56 (m, 1H), 4.84 (hept, J=6.3 Hz, 1H), 4.42-4.22 (m, 2H), 4.13-3.94 (m, 2H), 3.86-3.69 (m, 1H), 1.25-1.17 (m, 3H), 1.13 (d, J=6.3 Hz, 6H).

Example 25. Isopropyl ((((2R,3R,4R,5R)-4-bromo-4-chloro-5-(2,4-dioxo-3,4-dihydropyrimidin-1(2H)-yl)-3-hydroxytetrahydrofuran-2-yl)methoxy)(3-fluorophenoxy)phosphoryl)-L-alaninate

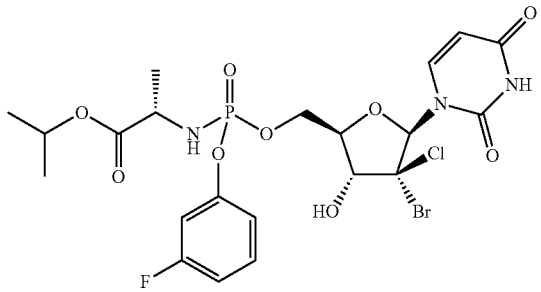 [SMILES: CC(C)OC(=O)[C@H](C)NP(=O)(OC[C@H]1O[C@@H](n2ccc(=O)[nH]c2=O)[C@](Cl)(Br)[C@@H]1O)Oc1cccc(F)c1]

The title compound was prepared using a method similar to that described for Example 5. ¹H NMR (500 MHz, DMSO-d₆) δ 11.62 (d, J=2.2 Hz, 1H), 7.66 (d, J=8.1 Hz, 1H), 7.48-7.39 (m, 1H), 7.17-6.99 (m, 4H), 6.65 (s, 1H), 6.22 (dd, J=13.1, 10.0 Hz, 1H), 5.62 (dd, J=8.2, 2.2 Hz, 1H), 4.86 (hept, J=6.1 Hz, 1H), 4.42-4.27 (m, 2H), 4.16-3.98 (m, 2H), 3.90-3.76 (m, 1H), 1.24 (d, J=7.1 Hz, 3H), 1.16 (d, J=6.2 Hz, 6H).

Example 26. Isopropyl ((((2R,3R,4R,5R)-4-bromo-4-chloro-5-(2,4-dioxo-3,4-dihydropyrimidin-1(2H)-yl)-3-hydroxytetrahydrofuran-2-yl)methoxy) (phenoxy)phosphoryl)glycinate

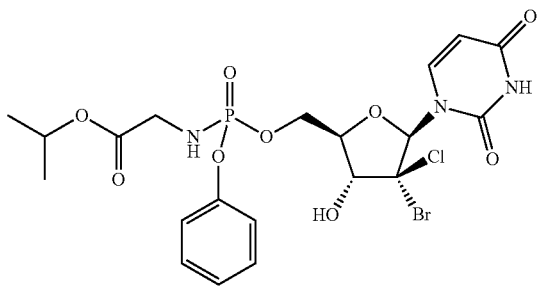 [SMILES: CC(C)OC(=O)CNP(=O)(OC[C@H]1O[C@@H](n2ccc(=O)[nH]c2=O)[C@](Cl)(Br)[C@@H]1O)Oc1ccccc1]

The title compound was prepared using a method similar to that described for Example 5. ¹H NMR (400 MHz, DMSO-d₆) δ 11.60-11.55 (m, 1H), 7.69-7.56 (m, 1H), 7.36 (t, J=7.8 Hz, 2H), 7.25-7.13 (m, 3H), 7.00 (s, 1H), 6.63 (s, 1H), 6.07-5.91 (m, 1H), 5.62-5.52 (m, 1H), 4.88 (hept, J=6.5 Hz, 1H), 4.46-4.23 (m, 2H), 4.14-3.95 (m, 2H), 3.65-3.55 (m, 2H), 1.19-1.10 (m, 6H).

Example 27. Sec-butyl ((((2R,3R,4R,5R)-4-bromo-4-chloro-5-(2,4-dioxo-3,4-dihydropyrimidin-1(2H)-yl)-3-hydroxytetrahydrofuran-2-yl)methoxy)(phenoxy)phosphoryl)-L-alaninate

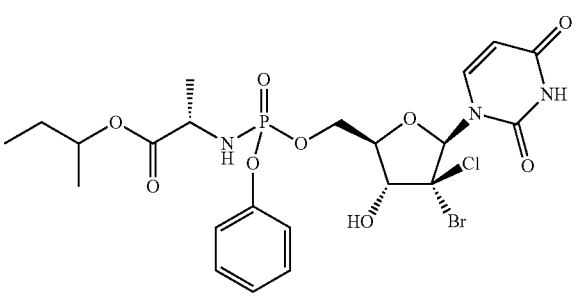 [SMILES: CCC(C)OC(=O)[C@H](C)NP(=O)(OC[C@H]1O[C@@H](n2ccc(=O)[nH]c2=O)[C@](Cl)(Br)[C@@H]1O)Oc1ccccc1]

The title compound was prepared using a method similar to that described for Example 5. ¹H NMR (400 MHz, DMSO-d₆) δ 11.56 (d, J=2.2 Hz, 1H), 7.62 (d, J=8.2 Hz, 1H), 7.34 (dd, J=8.6, 7.2 Hz, 2H), 7.23-7.11 (m, 3H), 6.97 (s, 1H), 6.65-6.57 (m, 1H), 6.16-6.00 (m, 1H), 5.55 (dd, J=8.2, 2.2 Hz, 1H), 4.68 (h, J=6.3 Hz, 1H), 4.40-4.21 (m, 2H), 4.12-3.93 (m, 2H), 3.88-3.71 (m, 1H), 1.51-1.41 (m, 2H), 1.24-1.15 (m, 3H), 1.11-1.05 (m, 3H), 0.78 (t, J=7.4 Hz, 3H).

Example 28. 1-methoxypropan-2-yl ((((2R,3R,4R,5R)-4-bromo-4-chloro-5-(2,4-dioxo-3,4-dihydropyrimidin-1(2H)-yl)-3-hydroxytetrahydrofuran-2-yl)methoxy)(phenoxy)phosphoryl)-L-alaninate

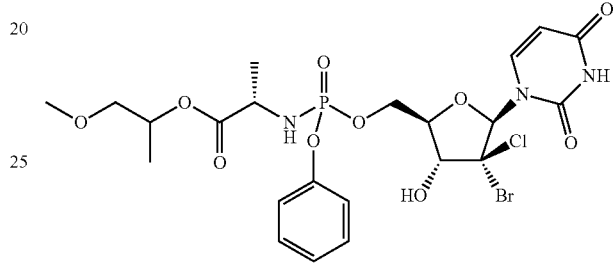

The title compound was prepared using a method similar to that described for Example 5. ¹H NMR (501 MHz, DMSO-d₆) δ 11.60-11.56 (m, 1H), 7.67-7.59 (m, 1H), 7.40-7.32 (m, 2H), 7.24-7.14 (m, 3H), 7.10-6.91 (m, 1H), 6.66-6.60 (m, 1H), 6.19-6.06 (m, 1H), 5.60-5.54 (m, 1H), 4.96-4.86 (m, 1H), 4.42-4.24 (m, 2H), 4.12-3.96 (m, 2H), 3.89-3.76 (m, 1H), 3.33-3.28 (m, 1H), 3.23-3.21 (m, 3H), 1.25-1.18 (m, 3H), 1.11-1.08 (m, 3H).

Example 29. (2S)-2-(((((2R,3R,4R,5R)-4-bromo-4-chloro-5-(2,4-dioxo-3,4-dihydropyrimidin-1(2H)-yl)-3-hydroxytetrahydrofuran-2-yl)methoxy)(phenoxy)phosphoryl)amino)propyl isobutyrate

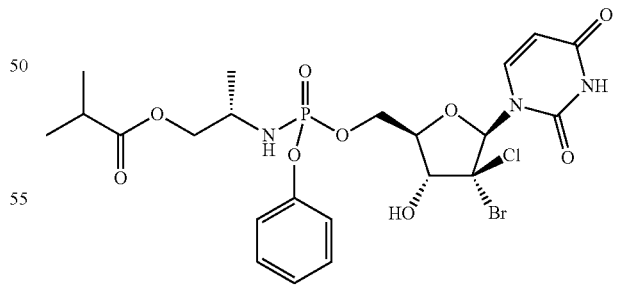

The title compound was prepared using a method similar to that described for Example 5. ¹H NMR (400 MHz, DMSO-d₆) δ 11.63-11.46 (m, 1H), 7.67-7.56 (m, 1H), 7.40-7.30 (m, 2H), 7.23-7.10 (m, 3H), 7.00 (s, 1H), 6.65-6.58 (m, 1H), 5.70-5.50 (m, 2H), 4.30 (dp, J=9.8, 5.7 Hz, 2H), 4.13-3.95 (m, 2H), 3.89-3.73 (m, 2H), 2.49-2.38 (m, 1H), 1.02 (dd, J=7.0, 1.6 Hz, 9H).

Example 30. (2S)-2-(((((2R,3R,4R,5R)-4-bromo-4-chloro-5-(2,4-dioxo-3,4-dihydropyrimidin-1(2H)-yl)-3-hydroxytetrahydrofuran-2-yl)methoxy)(phenoxy)phosphoryl)amino)propyl propionate

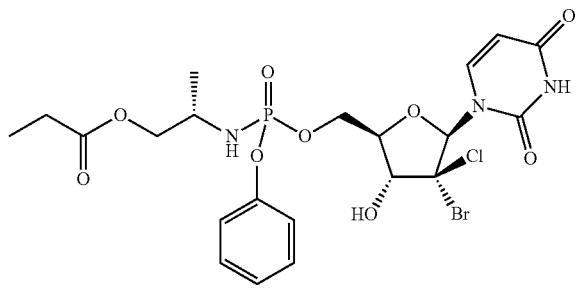 [SMILES: CCC(=O)OC[C@H](C)NP(=O)(OC[C@H]1O[C@@H](n2ccc(=O)[nH]c2=O)[C@](Cl)(Br)[C@@H]1O)Oc1ccccc1]

The title compound was prepared using a method similar to that described for Example 5. $^1$H NMR (400 MHz, DMSO-d$_6$) δ 11.59-11.55 (m, 1H), 7.67-7.58 (m, 1H), 7.39-7.31 (m, 2H), 7.23-7.11 (m, 3H), 7.01 (s, 1H), 6.64-6.59 (m, 1H), 5.66-5.50 (m, 2H), 4.38-4.23 (m, J=6.4 Hz, 2H), 4.12-3.94 (m, 2H), 3.86-3.77 (m, 2H), 2.22 (qd, J=7.5, 1.4 Hz, 2H), 1.03-0.98 (m, 3H), 0.95 (t, J=7.5 Hz, 3H).

Example 31. (2S)-2-(((((2R,3R,4R,5R)-4-bromo-4-chloro-5-(2,4-dioxo-3,4-dihydropyrimidin-1(2H)-yl)-3-hydroxytetrahydrofuran-2-yl)methoxy)(phenoxy)phosphoryl)amino)propyl 3-methoxy-2-methylpropanoate

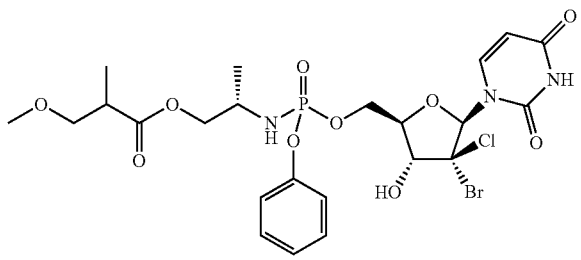 [SMILES: COCC(C)C(=O)OC[C@H](C)NP(=O)(OC[C@H]1O[C@@H](n2ccc(=O)[nH]c2=O)[C@](Cl)(Br)[C@@H]1O)Oc1ccccc1]

The title compound was prepared using a method similar to that described for Example 5. $^1$H NMR (501 MHz, DMSO-d$_6$) δ 11.69-11.50 (m, 1H), 7.69-7.59 (m, 1H), 7.37 (dd, J=8.7, 7.3 Hz, 2H), 7.24-7.13 (m, 3H), 7.09-6.96 (m, 1H), 6.67-6.60 (m, 1H), 5.70-5.52 (m, 2H), 4.40-4.25 (m, 2H), 4.14-3.97 (m, 2H), 3.93-3.76 (m, 2H), 3.46-3.39 (m, 2H), 3.18 (d, J=1.3 Hz, 3H), 2.68-2.58 (m, 1H), 1.06-0.98 (m, 6H).

Example 32. (2S)-2-(((((2R,3R,4R,5R)-4-bromo-4-chloro-5-(2,4-dioxo-3,4-dihydropyrimidin-1(2H)-yl)-3-hydroxytetrahydrofuran-2-yl)methoxy)(phenoxy)phosphoryl)amino)propyl 2-methoxyacetate

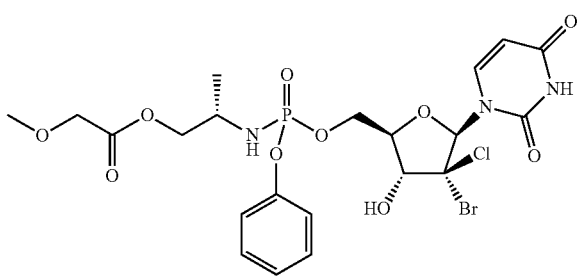 [SMILES: COCC(=O)OC[C@H](C)NP(=O)(OC[C@H]1O[C@@H](n2ccc(=O)[nH]c2=O)[C@](Cl)(Br)[C@@H]1O)Oc1ccccc1]

The title compound was prepared using a method similar to that described for Example 5. $^1$H NMR (501 MHz, DMSO-d$_6$) δ 11.67-11.48 (m, 1H), 7.69-7.59 (m, 1H), 7.42-7.34 (m, 2H), 7.24-7.14 (m, 3H), 7.12-6.90 (m, 1H), 6.66-6.60 (m, 1H), 5.70-5.51 (m, 2H), 4.41-4.26 (m, 2H), 4.12-3.99 (m, 2H), 3.98-3.86 (m, 5H), 3.46-3.37 (m, 2H), 1.07-0.99 (m, 3H).

Example 33. (2S)-2-(((((2R,3R,4R,5R)-4-bromo-4-chloro-5-(2,4-dioxo-3,4-dihydropyrimidin-1(2H)-yl)-3-hydroxytetrahydrofuran-2-yl)methoxy)(phenoxy)phosphoryl)amino)propyl pivalate

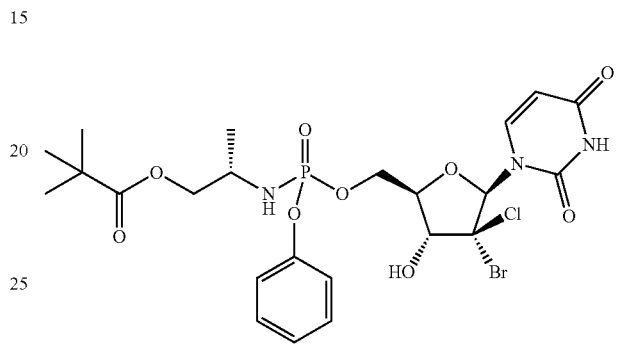

The title compound was prepared using a method similar to that described for Example 5. $^1$H NMR (400 MHz, DMSO-d$_6$) δ 11.58 (s, 1H), 7.65 (d, J=8.2 Hz, 1H), 7.41-7.33 (m, 2H), 7.25-7.13 (m, 3H), 7.02 (d, J=5.6 Hz, 1H), 6.63 (s, 1H), 5.64 (dd, J=12.5, 9.8 Hz, 1H), 5.56 (dd, J=8.2, 2.2 Hz, 1H), 4.32 (d, J=5.8 Hz, 2H), 4.14-3.97 (m, 2H), 3.87 (dd, J=10.7, 5.7 Hz, 1H), 3.76 (dd, J=10.7, 6.4 Hz, 1H), 3.48-3.37 (m, 1H), 1.13-0.98 (m, 12H).

Example 34. (2S)-2-(((((2R,3R,4R,5R)-4-bromo-4-chloro-5-(2,4-dioxo-3,4-dihydropyrimidin-1(2H)-yl)-3-hydroxytetrahydrofuran-2-yl)methoxy)(phenoxy)phosphoryl)amino)propyl (methoxycarbonyl)-L-valinate

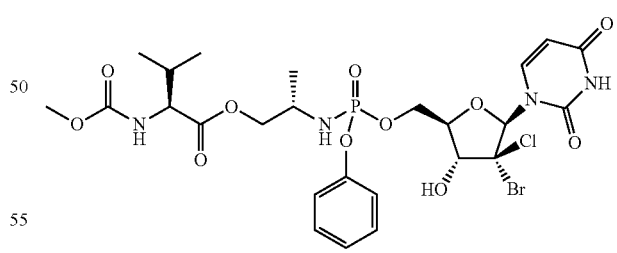

The title compound was prepared using a method similar to that described for Example 5. $^1$H NMR (400 MHz, DMSO-d$_6$) δ 11.58 (s, 1H), 7.66-7.59 (m, 1H), 7.47 (d, J=8.6 Hz, 1H), 7.37 (t, J=7.9 Hz, 2H), 7.24-7.14 (m, 3H), 7.02 (s, 1H), 6.63 (s, 1H), 5.69-5.60 (m, 1H), 5.56 (dd, J=8.2, 2.2 Hz, 1H), 4.37-4.27 (m, 2H), 4.13-3.99 (m, 2H), 3.98-3.88 (m, 2H), 3.81 (dd, J=10.7, 6.2 Hz, 1H), 3.53 (s, 3H), 2.08-1.96 (m, 1H), 1.04 (dd, J=6.7, 3.9 Hz, 3H), 0.82 (dd, J=6.8, 3.1 Hz, 6H).

Example 35. (2R,3R,4R,5R)-4-bromo-4-chloro-5-(2,4-dioxo-3,4-dihydropyrimidin-1(2H)-yl)-2-((((((S)-1-isopropoxy-1-oxopropan-2-yl)amino)(phenoxy)phosphoryl)oxy)methyl)tetrahydrofuran-3-yl 3-hydroxy-3-methylbutanoate

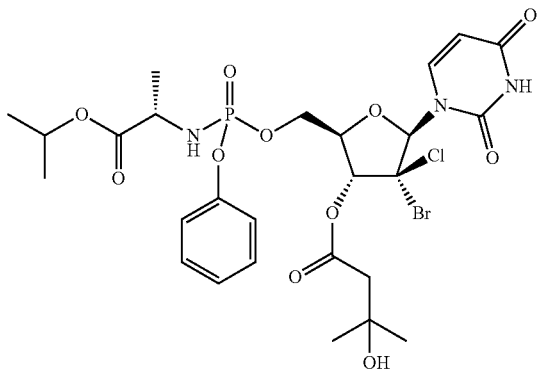 [SMILES: CC(C)OC(=O)[C@H](C)NP(=O)(OC[C@H]1O[C@@H](n2ccc(=O)[nH]c2=O)[C@](Cl)(Br)[C@@H]1OC(=O)CC(C)(C)O)Oc1ccccc1]

A mixture of the product from Example 1I (128 mg, 0.210 mmol), 3-hydroxy-3-methylbutanoic acid (24.76 mg, 0.210 mmol), N,N-dimethylpyridin-4-amine (2.56 mg, 0.021 mmol) and EDCI (60.0 mg, 0.314 mmol) in dichloromethane (2 ml) was stirred at rt overnight. The mixture was partitioned between water and dichloromethane, and the organic layer was separated and dried over sodium sulfate. The drying agent was filtered off, and the solution was concentrated in vacuo. The residue was purified by column chromatography on silica gel using a solvent gradient of 1-10% methanol in dichloromethane to give the title compound. $^1$H NMR (400 MHz, DMSO-d$_6$) δ 11.61 (d, J=2.3 Hz, 1H), 7.73 (d, J=8.1 Hz, 1H), 7.34 (dd, J=8.6, 7.2 Hz, 2H), 7.23-7.11 (m, 3H), 6.59 (s, 1H), 6.04 (dd, J=13.0, 10.1 Hz, 1H), 5.63 (dd, J=8.2, 2.2 Hz, 1H), 5.50 (s, 1H), 4.83 (hept, J=6.2 Hz, 1H), 4.37-4.21 (m, 3H), 3.84-3.70 (m, 1H), 2.54 (s, 2H), 1.22 (d, J=3.8 Hz, 6H), 1.20 (d, J=7.1 Hz, 3H), 1.12 (dd, J=6.2, 1.8 Hz, 6H).

Example 36. Ethyl 1-(((((2R,3R,4R,5R)-4-bromo-4-chloro-5-(2,4-dioxo-3,4-dihydropyrimidin-1(2H)-yl)-3-hydroxytetrahydrofuran-2-yl)methoxy)(phenoxy)phosphoryl)amino)cyclopropane-1-carboxylate

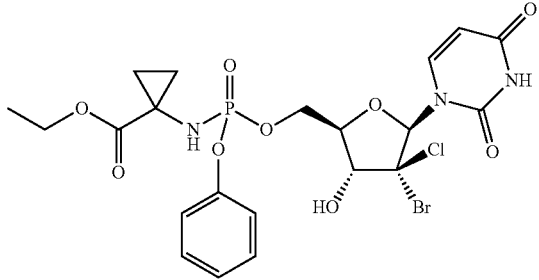 [SMILES: CCOC(=O)C1(NP(=O)(OC[C@H]2O[C@@H](n3ccc(=O)[nH]c3=O)[C@](Cl)(Br)[C@@H]2O)Oc2ccccc2)CC1]

The title compound was prepared using a method similar to that described for Example 5. $^1$H NMR (501 MHz, DMSO-d$_6$) δ 11.58 (s, 1H), 7.70-7.57 (m, 1H), 7.41-7.32 (m, 2H), 7.21-7.14 (m, 3H), 7.02 (s, 1H), 6.65-6.51 (m, 2H), 5.55 (dd, J=8.1, 2.2 Hz, 1H), 4.44-4.27 (m, 2H), 4.13-3.95 (m, 4H), 1.30-1.23 (m, 2H), 1.13-1.08 (m, 3H), 1.07-0.91 (m, 2H).

Example 37. Isopropyl 1-(((((2R,3R,4R,5R)-4-bromo-4-chloro-5-(2,4-dioxo-3,4-dihydropyrimidin-1(2H)-yl)-3-hydroxytetrahydrofuran-2-yl)methoxy)(phenoxy)phosphoryl)amino)cyclopropane-1-carboxylate

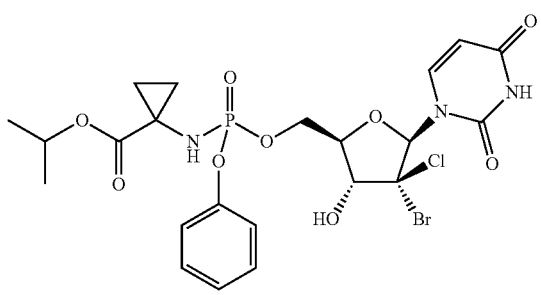 [SMILES: CC(C)OC(=O)C1(NP(=O)(OC[C@H]2O[C@@H](n3ccc(=O)[nH]c3=O)[C@](Cl)(Br)[C@@H]2O)Oc2ccccc2)CC1]

The title compound was prepared using a method similar to that described for Example 5. $^1$H NMR (400 MHz, DMSO-d$_6$) δ 11.62-11.57 (m, 1H), 7.68-7.55 (m, 1H), 7.41-7.31 (m, 2H), 7.23-7.13 (m, 3H), 7.11-6.94 (m, 1H), 6.67-6.58 (m, 11H), 6.53 (d, J=15.7 Hz, 1H), 5.55 (dd, J=8.2, 2.2 Hz, 1H), 4.81 (hept, J=6.3 Hz, 1H), 4.46-4.27 (m, 2H), 4.14-3.94 (m, 2H), 1.29-1.20 (m, 2H), 1.14-1.07 (m, 6H), 1.07-0.87 (m, 2H).

Example 38. Ethyl 2-(((((2R,3R,4R,5R)-4-bromo-4-chloro-5-(2,4-dioxo-3,4-dihydropyrimidin-1(2H)-yl)-3-hydroxytetrahydrofuran-2-yl)methoxy)(phenoxy)phosphoryl)amino)-3-methoxy-2-methylpropanoate

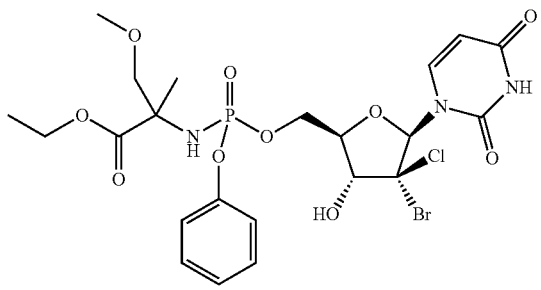 [SMILES: CCOC(=O)C(C)(COC)NP(=O)(OC[C@H]1O[C@@H](n2ccc(=O)[nH]c2=O)[C@](Cl)(Br)[C@@H]1O)Oc1ccccc1]

The title compound was prepared using a method similar to that described for Example 5. $^1$H NMR (500 MHz, DMSO-d$_6$) δ 11.61 (d, J=2.6 Hz, 1H), 7.73-7.61 (n, 1H), 7.43-7.35 (m, 2H), 7.27-7.16 (m, 3H), 7.11-7.00 (m, 1H), 6.70-6.63 (m, 1H), 5.84-5.71 (m, 1H), 5.59-5.52 (m, 1H), 4.45-4.27 (m, 2H), 4.18-3.99 (m, 4H), 3.24-3.19 (m, 3H), 1.43-1.31 (m, 3H), 1.19-1.11 (m, 3H).

Example 39. Ethyl N-((((2R,3R,4R,5R)-4-bromo-4-chloro-5-(2,4-dioxo-3,4-dihydropyrimidin-1(2H)-yl)-3-hydroxytetrahydrofuran-2-yl)methoxy)(phenoxy)phosphoryl)-O-methyl-L-threoninate

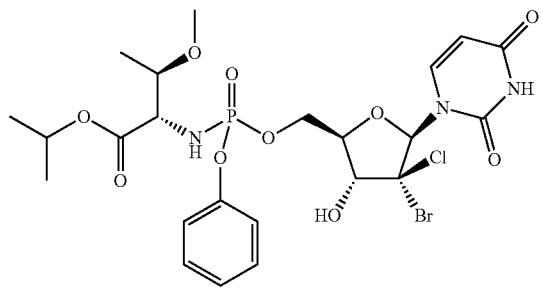 [SMILES: CO[C@H](C)[C@H](NP(=O)(OC[C@H]1O[C@@H](n2ccc(=O)[nH]c2=O)[C@](Cl)(Br)[C@@H]1O)Oc1ccccc1)C(=O)OC(C)C]

The title compound was prepared using a method similar to that described for Example 5. ¹H NMR (400 MHz, DMSO-d₆) δ 11.56 (d, J=2.2 Hz, 1H), 7.62 (d, J=8.2 Hz, 1H), 7.36-7.29 (m, 2H). 7.22-7.16 (m, 2H), 7.17-7.10 (m, 1H), 7.01-6.92 (m, 1H), 6.60 (s, 1H), 5.81 (t, J=11.3 Hz, 1H), 5.54 (dd, J=8.1, 2.2 Hz, 1H), 4.84 (hept, J=6.3 Hz, 1H), 4.40-4.22 (m, 2H), 4.12-3.94 (m, 2H), 3.82-3.71 (m, 1H), 3.67-3.57 (m, 1H), 3.17 (s, 3H), 1.11 (dd, J=6.2, 4.7 Hz, 6H), 1.05 (d, J=6.2 Hz, 3H).

Example 40. ethyl 2-(((R)-(((2R,3R,4S,5R)-4-bromo-5-(2,4-dioxo-3,4-dihydropyrimidin-1(2H)-yl)-4-fluoro-3-hydroxytetrahydrofuran-2-yl)methoxy)(phenoxy)phosphoryl)amino)-2-methylpropanoate

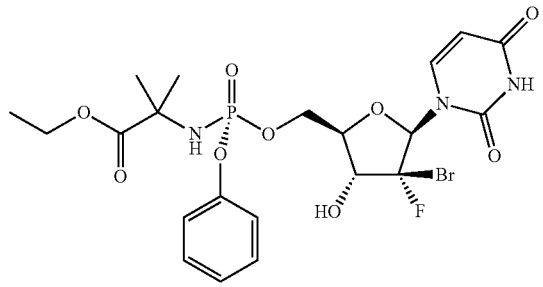 [SMILES: CCOC(=O)C(C)(C)N[P@@](=O)(OC[C@H]1O[C@@H](n2ccc(=O)[nH]c2=O)[C@@](F)(Br)[C@@H]1O)Oc1ccccc1]

The title compound was prepared using a method similar to that described for Example 5, substituting the product from Example 3E for the product from Example 1H. ¹H NMR (500 MHz, DMSO-d₆) δ 11.64 (s, 0H), 7.51 (d, J=8.2 Hz, 1H), 7.37 (t, J=7.9 Hz, 2H), 7.24-7.14 (m, 3H), 6.73 (d, J=6.8 Hz, 1H), 6.24 (d, J=17.6 Hz, 1H), 6.00 (d, J=9.6 Hz, 1H), 5.60 (d, J=8.1 Hz, 1H), 4.42-4.22 (m, 4H), 4.09-3.99 (m, 3H), 1.38 (s, 3H), 1.33 (s, 3H), 1.14 (t, J=7.1 Hz, 3H).

Example 41. ethyl 2-(((S)-(((2R,3R,4S,5R)-4-bromo-5-(2,4-dioxo-3,4-dihydropyrimidin-1(2H)-yl)-4-fluoro-3-hydroxytetrahydrofuran-2-yl)methoxy)(phenoxy)phosphoryl)amino)-2-methylpropanoate

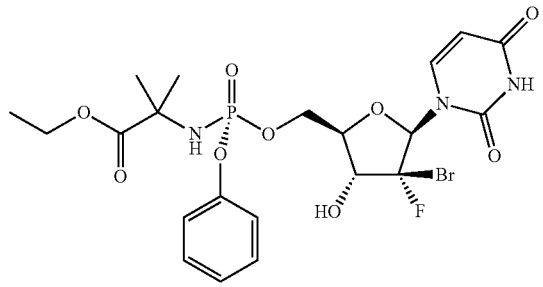 [SMILES: CCOC(=O)C(C)(C)N[P@@](=O)(OC[C@H]1O[C@@H](n2ccc(=O)[nH]c2=O)[C@@](F)(Br)[C@@H]1O)Oc1ccccc1]

The title compound was prepared using a method similar to that described for Example 5, substituting the product from Example 3E for the product from Example 1H. ¹H NMR (500 MHz, DMSO-d₆) δ 11.39 (s, 1H), 7.56 (d, J=8.1 Hz, 1H), 7.39-7.32 (m, 2H), 7.23-7.13 (m, 2H), 6.66 (s, 1H), 6.22 (d, J=17.7 Hz, 1H), 5.92 (d, J=9.6 Hz, 1H), 5.58 (d, J=8.1 Hz, 1H), 4.41-4.22 (m, 3H), 4.02 (q, J=7.1 Hz, 3H), 1.37 (s, 3H), 1.33 (s, 3H), 1.12 (t, J=7.1 Hz, 3H).

When tested, the compound of Example 41 showed similar anti-HCV potency as sofosbuvir, and provided a 6-fold higher liver triphosphate levels than sofosbuvir in a single-dose dog liver biopsy study. On repeat dosing (4 days QD), the liver triphosphate levels were comparable to sofosbuvir when given at a five-fold lower dose than sofosbuvir.

Example 42. ethyl 2-(((((2R,3R,4R,5R)-5-(2,4-dioxo-3,4-dihydropyrimidin-1(2H)-yl)-4-fluoro-3-hydroxy-4-methyltetrahydrofuran-2-yl)methoxy)(phenoxy)phosphoryl)amino)-2-methylpropanoate

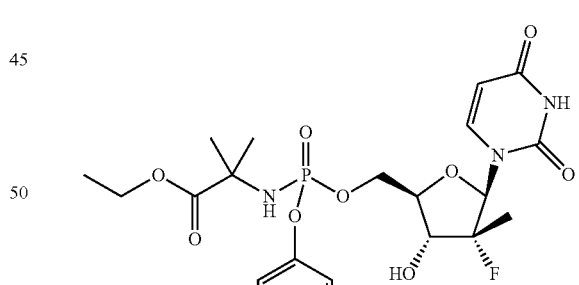

The title compound was obtained as a 2.5:1 mixture of phosphoramidate isomers: ¹H NMR (400 MHz, DMSO-d₆) δ 11.48 (s, 1H), 7.61-7.44 (m, 1H), 7.38-7.29 (m, 2H), 7.22-7.10 (m, 3H), 6.08-5.77 (m, 3H), 5.52-5.44 (m, 1H), 4.35 (dd, J=11.3, 6.1 Hz, 1H), 4.29-4.18 (m, 1H), 4.04-3.94 (m, 3H), 3.91-3.64 (m, 1H), 1.40-1.28 (m, 6H), 1.28-1.14 (m, 3H), 1.13-1.06 (m, 3H); MS (ESI) m/z @530.1 (M+H).

In human hepatocyte wash-out experiments (cells incubated for 4 hours with 100 μM of a compound of interest and then the active triphosphate was measured at 24 hours), the compound of Example 42 showed a significantly higher intracellular triphosphate concentration than sofosbuvir.

Example 43. ethyl 2-(((((2R,3R,4R,5R)-4-chloro-5-(2,4-dioxo-3,4-dihydropyrimidin-1(2H)-yl)-3-hydroxy-4-methyltetrahydrofuran-2-yl)methoxy)(phenoxy)phosphoryl)amino)-2-methylpropanoate

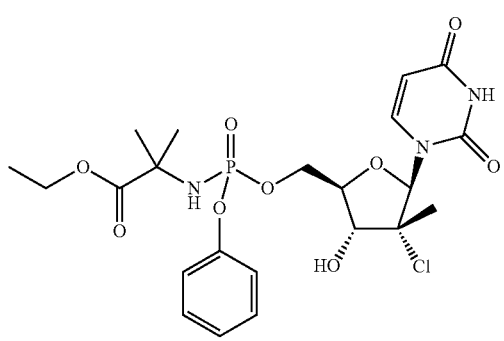 [SMILES: CCOC(=O)C(C)(C)NP(=O)(OC[C@H]1O[C@@H](n2ccc(=O)[nH]c2=O)[C@](C)(Cl)[C@@H]1O)Oc1ccccc1]

The title compound was obtained as a 2.5:1 mixture of phosphoramidate isomers: $^1$H NMR (400 MHz, DMSO-$d_6$) δ 11.48 (s, 1H), 7.70-7.52 (m, 1H), 7.41-7.30 (m, 2H), 7.24-7.09 (m, 3H), 6.24 (s, 1H), 6.18-6.08 (m, 1H), 6.00-5.86 (m, 1H), 5.49-5.39 (m, 1H), 4.44-4.22 (m, 2H), 4.10-3.77 (m, 4H), 1.41 (s, 3H), 1.36 (s, 3H), 1.31 (d, J=3.3 Hz, 3H), 1.13-1.07 (m, 3H); MS (ESI) m/z @ 546.1 (M+H).

In human hepatocyte wash-out experiments (cells incubated for 4 hours with 100 μM of a compound of interest and then the active triphosphate was measured at 24 hours), the compound of Example 43 showed a comparable or higher intracellular triphosphate concentration than sofosbuvir.

Example 44. ethyl 2-(((((2R,3R,5R)-4,4-dichloro-5-(2,4-dioxo-3,4-dihydropyrimidin-1(2H)-yl)-3-hydroxytetrahydrofuran-2-yl)methoxy)(phenoxy)phosphoryl)amino)-2-methylpropanoate

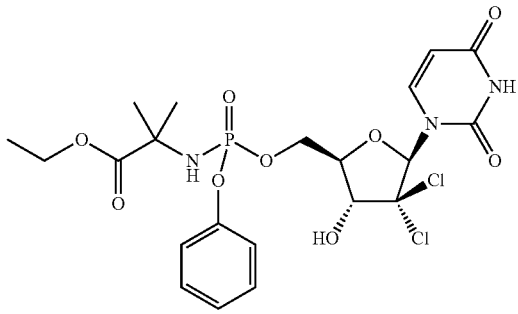

The title compound was obtained as a 2.2:1 mixture of phosphoramidate isomers: $^1$H NMR (400 MHz, DMSO-$d_6$) δ 11.58 (s, 1H), 7.67-7.55 (m, 1H), 7.39-7.30 (m, 2H), 7.23-7.05 (m, 3H), 7.05-6.93 (m, 1H), 6.43-6.37 (m, 1H), 6.03-5.93 (m, 1H), 5.55-5.48 (m, 1H), 4.42-4.21 (m, 3H), 4.07-3.92 (m, 3H), 1.40-1.26 (m, 6H), 1.16-1.06 (m, 3H); MS (ESI) m/z @ 566.1 (M+H).

In human hepatocyte wash-out experiments (cells incubated for 4 hours with 100 μM of a compound of interest and then the active triphosphate was measured at 24 hours), the compound of Example 44 showed an intracellular triphosphate concentration comparable to sofosbuvir.

Example 45. ethyl 2-(((((2R,3R,4R,5R)-4-bromo-4-chloro-5-(2,4-dioxo-3,4-dihydropyrimidin-1(2H)-yl)-3-hydroxytetrahydrofuran-2-yl)methoxy)(phenoxy)phosphoryl)amino)-2-methylpropanoate

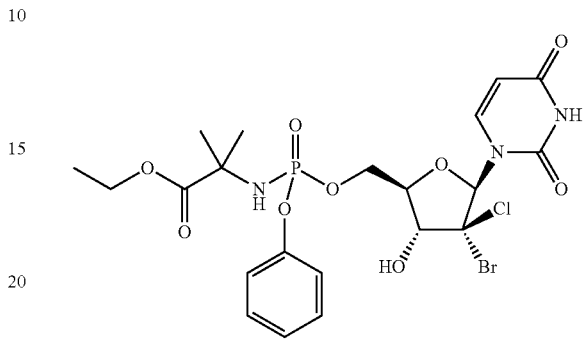

Example 45a. ethyl 2-(((((6-cyanopyridin-3-yl)oxy)(phenoxy)phosphoryl)amino)-2-methylpropanoate

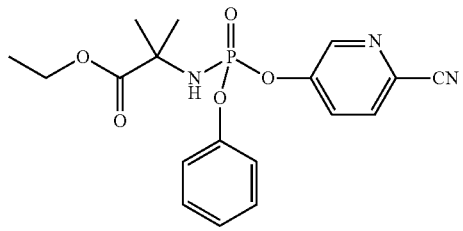 [SMILES: CCOC(=O)C(C)(C)NP(=O)(Oc1ccccc1)Oc1ccc(C#N)nc1]

To a solution of phenol (225 mg, 2.386 mmol) in anhydrous dichloromethane (20 ml) at −78° C. under a dry, inert atmosphere (N$_2$), was added phosphoryl trichloride (0.222 ml, 2.386 mmol)) in one portion. The resulting solution was stirred while triethylamine (1.00 ml, 7.17 mmol)) was added dropwise over 10 min. The resulting mixture was stirred at −78 C for 1 hr, and then was allowed to warm to an internal temperature of 0° C. and stirred for 30 min. The stirred mixture was then cooled to −78° C., and a solution of ethyl 2-amino-2-methylpropanoate hydrochloride (400 mg, 2.386 mmol)) in anhydrous dichloromethane (20 ml) was added dropwise over 20 min. The resulting mixture was stirred at −78 for 1 hr, and was then allowed to warm to an internal temperature of 0° C. To the stirred mixture at 0° C. was added a solution of 5-hydroxypicolinonitrile (287 mg, 2.386 mmol) and triethylamine (0.333 ml, 2.386 mmol)) in anhydrous dichloromethane (10 ml) slowly by dropwise addition. When the addition was complete, the suspension was allowed to warm to room temperature and stirred for 16 hr. The reaction mixture was washed with aqueous 1 M NaHSO$_4$ (30 mL). The layers were separated and the organic layer was dried over sodium sulfate. The drying agent was filtered off, and the filtrated was concentrated in vacuo to give a crude product that was purified by column chromatography on silica gel using a solvent gradient of 0-30% ethyl acetate in heptanes. The title compound was obtained as a colorless solid (208 mg, 22%).

Example 45b. ethyl 2-(((((2R,3R,4R,5R)-4-bromo-4-chloro-5-(2,4-dioxo-3,4-dihydropyrimidin-1(2H)-yl)-3-hydroxytetrahydrofuran-2-yl)methoxy) (phenoxy)phosphoryl)amino)-2-methylpropanoate

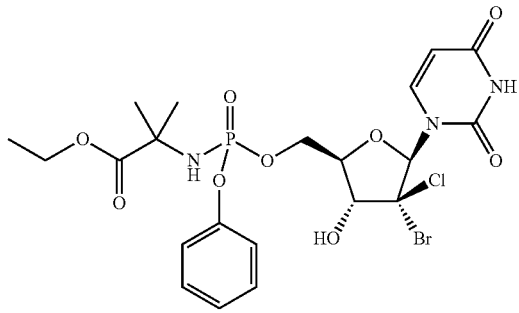 [SMILES: CCOC(=O)C(C)(C)NP(=O)(OC[C@H]1O[C@@H](n2ccc(=O)[nH]c2=O)[C@](Cl)(Br)[C@@H]1O)Oc1ccccc1]

A solution of the product from Example 1H (58 mg, 0.170 mmol) in anhydrous THF (1.5 ml), and DMPU (0.1 ml) was cooled to 0° C. A 1.0 M solution of tert-butylmagnesium chloride in THF (0.187 ml, 0.187 mmol) was added dropwise, and the resulting mixture was stirred for 30 min before the product from Example 45a (132 mg, 0.340 mmol) was added in one portion. The reaction mixture was allowed to warm to room temperature and stirred for 12 hrs. The reaction was quenched with a saturated solution of NH$_4$Cl, and the mixture was extracted with dichloromethane (2×). The combined organic layers were dried over sodium sulfate, filtered and concentrated in vacuo, and the product was isolated by C18 HPLC using a solvent gradient of 5-95% acetonitrile in water (0.1% TFA). The title compound was obtained as a colorless solid. $^1$H NMR (400 MHz, DMSO-d$_6$) δ 11.57 (d, J=2.3 Hz, 1H), 7.70-7.54 (m, 1H), 7.40-7.32 (m, 2H), 7.23-7.12 (m, 3H), 7.01 (s, 1H), 6.63 (s, 1H), 6.03-5.91 (m, 1H), 5.57-5.48 (m, 1H), 4.42-4.25 (m, 2H), 4.13-3.97 (m, 4H), 1.40-1.30 (m, 6H), 1.15-1.09 (m, 3H).

Example 46. (S)-isopropyl 2-(((S)-(((2R,3R,4S,5R)-4-bromo-4-chloro-5-(2,4-dioxo-3,4-dihydropyrimidin-1(2H)-yl)-3-hydroxytetrahydrofuran-2-yl)methoxy)(phenoxy)phosphoryl) amino)propanoate

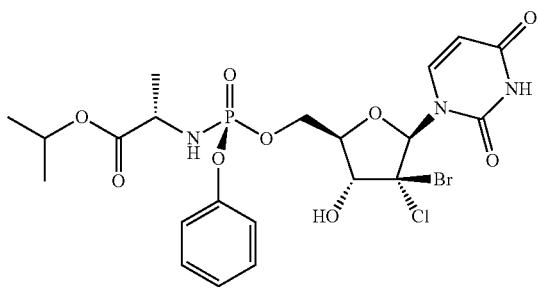 [SMILES: CC(C)OC(=O)[C@H](C)N[P@](=O)(OC[C@H]1O[C@@H](n2ccc(=O)[nH]c2=O)[C@@](Cl)(Br)[C@@H]1O)Oc1ccccc1]

Example 46A. (4S,5R)-4-((tert-butyldimethylsilyl)oxy)-5-(((tert-butyldimethylsilyl)oxy)methyl) dihydrofuran-2(3H)-one

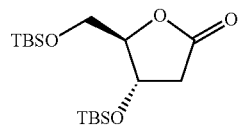 [SMILES: CC(C)(C)[Si](C)(C)OC[C@H]1OC(=O)C[C@@H]1O[Si](C)(C)C(C)(C)C]

To a solution of the product from Example 1A (1.95 kg, 14.7 mol), N,N-dimethylaminopyridine (90.1 g, 738 mmol) and imidazole (3.52 kg, 51.6 mol) in N,N-dimethylformamide (15.0 L) at 15° C. was added tert-butyldimethylsilyl chloride (5.34 kg, 35.4 mol) over ca. 45 min, and the mixture was stirred 12 hours. TLC (Petroleum ether:Ethyl acetate=20:1, R$_f$=0.40) indicated the starting material was consumed completely and one new spot formed. The reaction mixture was diluted with H$_2$O (60 L) and extracted with methyl tert-butyl ether (10 L×3). The combined organic layers were washed with brine (3 L), dried over Na$_2$SO$_4$, filtered and concentrated under reduced pressure to give a residue. The residue was purified by column chromatography on silica gel, eluting with a solvent gradient of 2-5% ethyl acetate in petroleum ether to give the title compound as a colorless solid (3.25 kg, 61% yield); $^1$H NMR (400 MHz, CDCl$_3$) □□4.49 (dt, J=6.4, 2.0 Hz, 1H), 4.30-4.32 (m, 1H), 3.71-3.82 (m, 2H), 2.77-2.83 (m, 1H), 2.34-2.43 (m, 1H), 0.82-0.92 (m, 18H), 0.03-0.09 (m, 12H).

Example 46B. (4R,5R)-4-((tert-butyldimethylsilyl)oxy)-5-(((tert-butyldimethylsilyl)oxy)methyl)-3-chlorodihydrofuran-2(3H)-one

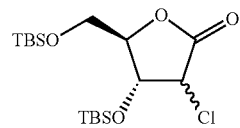 [SMILES: CC(C)(C)[Si](C)(C)OC[C@H]1OC(=O)C(Cl)[C@@H]1O[Si](C)(C)C(C)(C)C]

To a solution of the product from Example 46B (300 g, 831 mmol) and N-chlorosuccinimide (233 g, 1.75 mol) in tetrahydrofuran (2.0 L) at −65° C. was added a solution of lithium bis-trimethylsilylamide in tetrahydrofuran (1 M, 2.16 L) drop-wise over ca. 45 min. The mixture was stirred at −70° C. for 0.5 hours and then quenched with acetic acid (630 g, 10.5 mol). The mixture was warmed to 0° C. and Zn (81.5 g, 1.25 mol) was added in portions. The mixture was stirred at 20° C. for 12 hours. The reaction mixture was filtered with celite, and the filter cake was washed with methyl tert-butyl ether (1 L×3) and water (1 L×3). The mixture was diluted with water (15 L) and then the mixture was extracted with methyl tert-butyl ether (4000 mL×3). The combined organic layers were washed with brine (4 L), dried over Na$_2$SO$_4$, filtered and concentrated under reduced pressure to give a residue. The residue was dissolved with n-hexane (10 L) and cooled to −60° C. to give a colorless solid that was collected by filtration and dried to give the title compound as a colorless solid.

Example 46C. (3S,4R,5R)-3-bromo-4-((tert-butyldimethylsilyl)oxy)-5-(((tert-butyldimethylsilyl)oxy)methyl)-3-chlorodihydrofuran-2(3H)-one

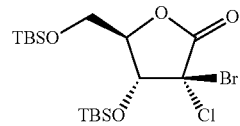 [SMILES: CC(C)(C)[Si](C)(C)OC[C@H]1OC(=O)[C@@](Cl)(Br)[C@@H]1O[Si](C)(C)C(C)(C)C]

To a solution of the product from Example 46B (50 g, 126 mmol) and 1,2-dibromo-1,1,2,2-tetrachloro-ethane (65 g, 202 mmol) in tetrahydrofuran (500 mL) −90° C. was added a solution of potassium bis-trimethylsilylamide in tetrahydrofuran (1 M, 269 mL) drop-wise over ca. 1.5 hours. The resulting mixture was stirred for 0.5 hours at −90° C. Methanol (40 mL) was added drop-wise at −90° C., and the mixture was extracted with methyl tert-butyl ether (200 mL×3). The combined organic layers were washed with brine (500 mL), dried over Na$_2$SO$_4$, filtered and concentrated under reduced pressure. The residue was purified by column chromatography on silica gel, eluting with a solvent gradient of 1-3% ethyl acetate in petroleum ether to give a crude compound, which was further purified by recrystallization from n-hexane (60 mL) at −60° C. to give the title compound as a colorless solid (18 g); $^1$H NMR (400 MHz, CDCl$_3$) □□ 4.83 (d, J=7.2 Hz, 1H), 4.12 (d, J=7.2 Hz, 1H), 3.94 (d, J=12.4 Hz, 1H), 3.72 (d, J=12.4 Hz, 1H), 0.89 (s, 9H), 0.81 (s, 9H), 0.21 (s, 3H), 0.11 (s, 3H), 0.04 (s, 6H).

Example 46D. (3S,4R,5R)-3-bromo-4-((tert-butyldimethylsilyl)oxy)-5-(((tert-butyldimethylsilyl)oxy)methyl)-3-chlorotetrahydrofuran-2-ol

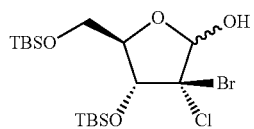

To a solution of the product from Example 46C (1.0 g, 1.792 mmol) in anhydrous toluene (10 ml) at −78° C. was added diisobutylaluminum hydride (1.0 M in toluene, 2.15 ml, 2.15 mmol) dropwise over 5 minutes. The resulting mixture was stirred at −78° C. for 90 minutes. Methanol (0.5 ml) was added and the mixture was allowed to stir and slowly warm to room temperature. Aqueous 1 N HCl (10 ml) and ethyl acetate (10 ml) were added, and the mixture was stirred at room temperature for 30 minutes. The layers were separated, and the aqueous layer was washed with ethyl acetate (10 ml). The combined organic layers were dried over Na$_2$SO$_4$, and then filtered and concentrated in vacuo to give a colorless oil that slowly crystallized under vacuum. The title compound was obtained as a colorless solid (1.0 g, 100%).

Example 46E. (3S,4R,5R)-3-bromo-4-((tert-butyldimethylsilyl)oxy)-5-(((tert-butyldimethylsilyl)oxy)methyl)-3-chlorotetrahydrofuran-2-yl 4-methoxybenzoate

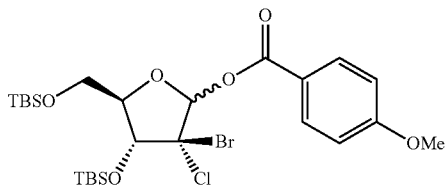 [SMILES: COc1ccc(C(=O)OC2O[C@H](CO[Si](C)(C)C(C)(C)C)[C@@H](O[Si](C)(C)C(C)(C)C)[C@]2(Cl)Br)cc1]

To a solution of the product from Example 46D (1.0 g, 1.79 mmol) and triethylamine (0.25 ml, 1.79 mmol) in anhydrous dichloromethane (12 ml) at 0° C. was added 4-methoxybenzoyl chloride (0.335 g, 1.964 mmol) and the mixture was stirred at 0° C. for 10 minutes. 4-Dimethylaminopyridine (0.022 g, 0.179 mmol) was added, and the mixture was allowed to warm to room temperature and stirred for 90 minutes. The reaction mixture was partitioned between water and dichloromethane (3×), and the combined organic layers dried over Na$_2$SO$_4$, filtered and concentrated in vacuo. The crude product was purified by column chromatography on silica gel using a solvent gradient of 0-20% ethyl acetate in heptanes. The title compound was obtained as a colorless oil (1.17 g, 94%).

Example 46F. (3S,4R,5R)-3-bromo-3-chloro-5-(((4-methoxybenzoyl)oxy)methyl)tetrahydrofuran-2,4-diyl bis(4-methoxybenzoate)

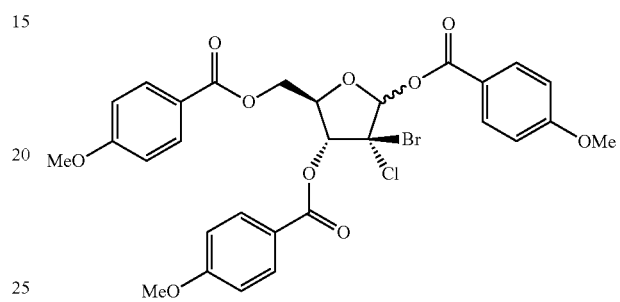

To a solution of the product from Example 46E (1.17 g, 1.685 mmol) and acetic acid (0.193 ml, 3.37 mmol) in tetrahydrofuran (17 ml) at 0° C. was added tetra-N-butylammonium fluoride (1.0M in THF, 3.71 ml, 3.71 mmol) and the mixture was stirred at 0° C. for 3 hours. The mixture was allowed to warm to room temperature and stirred for 30 minutes, and was then partitioned between water and ethyl acetate (3×). The combined organic layers were dried over Na$_2$SO$_4$, filtered and concentrated in vacuo. The residue was dissolved in anhydrous dichloromethane (17 ml), and 4-methoxybenzoyl chloride (0.719 g, 4.21 mmol), triethylamine (0.705 ml, 5.06 mmol), and 4-dimethylaminopyridine (0.021 g, 0.169 mmol) were added. The resulting mixture was stirred at room temperature overnight, and was then partitioned between water and dichloromethane. The organic layer was dried over Na$_2$SO$_4$, filtered and concentrated in vacuo, and the crude product was purified on silica gel using a solvent gradient of 0-20% ethyl acetate in heptanes. The title compound was obtained as a colorless solid (0.46 g, 42%).

Example 46G. (2R,3R,4S)-5-(4-benzamido-2-oxopyrimidin-1(2H)-yl)-4-bromo-4-chloro-2-(((4-methoxybenzoyl)oxy)methyl)tetrahydrofuran-3-yl 4-methoxybenzoate

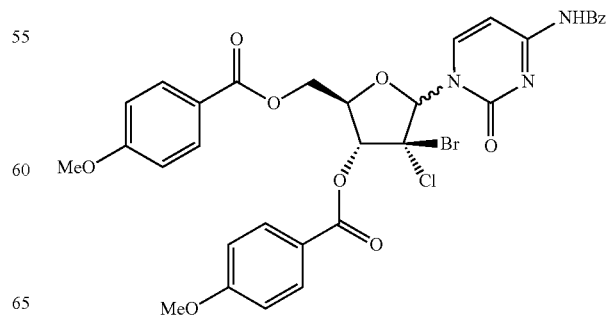

A mixture of N-benzoyl-cytosine (0.149 g, 0.692 mmol) and trimethylsilyl N-(trimethylsilyl)acetimidate (0.203 ml, 0.830 mmol) in anhydrous chlorobenzene (1.0 ml) was stirred at 80° C. under a dry $N_2$ atmosphere for 90 minutes. The resulting solution was cooled to room temperature, and a solution of the product from Example 46F (0.15 g, 0.231 mmol) in chlorobenzene (1.0 ml) was added, followed by tin tetrachloride (0.163 ml, 1.385 mmol). The resulting mixture was stirred at 80° C. under a dry $N_2$ atmosphere for 16 hours. The cooled mixture was diluted with ethyl acetate (3 ml), and washed with saturated aqueous sodium bicarbonate (3 ml). The layers were separated, and the aqueous layer was washed with ethyl acetate (2×3 ml). The combined org layers were dried over $Na_2SO_4$, filtered and concentrated in vacuo to give a crude product that was purified by column chromatography on silica gel using a solvent gradient of 0-60% ethyl acetate in heptanes to give the title compound (96 mg, 58%).

Example 46H. 1-((2R,3S,4R,5R)-3-bromo-3-chloro-4-hydroxy-5-(hydroxymethyl)tetrahydrofuran-2-yl)pyrimidine-2,4(1H,3H)-dione

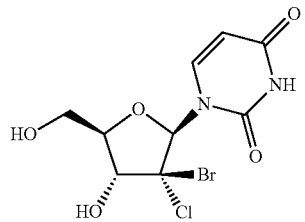 [SMILES: O=c1ccn([C@@H]2O[C@H](CO)[C@@H](O)[C@]2(Cl)Br)c(=O)[nH]1]

A solution of the product from Example 46G (95 mg, 0.133 mmol) in acetic acid (1.2 ml) and water (0.3 ml) was stirred at 110° C. for 4 hours. The mixture was concentrated in vacuo, and the residue was dissolved in ammonia (7 M in methanol, 1.0 ml, 7.00 mmol) and stirred at room temperature for 3 days. The mixture was concentrated in vacuo, and the crude product was purified by column chromatography on silica gel using a solvent gradient of 0-5% methanol in dichloromethane. The anomeric mixture of products eluted at 5% methanol as an overlapping pair of peaks, with the desired beta anomer eluting first. Mixed fractions were repurified using the same conditions. The title compound was obtained as a colorless solid (13 mg, 29%).

Example 46I. (S)-isopropyl 2-(((S)-(((2R,3R,4S,5R)-4-bromo-4-chloro-5-(2,4-dioxo-3,4-dihydropyrimidin-1(2H)-yl)-3-hydroxytetrahydrofuran-2-yl)methoxy)(phenoxy)phosphoryl)amino)propanoate

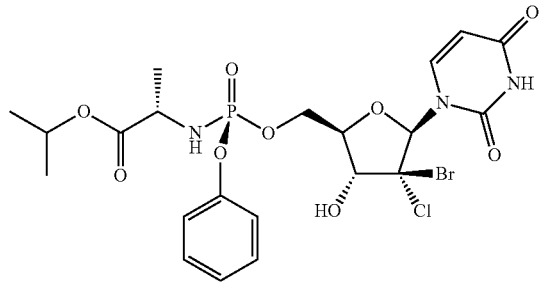 [SMILES: CC(C)OC(=O)[C@H](C)N[P@](=O)(OC[C@H]1O[C@@H](n2ccc(=O)[nH]c2=O)[C@@](Cl)(Br)[C@@H]1O)Oc1ccccc1]

The product of Example 46H (12 mg, 0.035 mmol) was reacted with the corresponding phosphoramidate prodrug moiety compound. The crude product was purified by column chromatography on silica gel eluting with a solvent gradient of 0-5% methanol in dichloromethane to give the title compound (7.5 mg, 35%); $^1$H NMR (400 MHz, DMSO-d6) δ 11.58 (s, 1H), 7.60 (d, J=8.1 Hz, 1H), 7.34 (dd, J=8.6, 7.2 Hz, 2H), 7.24-7.10 (m, 3H), 6.89 (d, J=6.0 Hz, 1H), 6.38 (s, 1H), 6.06 (dd, J=13.0, 10.1 Hz, 1H), 5.55 (d, J=8.2 Hz, 1H), 4.82 (hept, J=6.3 Hz, 1H), 4.48-4.40 (m, 1H), 4.39-4.21 (m, 2H), 4.01-3.94 (m, 1H), 3.85-3.70 (m, 1H), 1.20 (d, J=7.0 Hz, 3H), 1.12 (d, J=6.2 Hz, 6H); MS (ESI+) m/z 611.9 (M+H)$^+$.

The foregoing description of the present invention provides illustration and description, but is not intended to be exhaustive or to limit the invention to the precise one disclosed. Modifications and variations are possible in light of the above teachings or may be acquired from practice of the invention. Thus, it is noted that the scope of the invention is defined by the claims and their equivalents.

What is claimed is:

1. A compound of Formula VII", or a pharmaceutically acceptable salt thereof

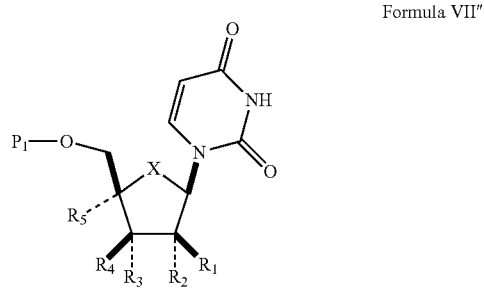

Formula VII"

wherein,

X is selected from the group consisting of O and C=CH$_2$;

R$_1$ and R$_2$ are independently selected from the group consisting of F, Cl, Br, CH$_3$, CHF$_2$ and CCH, R$_3$, R$_4$ and R$_5$ are independently selected from the group consisting of H, D, F, N$_3$, OCH$_3$, CN, OH, 1H-tetrazol-5-yl, 2H-tetrazol-2-yl, 1H-tetrazol-1-yl, 1H-imidazol-1-yl, 1H-imidazol-2-yl and 1H-imidazol-5-yl; and P$_1$ is selected from a group consisting of:

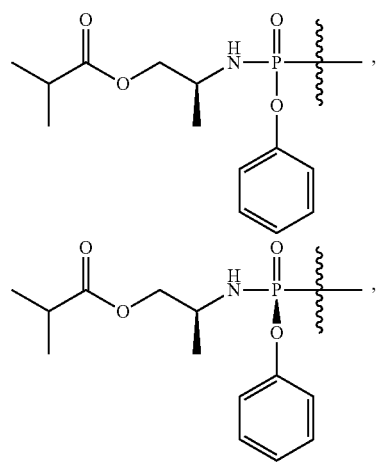

111
-continued
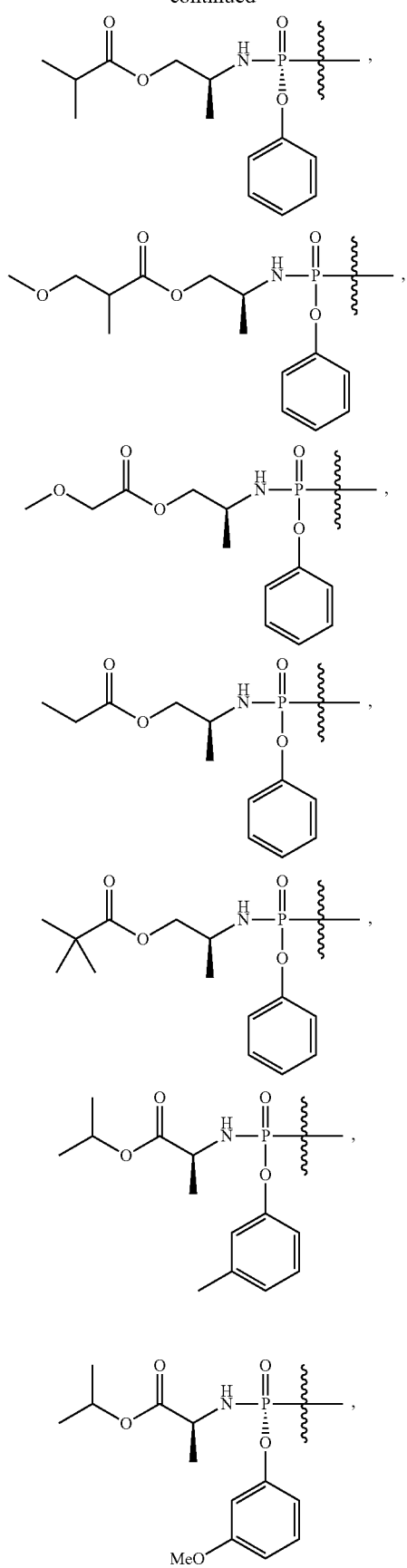
112
-continued
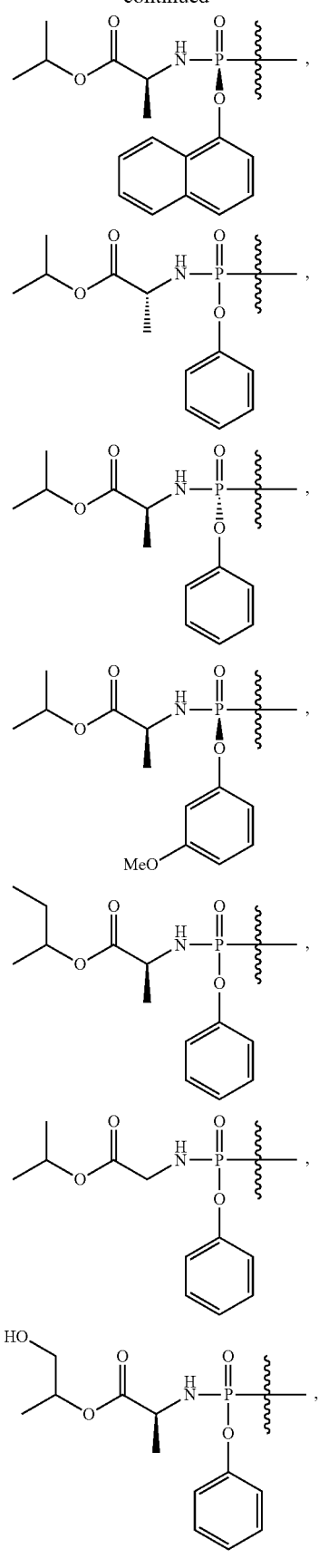

113
-continued
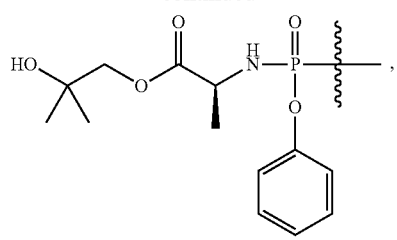
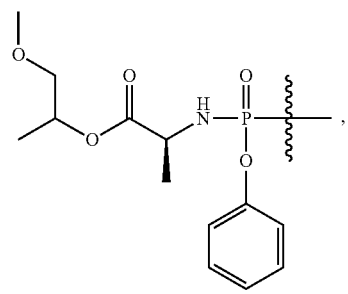
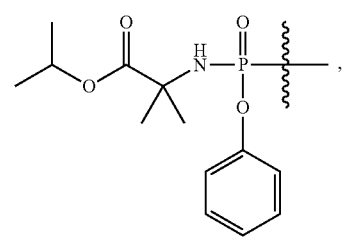
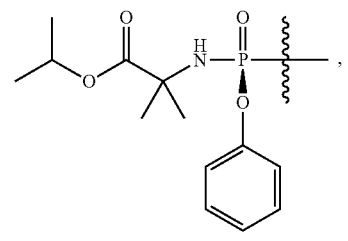
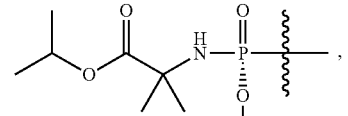
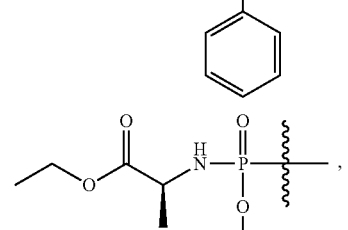
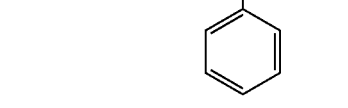
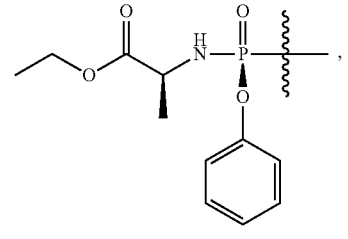
114
-continued
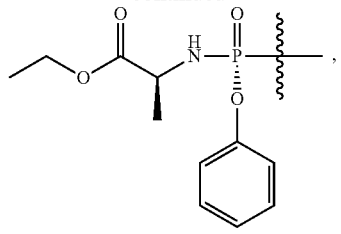
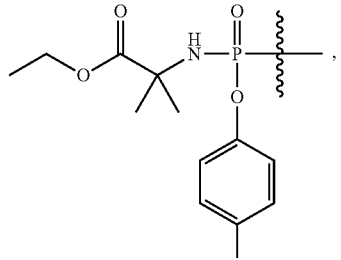
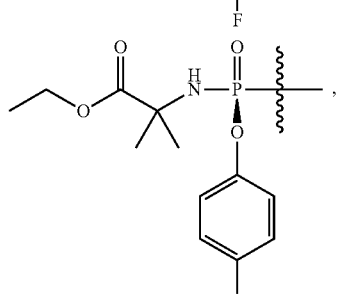
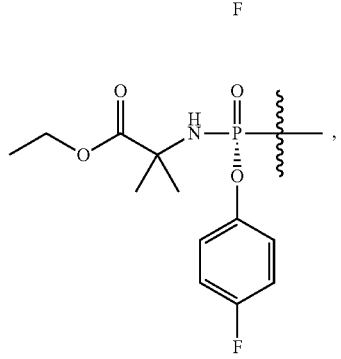
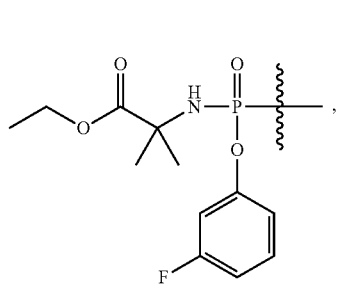
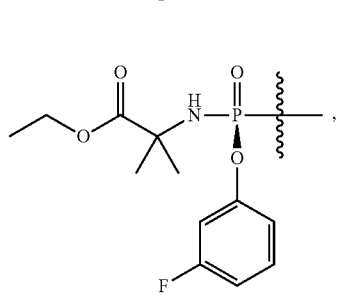

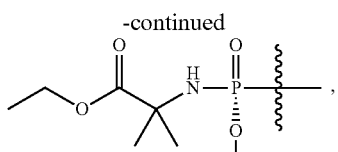

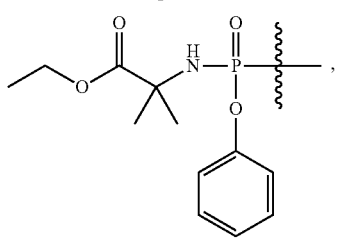

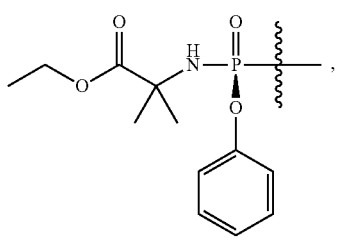

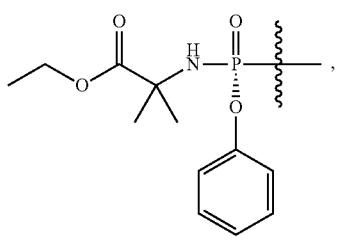

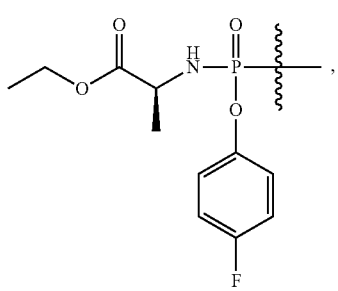

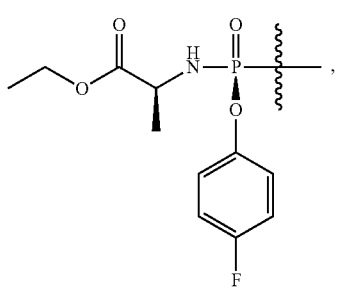

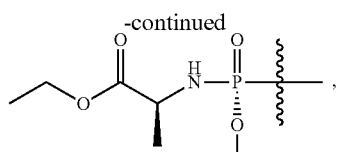

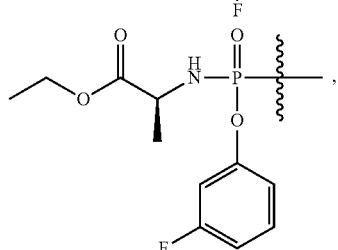

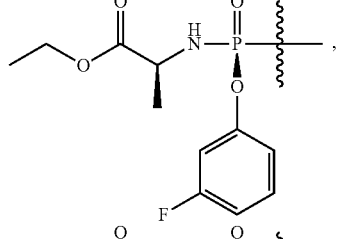

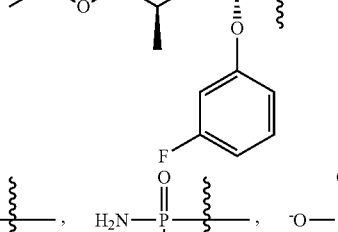

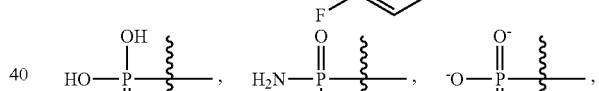

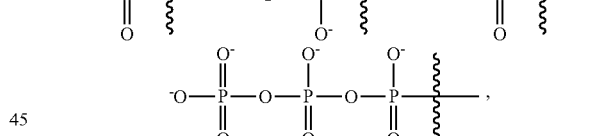

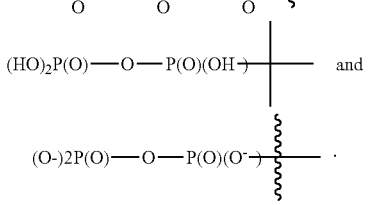

2. The compound of claim 1, or a pharmaceutically acceptable salt thereof, wherein $R_1$ is Br and $R_2$ is F or $R_1$ is Cl and $R_2$ is F.

3. The compound of claim 1, or a pharmaceutically acceptable salt thereof, wherein $R_1$ is Br and $R_2$ is F.

4. The compound of claim 1, or a pharmaceutically acceptable salt thereof, wherein $R_3$ is OH and $R_4$ is H.

5. The compound of claim 1, or a pharmaceutically acceptable salt thereof, wherein $R_3$ is OH.

6. The compound of claim 1, or a pharmaceutically acceptable salt thereof, wherein X is O.

7. The compound of claim 1, or a pharmaceutically acceptable salt thereof, wherein $R_5$ is selected from a group consisting of H, D, F, N₃, OCH₃, CN, OH, 1H-tetrazol-5-yl, 2H-tetrazol-2-yl, 1H-tetrazol-1-yl, 1H-imidazol-1-yl, 1H-imidazol-2-yl and 1H-imidazol-5-yl.

8. The compound of claim 1, or a pharmaceutically acceptable salt thereof, wherein said compound is selected from a group consisting of:
- (S)-isopropyl 2-(((S)-(((2R,3R,4R,5R)-4-bromo-4-chloro-5-(2,4-dioxo-3,4-dihydropyrimidin-1(2H)-yl)-3-hydroxytetrahydrofuran-2-yl)methoxy)(phenoxy)phosphoryl)amino) propanoate,
- (S)-isopropyl 2-(((S)-(((2R,3R,4S,5R)-4-bromo-5-(2,4-dioxo-3,4-dihydropyrimidin-1(2H)-yl)-4-fluoro-3-hydroxytetrahydrofuran-2-yl)methoxy)(phenoxy)phosphoryl)amino)propanoateethyl 2-(((R)-(((2R,3R,4S,5R)-4-bromo-5-(2,4-dioxo-3,4-dihydropyrimidin-1(2H)-yl)-4-fluoro-3-hydroxytetrahydrofuran-2-yl)methoxy)(phenoxy)phosphoryl)amino)-2-methylpropanoate,
- ethyl 2-(((((2R,3R,4R,5R)-5-(2,4-dioxo-3,4-dihydropyrimidin-1(2H)-yl)-4-fluoro-3-hydroxy-4-methyltetrahydrofuran-2-yl)methoxy)(phenoxy)phosphoryl)amino)-2-methylpropanoate,
- ethyl 2-(((((2R,3R,4R,5R)-4-chloro-5-(2,4-dioxo-3,4-dihydropyrimidin-1(2H)-yl)-3-hydroxy-4-methyltetrahydrofuran-2-yl)methoxy)(phenoxy)phosphoryl)amino)-2-methylpropanoate,
- ethyl 2-(((((2R,3R,5R)-4,4-dichloro-5-(2,4-dioxo-3,4-dihydropyrimidin-1(2H)-yl)-3-hydroxytetrahydrofuran-2-yl)methoxy)(phenoxy)phosphoryl)amino)-2-methylpropanoate, and
- (S)-isopropyl 2-(((S)-(((2R,3R,4S,5R)-4-bromo-4-chloro-5-(2,4-dioxo-3,4-dihydropyrimidin-1(2H)-yl)-3-hydroxytetrahydrofuran-2-yl)methoxy)(phenoxy) phosphoryl) amino)propanoate.

9. The compound of claim 1, where said compound is (S)-isopropyl 2-(((S)-(((2R,3R,4S,5R)-4-bromo-5-(2,4-dioxo-3,4-dihydropyrimidin-1(2H)-yl)-4-fluoro-3-hydroxytetrahydrofuran-2-yl)methoxy)(phenoxy)phosphoryl)amino)propanoate, or a pharmaceutically acceptable salt thereof.

10. The compound of claim 1, where said compound is Ethyl 2-(((((2R,3R,4R,5R)-4-bromo-4-chloro-5-(2,4-dioxo-3,4-dihydropyrimidin-1(2H)-yl)-3-hydroxytetrahydrofuran-2-yl)methoxy)(phenoxy)phosphoryl)amino)-2-methylpropanoate, or a pharmaceutically acceptable salt thereof.

11. The compound of claim 1, where said compound is Ethyl 2-(((R)-(((2R,3R,4R,5R)-4-bromo-4-chloro-5-(2,4-dioxo-3,4-dihydropyrimidin-1(2H)-yl)-3-hydroxytetrahydrofuran-2-yl)methoxy)(phenoxy)phosphoryl)amino)-2-methylpropanoate, or a pharmaceutically acceptable salt thereof.

12. The compound of claim 1, where said compound is Ethyl 2-(((S)-(((2R,3R,4R,5R)-4-bromo-4-chloro-5-(2,4-dioxo-3,4-dihydropyrimidin-1(2H)-yl)-3-hydroxytetrahydrofuran-2-yl)methoxy)(phenoxy)phosphoryl)amino)-2-methylpropanoate, or a pharmaceutically acceptable salt thereof.

13. The compound of claim 1, where said compound is Ethyl 2-(((S)-(((2R,3R,4S,5R)-4-bromo-5-(2,4-dioxo-3,4-dihydropyrimidin-1(2H)-yl)-4-fluoro-3-hydroxytetrahydrofuran-2-yl)methoxy)(phenoxy)phosphoryl)amino)-2-methylpropanoate, or a pharmaceutically acceptable salt thereof.

14. A method for treating HCV, comprising administering a compound or salt of claim 1 to a patient infected with Hepatitis C Virus.

15. A method for treating HCV, comprising administering a compound or salt of claim 7 to a patient infected with Hepatitis C Virus.

16. A pharmaceutical composition comprising a compound or salt of claim 1.

17. A pharmaceutical composition comprising a compound or salt of claim 8.

* * * * *